United States Patent [19]
Sreekrishna et al.

[11] Patent Number: 5,827,684
[45] Date of Patent: Oct. 27, 1998

[54] PRODUCTION OF BACILLUS ENTOMOTOXINS IN METHYLOTROPHIC YEAST

[75] Inventors: Kotikanyadanam Sreekrishna; William D. Prevatt, both of Bartlesville, Okla.; Gregory P. Thill, Milton, Mass.; Geneva R. Davis; Patricia Koutz, both of San Diego, Calif.; Kathryn A. Barr; Sharon A. Hopkins, both of Bartlesville, Okla.

[73] Assignee: Research Corporation Technologies, Inc., Tucson, Ariz.

[21] Appl. No.: 231,342

[22] Filed: Apr. 19, 1994

Related U.S. Application Data

[63] Continuation of Ser. No. 926,448, Aug. 7, 1992, abandoned.

[51] Int. Cl.⁶ .............................. C12N 1/19; C12N 15/32; C12N 15/63; C12N 21/02
[52] U.S. Cl. ................ 435/69.1; 435/254.2; 435/254.23; 435/320.1; 536/23.7
[58] Field of Search ................................ 536/23.7, 23.71; 435/320.1, 254.2, 254.23, 69.1; 424/93.2; 514/12

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,652,628 | 3/1987 | Walfield et al. | 530/324 |
| 4,695,455 | 9/1987 | Barnes et al. | 424/93.2 |
| 4,695,460 | 9/1987 | Barnes et al. | 424/93.43 |
| 4,764,372 | 8/1988 | Herrnstadt et al. | 424/93.461 |
| 4,766,203 | 8/1988 | Krieg et al. | 424/93.461 |
| 4,771,131 | 9/1988 | Herrnstadt et al. | 536/23.71 |
| 4,902,507 | 2/1990 | Morris et al. | 424/93.461 |
| 4,910,016 | 3/1990 | Gaertner et al. | 424/93.461 |
| 4,910,136 | 3/1990 | Herrnstadtt et al. | 435/69.1 |
| 4,918,006 | 4/1990 | Ellar et al. | 435/69.1 |
| 5,010,001 | 4/1991 | Pollock | 435/69.1 |
| 5,380,831 | 1/1995 | Adang et al. | 536/23.71 |
| 5,389,540 | 2/1995 | Makoff et al. | 435/69.3 |

FOREIGN PATENT DOCUMENTS

| | | |
|---|---|---|
| 0 093 062 | 11/1983 | European Pat. Off. . |
| 0 341 746 | 11/1989 | European Pat. Off. . |
| 0 374 282 | 6/1990 | European Pat. Off. . |
| 0 454 485 | 10/1991 | European Pat. Off. . |
| 0 200 344 | 12/1991 | European Pat. Off. . |
| 2 188 049 | 9/1987 | United Kingdom . |

OTHER PUBLICATIONS

Baumann, et al., "Purification of the Lavicidal Toxin of *Bacillus sphaericus* and Evidence for High–Molecular–Weight Precursors", *J. Bacteriol.* 163, pp. 738–747 (Aug. 1985).

(List continued on next page.)

*Primary Examiner*—Robert A. Wax
*Assistant Examiner*—Eric Grimes
*Attorney, Agent, or Firm*—Scully, Scott, Murphy & Presser

[57] ABSTRACT

A method for producing one or more Bacillus toxin polypeptides by culturing methylotrophic yeast cells which have a gene(s) capable of expressing the Bacillus toxin polypeptide(s) in such cells under conditions that the gene(s) is/are transcribed is provided. The toxin polypeptide encoding segment of the gene(s) has a G+C content of about 40%–55%, and preferably comprises methylotrophic yeast codons. The preferred species of yeast for expressing such synthetic Bacillus toxin gene(s) is *Pichia pastoris*. Bacillus toxin polypeptides encoded by synthetic genes are expressed at high levels in transformed methylotrophic yeast cells. The toxin expressing cells may be administered as live cells or heat-killed whole cells to provide an insecticidal composition for killing susceptible insect larvae. Also provided by the present invention are DNAs capable of transforming methylotrophic yeast to express one or more Bacillus toxin polypeptides, cultures of such yeast cells transformed with such DNAs and novel Bacillus toxin polypeptides made by the method of the invention. The transformed yeast cells of the present invention are readily ingested as food by insect larvae which are susceptible to the toxin polypeptides.

31 Claims, 21 Drawing Sheets

OTHER PUBLICATIONS

Baumann, et al., "Cloning of the Gene for the Larvicidal Toxin of *Bacillus spaericus* 2362: Evidence for a Family of Related Sequences", *J. Bacteriol. 169*, pp. 4061–4067 (Sep. 1987).

Berry, et al., "*Bacillus sphaericus* strain 2362: Indentification and Nucleotide Sequence of the 41.9kDa Toxin Gene", *Nucl. Acids Res. 15*, p. 5891 (1987)

Bourgouin et al., "Transfer of the Toxin Protein Genes of *Bacillis sphaericus* into *Bacillus thuringiensis Subsp. israelensis* and Their Expression", *Appl. and Environ. Micro. 56*, pp. 340–344 (1990).

Broadwell, et al., "Sporulation–Associated Activation of *Bacillis sphaericus* Larvicide", *Appl. and Environ. Micro. 52*, pp. 758–764 (1986).

Clare, et al., "High–Level Expression of Tetanus Toxin Fragment C in *Pichia Pastoris* Strains Containing Multiple Tandem Integrations of the Gene", *Bio/Technology 9*, pp. 455–460 (1991).

Davidson, E.W., "Purification and Properties of Soluble Cytoplasmic Toxin from the Mosquito Pathogen *Bacillus sphaericus* Strain 1593", *J. Invert. Pathol. 39*, pp. 6–9 (1982).

Davidson, et al., "Comparative Field Trials of *Bacillus sphaericus* Strain 1593 and *B. thuringiensis* var. israelensis Commercial Powder Formulations", *J. Econ. Entomol. 74*, pp. 350–354 (1981).

Ernst, J.F., "Codon Usage and Gene Expression", *Trends In Biotechnology 6*, pp. 196–199 (1988).

Fischhoff, et al., "Insect Tolerant Transgenic Tomato Plants", *Bio/Technology 5*, pp. 807–813 (1987).

Ganesan, et al., "Cloning and Expression in *Escherichia coli* of a DNA Fragment from *Bacillus sphaericus* coding for Biocidal Activity Against Mosquito Larvae", *Mol. Gen. Genet. 189*, pp. 181–183 (1983).

Louis, et al., "Biocide Gene(s) and Biocidal Activity in Different Strains of *Bacillus sphaericus*. Expression of the Gene(s) in *E. coli* Maxicells", *Mol. Gen. Genet. 195*, pp. 23–28 (1984).

Lysenko, et al., "Five New Mosquito Larvicidal Strains of *Bacillus Sphaericus* from Non–Mosquito Origins", *J. Am. Mosq. Control. Assoc. 1*, pp. 369–371 (1975).

Mulla, et al., "Efficacy and Persistence of the Microbiol Agent *Bacillus sphaericus* Against Mosquito Larvae in Organically Enriched Habitats", *Mosquito News 44*, pp. 166–173 (1984).

Mulla, et al., "Larvicidal Activity and Field Efficacy of *Bacillus sphaericus* Strains Against Mosquito Larvae and Their Safety to Nontarget Organisms", *Mosquito News 44*, pp. 336–342 (1984).

Payne, et al., "Insecticidal Activity of the Crystalline Parasporal Inclusions and Other Components of the *Bacillus sphaericus* 1593 Spore Complex", *J. Invert. Pathol. 43*, pp. 383–388 (1984).

Peferoen, M., "*Bacillus thuringiensis* in Crop Protection", *Argo–Industry Hi–Tech*, 2(6) pp. 5–9 (1991).

Rowe, et al., "Bioprocess Developments in the Production of Bioinsecticides by *Bacillus Thuringiensis*", *CRC Critical Reviews in Biotechnology 6*, pp. 87–127 (1987).

Stahly, et al., "The Genus Bacillus–Insect Pathogens", *vol. II, The Prokaryotes (Second Edition), A Handbook of the Biology of Bacteria: Ecophysiology, Isolation, Identification and Applications*, pp. 1697–1745 (Springer–Verlag, New York, NY 1991).

Tandeau de Marsac, et al., "Expression of the Larvicidal Gene of *Bacillus sphaericus* 1593M in the Cyanobacterium *Anacystis nidulans R2*", *Mol. Gen Genet. 209*, pp. 396–398 (1987).

Thorne, et al., "Structural Similarity Between the Lepidoptera– and Diptera–Specific Insecticidal Endotoxin Genes of *Bacillus thuringiensis* subsp. 'kurstaki' and 'israelensis'", *J. Bacteriol. 166*, pp. 801–811 (1986).

Yamamoto, et al, "Nucleotide Sequence of the Gene Coding for a 130–kDa Mosquitocidal Protein of *Bacillus thuringiensis israelensis*", *Gene 66*, pp. 107–120 (1988).

Yousten, et al., "Batch and Continuous Culture Production of the Mosquito Larval toxin of *Bacillus sphaericus* 2362", *J. Indus. Microbiol. 2*, pp. 277–283 (1987).

Souza et al. (1988) *J. Biotechnology*, vol. 7, pp. 71–82, "Cloning and expression in *Escherichia coli* of two DNA fragments from *Bacillus sphaericus* encoding mosquito–larvicidal activity".

Schnepf et al., J. Biol. Chem. 260:6264–6272 (1985).

Cregg et al., Biotechnology 11:905–910 (1993).

Cregg, J.M. et al., In Hershberger, C.L. et al. (Eds), Genetics and Molecular Biology of Industrial Microorganisms, Amer. Soc. Microbiol., Washington, DC, 1989, pp. 343–352.

Koutz, P. et al., Yeast 5:167–177 (1989).

Romanos, M.A. et al.; Nucleic Acids Res. 19:1461–1467 (1991).

Clare, J.J. et al.; Bio/Technology 9:455–460 (1991).

Baumann, L. et al.; J. Bacteriol. 170:2045–2050 (1988).

Thanabalu, T. et al.; Appl. Environ. Microbiol. 58:905–910 (Mar. 1992).

FREQUENCY OF CODON USAGE IN HIGHLY EXPRESSED PICHIA PASTORIS GENES

| AmAcid | Codon | Number | Fraction | AmAcid | Condon | Number | Fraction |
|---|---|---|---|---|---|---|---|
| Gly | GGG | 0.00 | 0.00 | Trp | TGG | 39.00 | 1.00 |
| Gly | GGA | 59.00 | 0.22 | End | TGA | 0.00 | 0.00 |
| Gly | GGT | 197.00 | 0.74 | Cys | TGT | 35.00 | 0.83 |
| Gly | GGC | 9.00 | 0.03 | Cys | TGC | 7.00 | 0.17 |
| Glu | GAG | 112.00 | 0.58 | End | TAG | 1.00 | 0.20 |
| Glu | GAA | 80.00 | 0.42 | End | TAA | 4.00 | 0.80 |
| Asp | GAT | 56.00 | 0.32 | Tyr | TAT | 18.00 | 0.12 |
| Asp | GAC | 118.00 | 0.68 | Tyr | TAC | 128.00 | 0.38 |
| Val | GTG | 10.00 | 0.05 | Leu | TTG | 120.00 | 0.52 |
| Val | GTA | 8.00 | 0.04 | Leu | TTA | 21.00 | 0.09 |
| Val | GTT | 107.00 | 0.50 | Phe | TTT | 24.00 | 0.19 |
| Val | GTC | 87.00 | 0.41 | Phe | TTC | 104.00 | 0.81 |
| Ala | GCG | 1.00 | 0.00 | Ser | TCG | 6.00 | 0.03 |
| Ala | GCA | 25.00 | 0.10 | Ser | TCA | 14.00 | 0.07 |
| Ala | GCT | 147.00 | 0.60 | Ser | TCT | 89.00 | 0.47 |
| Ala | GCC | 71.00 | 0.29 | Ser | TCC | 71.00 | 0.37 |
| Arg | AGG | 2.00 | 0.01 | Arg | CGG | 2.00 | 0.01 |
| Arg | AGA | 111.00 | 0.79 | Arg | CGA | 0.00 | 0.00 |
| Ser | AGT | 8.00 | 0.04 | Arg | CGT | 26.00 | 0.18 |
| Ser | AGC | 3.00 | 0.02 | Arg | CGC | 0.00 | 0.00 |
| Lys | AAG | 145.00 | 0.79 | Gln | CAG | 31.00 | 0.34 |
| Lys | AAA | 38.00 | 0.21 | Gln | CAA | 59.00 | 0.66 |
| Asn | AAT | 18.00 | 0.13 | His | CAT | 11.00 | 0.13 |
| Asn | AAC | 119.00 | 0.87 | His | CAC | 77.00 | 0.88 |
| Met | ATG | 60.00 | 1.00 | Leu | CTG | 35.00 | 0.15 |
| Ile | ATA | 0.00 | 0.00 | Leu | CTA | 7.00 | 0.03 |
| Ile | ATT | 93.00 | 0.56 | Leu | CTT | 43.00 | 0.18 |
| Ile | ATC | 72.00 | 0.44 | Leu | CTC | 7.00 | 0.03 |
| Thr | ACG | 5.00 | 0.03 | Pro | CCG | 0.00 | 0.00 |
| Thr | ACA | 8.00 | 0.05 | Pro | CCA | 97.00 | 0.57 |
| Thr | ACT | 86.00 | 0.50 | Pro | CCT | 66.00 | 0.39 |
| Thr | ACC | 74.00 | 0.43 | Pro | CCC | 7.00 | 0.04 |

FIG.1

```
      MetArgAsnLeuAspPheIleAspSerPheIleProThrGluGlyLysTyrIleArgVal
  1   ATGAGAAATTTGGATTTTATTGATTCTTTATACCCACAGAAGAAGTACATTCGCGTT      60
      |||||  |||||  |||| ||  || ||   || || ||||||  ||||||| |||||
(H3/RI)--ATGAGAAACTTGGACTTCATCGACTCCTTCATCCCAACTGAGGGTAAGTACATCAGAGTC

MetAspPheTyrAsnSerGluTyrProPheCysIleHisAlaProSerAlaProAsnGly
  61  ATGGATTTTTATAATAGCGAGTATCCTTTCTGTATACCAGCACCCTCAGCCCCTAATGGG    120
      ||||| || || ||  || ||||| ||  |  |||  || | ||||| || || ||
      ATGGACTTCTACAACTCCGAGTACCCATTCTGTATCCACGCTCCATCCGCTCCAAACGGT

AspIleMetThrGluIleCysSerArgGluAsnAsnGlnTyrPheIlePhePheProThr
  121 GATATCATGACAGAAATCTGTAGCAGAGAAAATAATCAATATTTTATTTTTCCTACT       180
      || || ||||  ||  ||||  ||||| ||||| || ||||||||||| || ||| ||
      GACATCATGACTGAAATCTGTTCCAGAGAGAACAACCAGTACTTCATCTTCTTCCCAACT

AspAspGlyArgValIleIleAlaAsnArgHisAsnGlySerValPheThrGlyGluAla
  181 GATGATGGTCGAGTAATTATTGCAAATAGGCATAATGGGTCCGTTTTTACCGGAGAAGCC    240
      || || || || || ||  ||||  ||  || || ||  || || ||  ||||| || 
      GACGACGGTAGAGTCATCATCGCTAACAGACACAACGGTTCCGTCTTCACTGGTGAGGCT

ThrSerValValSerAspIleTyrThrGlySerProLeuGlnPhePheArgGluValLys
  241 ACAAGTGTAGTATCAGATATCTATACTGGTAGCCCATTACAGTTTTTTAGAGAGGTCAAA    300
      ||  || || || || ||||| |||  |||| ||   ||||| |||||| ||||| |||
      ACTTCCGTCGTCTCCGACATCTACACTGGTTCCCCACTGCAGTTCTTCAGAGAGGTCAAG
                                                       (Pst I)

ArgThrMetAlaThrTyrTyrLeuAlaIleGlnAsnProGluSerAlaThrAspValArg
  301 AGAACTATGGCAACTTATTATTTAGCGATACAAAATCCTGAATCCGCAACAGATGTGAGA    360
      ||||||||||| || ||||| ||  | || ||||| || ||||| || || || || ||
      AGAACTATGGCTACTTACTTCCTGGCTATCCAGAACCCAGAGTCCGCTACTGACGTCAGA

AlaLeuGluProHisSerHisGluLeuProSerArgLeuTyrTyrThrAsnAsnIleGlu
  361 GCTCTAGAACCGCATTCCCATGAGCTGCCATCTCGCCTTTATTACACTAACAATATTGAA    420
      || ||||| || |||||||| || ||||| || || ||||| ||||| || || || ||
      GCTTTGGAGCCACACTCCCACGAGTTGCCATCCAGATTGTACTACACTAACAACATCGAG
```

FIG.2A

```
        AsnAsnSerAsnIleLeuIleSerAsnLysGluGlnIleTyrLeuThrLeuProSerLeu
421     AATAATAGCAACACATATTAATTTCTAATAAGGAACAAATATATTAACCTTGCCTTCACTT
        || ||   ||||| || ||| |||| || ||  ||||| |||| ||||||| ||||| |
        AACAACTCCAACATCTTGATCTCCAACAAGAGGAGACAGATTTACTTGACTTTGCCATCCTTG

ProGluAsnGluGlnTyrProLysThrProValLeuSerGlyIleAspAspIleGlyPro
481     CCAGAAAACGAGCAATACCCTAAAACTCCAGTATTAAGCGGTATCGATGATATAGGACCT
        |||| |  ||||| || ||| |||| ||||||| ||  ||| ||| ||||| || |||
        CCAGAGAACGAGCAGTACCCAAAGACTCCAGTCTTGTCCGGTATCGACGACATCGGTCCA

AsnGlnSerGluLysSerIleIleGlySerThrLeuIleProCysIleMetValSerAsp
541     AATCAATCAGAGAAATCAATAATAGGAAGTACTCTTATCCCATGTATAATGGTTTCGGAT
        || || || ||  ||||| || ||  |  ||  ||||||||||||||| ||||| ||
        AACCAGTCCGAGAAGTCCATCATCGGTTCCACTTGGATCCCATGTATCATGGTCTCCGAC
                                         (BamH I)

PheIleSerLeuGlyGluArgMetLysThrThrProTyrTyrTyrValLysHisThrGln
601     TTTATTAGTTTGGGGGAGAGAATGAAAACCACTCCATATTATTATGTAAAGCACACTCAA
        || ||||| ||| | || |||||||| || ||||| ||||||||  ||||| ||||| |
        TTCATCTCCTTGGGTGAGAGAATGAAGACTACTCCATACTACTACGTCAAGCACACTCAG

TyrTrpGlnSerMetTrpSerAlaLeuPheProProGlySerLysGluThrLysThrGlu
661     TATTGGCAAAGCATGTGGTCCGCGCTCTTTCCACCCGGCTCTAAAGAGACAAAAACTGAG
        |||||||| || ||||| || |  ||||| ||||| || |||||||||  ||| ||||
        TACTGGCAGTCCATGTGGTCCGCTTTGTTCCCACCAGGTTCCAAGGAGACTAAGACTGAG

LysSerGlyIleThrAspThrSerGlnIleSerMetThrAspGlyIleAsnValSerIle
721     AAATCAGGTATCACTGACACTTCTCAAATATCTATGACTGACGGGATTAATGTTTCAATC
        ||||| || ||| |||||||| || ||||| |||||||| |||| ||| || |||||||
        AAGTCCGGTATCACTGACACTTCCCAGATTTCCATGACTGACGGTATCAACGTCTCCATC

GlyAlaAspPheGlyLeuArgPheGlyAsnLysThrPheGlyIleLysGlyPheThr
781     GGAGCAGATTTCGGATTAAGGTTTGGAAATAAAACGTTTGGAATTAAGGGGTTCACC
        || || ||||||||| || || ||||| || || ||||  |||||| || || ||
        GGTGCTGACTTCGGTTTGAGATTCGGTAACAAGACTTTCGGTATCAAGGGTTTCACT
```

FIG. 2B

```
            TyrAspThrLysThrGlnIleThrAsnThrSerGlnLeuLeuIleGluThrThrTyrThr
      841   TATGATACAAAGACTCAAATAACTAATACCTCCCAATTGTTAATAGAAACAACTTATACT   900
            || || ||||| || |||| || || |||||||| || |||||| ||| ||||| |||
            TACGACACTAGAGACTCAGATGATCACTAACACTTCCCAGTTGTTGATCGAGACTTACACC

ArgGluTyrThrAsnThrGluAsnPheProValArgTyrThrGlyTyrValLeuAlaSer
      901   AGAGAATACACAAATACAGAGAAATTTTCCTGTTAGATACAGGCTATGTTTTAGCGTCA    960
             | ||| ||||| || || || |||||||| || ||||| || ||||| || |||||
            CGGGAGTACACTAACACTGAGAACTTCCCAGTCAGATACACTGGTTACGTCTTGGCTTCC
              |
            (Sma I)

GluPheThrLeuHisArgSerAspGlyThrGlnValAsnThrIleProTrpValAlaLeu
      961   GAATTTACTTTACATCGTAGTGATGGAACTCAGGTTAATACGATCCCATGGGTTGCTTTA   1020
            || || || || |||   | |  | |||||||| ||||| || ||||| ||||| || |
            GAGTTCACTTTGCACAGATCCGACAGTTCAGGTCAACACTATCCCATGGGTCGCTTTG

AsnAspAsnTyrThrThrIleAlaArgTyrProHisPheAlaSerGluProLeuLeuGly
     1021   AACGATAACTATACAACAATAGCAAGATATCCACATTTTGCAAGTGAACCTTTACTAGGA   1080
            || || ||||| || || || || |||||||| ||||| || || |||||| || |||
            AACGACAACTACACTACTATCGCTAGATACCCACACTTCGCTTCCGAGCCATTGTTGGGT

AsnThrLysIleIleThrAspAspGlnAsnEnd
     1081   AATACAAAGATTATTACAGATGATCAAAACTAA   1113          SEQ. ID NO: 6
            || || ||||| || || || || || |||||                 SEQ. ID NO: 5
            AACACTAAGATCATCACTGACGACCAGAACTAA--(EcoR I)       SEQ. ID NO: 7
```

FIG. 2C

| | SEQUENCE | SIZE | SEQ. ID NO: |
|---|---|---|---|
| 5' TO 3' | | | |
| 1 | GTTCTTCAGAGAGGTCAAGAGAACTATGGCTACTTACTACTGGCTATCCAGA | 53mer | 8 |
| 2 | ACCCAGAGTCCGCTACTGACGTCAGAGCTTTGGAGCCACAC | 41mer | 9 |
| 3 | TCCCACGAGTTGCCATCCAGATTGTACTACACTAACAACA | 40mer | 10 |
| 4 | TCGAGAACAACTCCAACATCTTGATCTCCAACAAGGAGC | 39mer | 11 |
| 5 | AGATTTACTTGACTTTGCCATCCTTGCCAGAGAACGAGCA | 40mer | 12 |
| 6 | GTACCCAAAGACTCCAGTCTTGTCCGGTATCGACGACATC | 40mer | 13 |
| 7 | GGTCCAAACCAGTCCGAGAAGTCCATCATCGGTTCCACTTG | 41mer | 14 |
| 3' TO 5' | | | |
| 8 | GATCCAAGTGGAACCGATGATGGACTTCTCGGACTGGTTTGGACCGATGTCGTC | 54mer | 15 |
| 9 | GATACCGGACAAGACTGGAGTCTTTGGGTACTGCTCGTTCT | 41mer | 16 |
| 10 | CTGGCAAGGATGGCAAAGTCAAGTAAATCTGCTCCTTGTT | 40mer | 17 |
| 11 | GGAGATCAAGATGTTGGAGTTGTTCTCGATGTTGTTAGT | 39mer | 18 |
| 12 | GTAGTACAATCTGGATGGCAACTCGTGGGAGTGTGGCTCCA | 41mer | 19 |
| 13 | AAGCTCTGACGTCAGTAGCGGACTCTGGGTTCTGGATAGC | 40mer | 20 |
| 14 | CAAGTAGTAAGTAGCCATAGTTCTCTTGACCTCTCTGAAGAACTGCA | 47mer | 21 |

FIG.2D

```
AAGCTTCGAA ACG ATG TGC GAT TCT AAA GAT AAT TCT GGA GTT TCT GAA         49
            Met Cys Asp Ser Lys Asp Asn Ser Gly Val Ser Glu
             1               5                  10

AAA TGC GGA AAA AAG TTC ACC AAC TAC CCA TTG AAC ACC ACC CCA ACC        97
Lys Cys Gly Lys Lys Phe Thr Asn Tyr Pro Leu Asn Thr Thr Pro Thr
         15                  20                  25

TCC TTG AAC TAC AAC TTG CCA GAG ATC TCC AAG AAG TAC TTG AAC TTG       145
Ser Leu Asn Tyr Asn Leu Pro Glu Ile Ser Lys Lys Phe Tyr Asn Leu
     30                  35                  40

AAG AAC AAG TAC TCC AGA TAC GGT TAC GGT TTG TCC AAG ACC GAG TTC       193
Lys Asn Lys Tyr Ser Arg Tyr Gly Tyr Gly Leu Ser Lys Thr Glu Phe
 45                  50                  55                  60

CCA TCC TCC ATC GAG AAC TGT CCA TCC AAC GAG TAC TCC ATC ATG TAC       241
Pro Ser Ser Ile Glu Asn Cys Pro Ser Asn Glu Tyr Ser Ile Met Tyr
                 65                  70                  75

GAC AAC AAG GAC CCA AGA TTC TTG ATC ATC AGA TTC TTG GAC GAC GGT       289
Asp Asn Lys Asp Pro Arg Phe Leu Ile Ile Arg Phe Leu Asp Asp Gly
             80                  85                  90

AGA TAC ATC ATC GCC GAC AGA AAC AAC CAC CCA ATC ATC TCC GAG GCC       337
Arg Tyr Ile Ile Ala Asp Arg Asn Asn His Pro Ile Ile Ser Glu Ala
         95                 100                 105

CCA ACC TAC TTG GAC AAC AAC AAG TTG GAC AAC CAC AGA CAC TAC           385
Pro Thr Tyr Leu Asp Asn Asn Lys Leu Asp Asn His Arg His Tyr
     110                 115                 120

ACC GGT GAG GAG AGA CAG AAG TTC GAG CAG GTC GGT TCC GGT GAC TAC       433
Thr Gly Glu Glu Arg Gln Lys Phe Glu Gln Val Gly Ser Gly Asp Tyr
125                 130                 135                 140
```

FIG.3A

```
ATC ACC GGT GAG CAG TTC TTC TAC ACC CAG AAC AAG ACC AGA          481
Ile Thr Gly Glu Gln Phe Phe Tyr Thr Gln Asn Lys Thr Arg
                145                 150                 155

GTC TTG TCC AAC TGT AGA GCC TTG GAC AGC ACC ATC TTG TCC          529
Val Leu Ser Asn Cys Arg Ala Leu Asp Ser Thr Ile Leu Ser
                160                 165                 170

ACC GCC AAG ATC TAC TTC CCA ATC TAC CCA CCA ACC CAG TTG          577
Thr Ala Lys Ile Tyr Phe Pro Ile Tyr Pro Pro Thr Gln Leu
                175                 180                 185

ACC GCC TTC GTC AAC TCC TCC TTC TAC GCC GCC GCC ATC CCA CAG TTG  625
Thr Ala Phe Val Asn Ser Ser Phe Tyr Ala Ala Ala Ile Pro Gln Leu
                190                 195                 200

CCA CAG ACC TCC TTG TTG GAG AAC ATC CCA GAG GAG CCA ACC TCC TTG GAC  673
Pro Gln Thr Ser Leu Leu Glu Asn Ile Pro Glu Glu Pro Thr Ser Leu Asp
                205                 210                 215                 220

GAC TCC GGT GTC TTG CCA AAG GAC GCC GTC AGA GCC AAG GGA TCC      721
Asp Ser Gly Val Leu Pro Lys Asp Ala Val Arg Ala Lys Gly Ser
                225                 230                 235

GCC TTG TTG CCA TGT ATC ATC GTC CAC GAC TAC TTG AAC AAC TCC      769
Ala Leu Leu Pro Cys Ile Ile Val His Asp Tyr Leu Asn Asn Ser
                240                 245                 250

GAC AAG ATG TTC AAG TTC AAC ACC TAC TAC TTG TTG GAG TAC AAG GAG TAC  817
Asp Lys Met Phe Lys Phe Asn Thr Tyr Tyr Leu Leu Glu Tyr Lys Glu Tyr
                255                 260                 265

TGG CAC CAG TTG TGG TCC CAG ATC ATC CCA GCC CAC CAG ACC GTC AAG  865
Trp His Gln Leu Trp Ser Gln Ile Ile Pro Ala His Gln Thr Val Lys
                270                 275                 280
```

FIG. 3B

```
ATC CAG GAG AGA ACC GGT ATC TCC GAG GTC CAG AAC TCC ATG ATC       913
Ile Gln Glu Arg Thr Gly Ile Ser Glu Val Gln Asn Ser Met Ile
285                 290                 295                 300

GAG GAC TTG AAC ATG TAC ATC GGT GCC GAC TTC GGT ATG TTG TAC       961
Glu Asp Leu Asn Met Tyr Ile Gly Ala Asp Phe Gly Met Leu Tyr
         305                 310                 315

TTC AGA TCC TCC GGT TTC AAG GAG CAG ATC ACC AGA GGT TTG AAC AGA  1009
Phe Arg Ser Ser Gly Phe Lys Glu Gln Ile Thr Arg Gly Leu Asn Arg
320                 325                 330

CCA TTG TCC CAG ACC ACC CAG TTG GGT GAG AGA GTC GAG GAG ATG      1057
Pro Leu Ser Gln Thr Thr Gln Leu Gly Glu Arg Val Glu Glu Met
335                 340                 345

GAG TAC TAC AAC TCC AAC GAC GTC GAC GTC AGA TAC AAG TAC GCC      1105
Glu Tyr Tyr Asn Ser Asn Asp Val Asp Val Arg Tyr Lys Tyr Ala
350                 355                 360

TTG GCC AGA GAG TTC ACC TTG AAG AGA TAC AGA GTC AAC GGT GAG ATC GTC AAG  1153
Leu Ala Arg Glu Phe Thr Leu Lys Arg Tyr Arg Val Asn Gly Glu Ile Val Lys
365                 370                 375                 380

AAC TGG GTC GCC GTC GAC GTC GCC TTG GCC TTG ACC TTG ACC TCC TAC CCA      1201
Asn Trp Val Ala Val Asp Val Ala Leu Ala Leu Thr Leu Thr Ser Tyr Pro
         385                 390                 395

AAC GCC CCA ATC ACC ACC AAC CCA ATC CAG TCC CAG TCC ACC ATC GTC ATC      1249
Asn Ala Pro Ile Thr Thr Asn Pro Ile Gln Ser Gln Ser Thr Ile Val Ile
400                 405                 410

AGA TGT GAG GAG AAC TCC TAC GAC CAC ATC TTC AAG ACC CCA TTG ATC          1297
Arg Cys Glu Glu Asn Ser Tyr Asp His Ile Phe Lys Thr Pro Leu Ile
415                 420                 425
```

FIG.3C

```
TTC AAG AAC GGT GAG GTC ATC GTC AAG ACC AAC GAG GAG TTG ATC CCA    1345
Phe Lys Asn Gly Glu Val Ile Val Lys Thr Asn Glu Glu Leu Ile Pro
    430             435             440
```

FIG. 3D

```
AAGCTTCGAA ACGATGTGCG ATTCTAAAGA TAATTCTGGA GTTTCTGAAA AATGCGGAAA AAGTTCACCC AACTACCCAT TGAACACCAC
TTCGAAGCTT TGCTACACGC TAAGATTTCT ATTAAGACCT CAAAGACTTT TTACGCCTTT TTCAAGTGGG TTGATGGGTA ACTTGTGGTG
          10         20         30         40         50         60         70         80         90

CCCAACCTCC TTGAACTACA ACTTGCCAGA GATCTCCAAG AAGTTCTACA ACTTGAAGAA CAAGTACTCC AGAAACGGTT ACGGTTTGTC
GGGTTGGAGG AACTTGATGT TGAACGGTCT CTAGAGGTTC TTCAAGATGT TGAACTTCTT GTTCATGAGG TCTTTGCCAA TGCCAAACAG
          100        110        120        130        140        150        160        170        180

CAAGACCGAG TTCCCATCCT CCATCGAGAA CTGTCCATGT AACGAGTACT CCATCATGTA CGACAACAAG GACCCAAGAT TCTTGATCAG
GTTCTGGCTC AAGGGTAGGA GGTAGCTCTT GACAGGTACA TTGCTCATGA GGTAGTACAT GCTGTTGTTC CTGGGTTCTA AGAACTAGTC
          190        200        210        220        230        240        250        260        270

ATTCTTGTTG GACGACGGTA GATACATCAT CGCCGACAGA GACGACGGTG AGGTCTTCGA CGAGGCCCCA GCTCCGGGGT ACAACAACAA
TAAGAACAAC CTGCTGCCAT CTATGTAGTA GCGGCTGTCT CTGCTGCCAC TCCAGAAGCT GCTCCGGGGT CGAGGCCCCA TGTTGTTGTT
          280        290        300        310        320        330        340        350        360

CCACCCAATC ATCTCCAGAC ACTACACCGG TGAGGAGAGA CAGAAGTTCG AGCAGGTCGG TTCCGGTGAC TACATCACCG GTGAGCAGTT
GGTGGGTTAG TAGAGGTCTG TGATGTGGCC ACTCCTCTCT GTCTTCAAGC TCGTCCAGCC AAGGCCACTG ATGTAGTGGC CACTCGTCAA
          370        380        390        400        410        420        430        440        450

CTTCAGTTC GAAGGTCAAG ACAAGACCAGA AGTCTTGTCC AACTGTAGAG CCTTGGACTC CAGAACCATC TTGTTGTCCA CCGCCAAGAT
GAAGTCAAG CTTCCAGTTC TGTTCTGGTCT TCAGAACAGG TTGACATCTC GGAACCTGAG GTCTTGGTAG AACAACAGGT GGCGGTTCTA
          460        470        480        490        500        510        520        530        540

CTTCCCAATC TACCACCAG GAAGGTTCAAG CCTTCGAGAC CCAGTTGACC GCCTTCGTCA ACTCCTCCTT CTACGCCCGC GCCATCCCAC AGTTGCCACA
GAAGGGTTAG ATGGGTTGTC CTTCCAAGTTC GGAAGCTCTG GGTCAACTGG CGGAAGCAGT TGAGGAGGAA GATGCGGGCG CGGTAGGGTG TCAACGGTGT
          550        560        570        580        590        600        610        620        630

GACCTCCTTG TTGGAGAACA TCCCAGAGCC AACCTCCTTG GACGACTCCG GTGTCTTGCC AAAGGACGCC GTCAGAGCCG TCAAGGATC
CTGGAGGAAC AACCTCTTGT AGGGTCTCGG TTGGAGGAAC CTGCTGAGGC CACAGAACGG TTTCCTGCGG CAGTCTCGGC AGTTCCCTAG
          640        650        660        670        680        690        700        710        720

CTTGAATTC        SEQ. ID NO: 24
GAACTTAAG        SEQ. ID NO: 25
          730
```

FIG.4A

```
AAGCTTTTGG ATCCGCCTTG TTGCCATGTA TCATCGTCCA CGACCCAAAC TTGAACAACT CCGACAAGAT GAAGTTCAAC ACCTACTACT
TTCGAAAACC TAGGCGGAAC AACGGTACAT AGTAGCAGGT GCTGGGTTTG AACTTGTTGA GGCTGTTCTA CTTCAAGTTG TGGATGATGA
           10         20         30         40         50         60         70         80         90

TGTTGGAGTA CAAGGAGTAC TGGCACCAGT TGTGGTCCCA GATCATCCCA GCCACCAGA  CCGTCAAGAT CCAGGAGAGA ACCGGTATCT
ACAACCTCAT GTTCCTCATG ACCGTGGTCA ACACCAGGGT CTAGTAGGGT CGGTGGTCT  GGCAGTTCTA GGTCCTCTCT TGGCCATAGA
          100        110        120        130        140        150        160        170        180

CCGAGGTCGT CCAGAACTCC ATGATCGAGG ACTTGAACAT GTACATCGGT GCCGACTTCG GTATGTTGTT CTACTTCAGA TCCTCCGGTT
GGCTCCAGCA GGTCTTGAGG TACTAGCTCC TGAACTTGTA CATGTAGCCA CGGCTGAAGC CATACAACAA GATGAAGTCT AGGAGGCCAA
          190        200        210        220        230        240        250        260        270

TCAAGGAGCA GATCACCAGA GGTTTGAACA GACCATTGTC CCAGACCACC ACCCAGTTGG GTGAGAGAGT CGAGGAGATG GAGTACTACA
AGTTCCTCGT CTAGTGGTCT CCAAACTTGT CTGGTAACAG GGTCTGGTGG TGGGTCAACC CACTCTCTCA GCTCCTCTAC CTCATGATGT
          280        290        300        310        320        330        340        350        360

ACTCCAACGA CTTGGACGTC AGATACGTCA AGTACGCCTT GGCCAGAGAG TTCACCTTGA AGAGAGTCAA CGGTGAGATC GTCAAGAACT
TGAGGTTGCT GAACCTGCAG TCTATGCAGT TCATGCGGAA CCGGTCTCTC AAGTGGAACT TCTCTCAGTT GCCACTCTAG CAGTTCTTGA
          370        380        390        400        410        420        430        440        450

GGGTCGCCGT CGACTACAGA TTGGCCGGTA AACCGGCCAT CCCAAACGCC CCAATCACCA ACCCATTGAC CTTGACCAAG CACACCATCA
CCCAGCGGCA GCTGATGTCT AACCGGCCAT TTGGCCGGTA GGGTTTGCGG GGTTAGTGGT TGGGTAACTG GAACTGGTTC GTGTGGTAGT
          460        470        480        490        500        510        520        530        540

TCAGATGTGA GAACTCCTAC GACGGTCACA TCTTCAAGAC CCCATTGATC TTCAAGAACG GTGAGGTCAT TTCAAGAACC AACGAGGAGT
AGTCTACACT CTTGAGGATG CTGCCAGTGT AGAAGTTCTG GGGTAACTAG AAGTTCTTGC CACTCCAGTA AAGTTCTTGG TTGCTCCTCA
          550        560        570        580        590        600        610        620        630

TGATCCCAAA GATCAACCAG TGAGAATTC   SEQ. ID NO: 26
ACTAGGGTTT CTAGTTGGTC ACTCTTAAG   SEQ. ID NO: 27
          640        650        660
```

FIG. 4B

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
GATAAGAGTA   CTTCCTATTA   TTGATTTCAC                                   30
```

( 2 ) INFORMATION FOR SEQ ID NO:2:

( i ) SEQUENCE CHARACTERISTICS:
        ( A ) LENGTH: 67 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

```
GGATCTATAC   CCGGGAGTAC   ACTAACACTG   AGAATTTTTC   AGTCAGATAC   ACTGGTTACG      60
TCTTGGC                                                                          67
```

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

```
CACTAACACT   GAGAACTTCC   CAGTCAGATA   CACTG                           35
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

TGAGAACTTC CCAGTCAG                                                                                          18

( 2 ) INFORMATION FOR SEQ ID NO:5:

( i ) SEQUENCE CHARACTERISTICS:
        ( A ) LENGTH: 1113 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..1111

( x i ) SEQUENCE DESCRIPTION: SEQ ID NO:5:

```
ATG  AGA  AAT  TTG  GAT  TTT  ATT  GAT  TCT  TTT  ATA  CCC  ACA  GAA  GGA  AAG       48
Met  Arg  Asn  Leu  Asp  Phe  Ile  Asp  Ser  Phe  Ile  Pro  Thr  Glu  Gly  Lys
 1                    5                    10                        15

TAC  ATT  CGC  GTT  ATG  GAT  TTT  TAT  AAT  AGC  GAG  TAT  CCT  TTC  TGT  ATA       96
Tyr  Ile  Arg  Val  Met  Asp  Phe  Tyr  Asn  Ser  Glu  Tyr  Pro  Phe  Cys  Ile
                20                        25                        30

CAT  GCA  CCC  TCA  GCC  CCT  AAT  GGG  GAT  ATC  ATG  ACA  GAA  ATC  TGT  AGC      144
His  Ala  Pro  Ser  Ala  Pro  Asn  Gly  Asp  Ile  Met  Thr  Glu  Ile  Cys  Ser
           35                        40                        45

AGA  GAA  AAT  AAT  CAA  TAT  TTT  ATT  TTT  TTT  CCT  ACT  GAT  GAT  GGT  CGA      192
Arg  Glu  Asn  Asn  Gln  Tyr  Phe  Ile  Phe  Phe  Pro  Thr  Asp  Asp  Gly  Arg
      50                        55                        60

GTA  ATT  ATT  GCA  AAT  AGG  CAT  AAT  GGG  TCC  GTT  TTT  ACC  GGA  GAA  GCC      240
Val  Ile  Ile  Ala  Asn  Arg  His  Asn  Gly  Ser  Val  Phe  Thr  Gly  Glu  Ala
 65                        70                        75                        80

ACA  AGT  GTA  GTA  TCA  GAT  ATC  TAT  ACT  GGT  AGC  CCA  TTA  CAG  TTT  TTT      288
Thr  Ser  Val  Val  Ser  Asp  Ile  Tyr  Thr  Gly  Ser  Pro  Leu  Gln  Phe  Phe
                     85                        90                        95

AGA  GAG  GTC  AAA  AGA  ACT  ATG  GCA  ACT  TAT  TAT  TTA  GCG  ATA  CAA  AAT      336
Arg  Glu  Val  Lys  Arg  Thr  Met  Ala  Thr  Tyr  Tyr  Leu  Ala  Ile  Gln  Asn
               100                       105                       110

CCT  GAA  TCC  GCA  ACA  GAT  GTG  AGA  GCT  CTA  GAA  CCG  CAT  TCC  CAT  GAG      384
Pro  Glu  Ser  Ala  Thr  Asp  Val  Arg  Ala  Leu  Glu  Pro  His  Ser  His  Glu
          115                       120                       125

CTG  CCA  TCT  CGC  CTT  TAT  TAC  ACT  AAC  AAT  ATT  GAA  AAT  AAT  AGC  AAC      432
Leu  Pro  Ser  Arg  Leu  Tyr  Tyr  Thr  Asn  Asn  Ile  Glu  Asn  Asn  Ser  Asn
     130                       135                       140

ATA  TTA  ATT  TCT  AAT  AAG  GAA  CAA  ATA  TAT  TTA  ACC  TTG  CCT  TCA  CTT      480
Ile  Leu  Ile  Ser  Asn  Lys  Glu  Gln  Ile  Tyr  Leu  Thr  Leu  Pro  Ser  Leu
145                       150                       155                      160

CCA  GAA  AAC  GAG  CAA  TAC  CCT  AAA  ACT  CCA  GTA  TTA  AGC  GGT  ATC  GAT      528
Pro  Glu  Asn  Glu  Gln  Tyr  Pro  Lys  Thr  Pro  Val  Leu  Ser  Gly  Ile  Asp
               165                       170                       175

GAT  ATA  GGA  CCT  AAT  CAA  TCA  GAG  AAA  TCA  ATA  ATA  GGA  AGT  ACT  CTT      576
Asp  Ile  Gly  Pro  Asn  Gln  Ser  Glu  Lys  Ser  Ile  Ile  Gly  Ser  Thr  Leu
          180                       185                       190

ATC  CCA  TGT  ATA  ATG  GTT  TCG  GAT  TTT  ATT  AGT  TTG  GGG  GAG  AGA  ATG      624
Ile  Pro  Cys  Ile  Met  Val  Ser  Asp  Phe  Ile  Ser  Leu  Gly  Glu  Arg  Met
          195                       200                       205

AAA  ACC  ACT  CCA  TAT  TAT  TAT  GTA  AAG  CAC  ACT  CAA  TAT  TGG  CAA  AGC      672
Lys  Thr  Thr  Pro  Tyr  Tyr  Tyr  Val  Lys  His  Thr  Gln  Tyr  Trp  Gln  Ser
210                       215                       220
```

```
ATG TGG TCC GCG CTC TTT CCA CCC GGC TCT AAA GAG ACA AAA ACT GAG    720
Met Trp Ser Ala Leu Phe Pro Pro Gly Ser Lys Glu Thr Lys Thr Glu
225             230             235             240

AAA TCA GGT ATC ACT GAC ACT TCT CAA ATA AGT ATG ACT GAC GGG ATT    768
Lys Ser Gly Ile Thr Asp Thr Ser Gln Ile Ser Met Thr Asp Gly Ile
                245             250             255

AAT GTT TCA ATC GGA GCA GAT TTC GGA TTA AGG TTT GGA AAT AAA ACG    816
Asn Val Ser Ile Gly Ala Asp Phe Gly Leu Arg Phe Gly Asn Lys Thr
            260             265             270

TTT GGA ATT AAG GGG GGG TTC ACC TAT GAT ACA AAG ACT CAA ATA ACT    864
Phe Gly Ile Lys Gly Gly Phe Thr Tyr Asp Thr Lys Thr Gln Ile Thr
        275             280             285

AAT ACC TCC CAA TTG TTA ATA GAA ACA ACT TAT ACT AGA GAA TAC ACA    912
Asn Thr Ser Gln Leu Leu Ile Glu Thr Thr Tyr Thr Arg Glu Tyr Thr
290             295             300

AAT ACA GAA AAT TTT CCT GTT AGA TAT ACA GGC TAT GTT TTA GCG TCA    960
Asn Thr Glu Asn Phe Pro Val Arg Tyr Thr Gly Tyr Val Leu Ala Ser
305             310             315             320

GAA TTT ACT TTA CAT CGT AGT GAT GGA ACT CAG GTT AAT ACG ATC CCA    1008
Glu Phe Thr Leu His Arg Ser Asp Gly Thr Gln Val Asn Thr Ile Pro
                325             330             335

TGG GTT GCT TTA AAC GAT AAC TAT ACA ACA ATA GCA AGA TAT CCA CAT    1056
Trp Val Ala Leu Asn Asp Asn Tyr Thr Thr Ile Ala Arg Tyr Pro His
            340             345             350

TTT GCA AGT GAA CCT TTA CTA GGA AAT ACA AAG ATT ATT ACA GAT GAT    1104
Phe Ala Ser Glu Pro Leu Leu Gly Asn Thr Lys Ile Ile Thr Asp Asp
        355             360             365

CAA AAC T AA                                                       1113
Gln Asn
370
```

( 2 ) INFORMATION FOR SEQ ID NO:6:

( i ) SEQUENCE CHARACTERISTICS:
        ( A ) LENGTH: 370 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Arg Asn Leu Asp Phe Ile Asp Ser Phe Ile Pro Thr Glu Gly Lys
1               5               10              15

Tyr Ile Arg Val Met Asp Phe Tyr Asn Ser Glu Tyr Pro Phe Cys Ile
            20              25              30

His Ala Pro Ser Ala Pro Asn Gly Asp Ile Met Thr Glu Ile Cys Ser
        35              40              45

Arg Glu Asn Asn Gln Tyr Phe Ile Phe Pro Thr Asp Asp Gly Arg
    50              55              60

Val Ile Ile Ala Asn Arg His Asn Gly Ser Val Phe Thr Gly Glu Ala
65              70              75              80

Thr Ser Val Val Ser Asp Ile Tyr Thr Gly Ser Pro Leu Gln Phe Phe
            85              90              95

Arg Glu Val Lys Arg Thr Met Ala Thr Tyr Tyr Leu Ala Ile Gln Asn
        100             105             110

Pro Glu Ser Ala Thr Asp Val Arg Ala Leu Glu Pro His Ser His Glu
    115             120             125

Leu Pro Ser Arg Leu Tyr Tyr Thr Asn Asn Ile Glu Asn Asn Ser Asn
130             135             140

Ile Leu Ile Ser Asn Lys Glu Gln Ile Tyr Leu Thr Leu Pro Ser Leu
```

```
145                     150                     155                     160
Pro  Glu  Asn  Glu  Gln  Tyr  Pro  Lys  Thr  Pro  Val  Leu  Ser  Gly  Ile  Asp
                         165                     170                     175

Asp  Ile  Gly  Pro  Asn  Gln  Ser  Glu  Lys  Ser  Ile  Ile  Gly  Ser  Thr  Leu
               180                      185                     190

Ile  Pro  Cys  Ile  Met  Val  Ser  Asp  Phe  Ile  Ser  Leu  Gly  Glu  Arg  Met
               195                      200                     205

Lys  Thr  Thr  Pro  Tyr  Tyr  Tyr  Val  Lys  His  Thr  Gln  Tyr  Trp  Gln  Ser
     210                      215                     220

Met  Trp  Ser  Ala  Leu  Phe  Pro  Pro  Gly  Ser  Lys  Glu  Thr  Lys  Thr  Glu
225                      230                     235                     240

Lys  Ser  Gly  Ile  Thr  Asp  Thr  Ser  Gln  Ile  Ser  Met  Thr  Asp  Gly  Ile
                    245                     250                     255

Asn  Val  Ser  Ile  Gly  Ala  Asp  Phe  Gly  Leu  Arg  Phe  Gly  Asn  Lys  Thr
               260                      265                     270

Phe  Gly  Ile  Lys  Gly  Gly  Phe  Thr  Tyr  Asp  Thr  Lys  Thr  Gln  Ile  Thr
          275                      280                     285

Asn  Thr  Ser  Gln  Leu  Leu  Ile  Glu  Thr  Thr  Tyr  Thr  Arg  Glu  Tyr  Thr
     290                      295                     300

Asn  Thr  Glu  Asn  Phe  Pro  Val  Arg  Tyr  Thr  Gly  Tyr  Val  Leu  Ala  Ser
305                      310                     315                     320

Glu  Phe  Thr  Leu  His  Arg  Ser  Asp  Gly  Thr  Gln  Val  Asn  Thr  Ile  Pro
                    325                     330                     335

Trp  Val  Ala  Leu  Asn  Asp  Asn  Tyr  Thr  Ile  Ala  Arg  Tyr  Pro  His
                    340                     345                     350

Phe  Ala  Ser  Glu  Pro  Leu  Leu  Gly  Asn  Thr  Lys  Ile  Ile  Thr  Asp  Asp
               355                      360                     365

Gln  Asn
     370
```

( 2 ) INFORMATION FOR SEQ ID NO:7:

( i ) SEQUENCE CHARACTERISTICS:
        ( A ) LENGTH: 1113 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..1111

( x i ) SEQUENCE DESCRIPTION: SEQ ID NO:7:

```
ATG  AGA  AAC  TTG  GAC  TTC  ATC  GAC  TCC  TTC  ATC  CCA  ACT  GAG  GGT  AAG      48
Met  Arg  Asn  Leu  Asp  Phe  Ile  Asp  Ser  Phe  Ile  Pro  Thr  Glu  Gly  Lys
 1                    5                    10                       15

TAC  ATC  AGA  GTC  ATG  GAC  TTC  TAC  AAC  TCC  GAG  TAC  CCA  TTC  TGT  ATC      96
Tyr  Ile  Arg  Val  Met  Asp  Phe  Tyr  Asn  Ser  Glu  Tyr  Pro  Phe  Cys  Ile
               20                        25                       30

CAC  GCT  CCA  TCC  GCT  CCA  AAC  GGT  GAC  ATC  ATG  ACT  GAA  ATC  TGT  TCC     144
His  Ala  Pro  Ser  Ala  Pro  Asn  Gly  Asp  Ile  Met  Thr  Glu  Ile  Cys  Ser
          35                        40                       45

AGA  GAG  AAC  AAC  CAG  TAC  TTC  ATC  TTC  TTC  CCA  ACT  GAC  GAC  GGT  AGA     192
Arg  Glu  Asn  Asn  Gln  Tyr  Phe  Ile  Phe  Phe  Pro  Thr  Asp  Asp  Gly  Arg
     50                        55                       60

GTC  ATC  ATC  GCT  AAC  AGA  CAC  AAC  GGT  TCC  GTC  TTC  ACT  GGT  GAG  GCT     240
Val  Ile  Ile  Ala  Asn  Arg  His  Asn  Gly  Ser  Val  Phe  Thr  Gly  Glu  Ala
 65                       70                       75                       80
```

| | | | | | | | | | | | | | | | | |
|---|---|---|---|---|---|---|---|---|---|---|---|---|---|---|---|---|
| ACT | TCC | GTC | GTC | TCC | GAC | ATC | TAC | ACT | GGT | TCC | CCA | CTG | CAG | TTC | TTC | 288 |
| Thr | Ser | Val | Val | Ser | Asp | Ile | Tyr | Thr | Gly | Ser | Pro | Leu | Gln | Phe | Phe | |
| | | | | 85 | | | | 90 | | | | | | 95 | | |
| AGA | GAG | GTC | AAG | AGA | ACT | ATG | GCT | ACT | TAC | TAC | TTG | GCT | ATC | CAG | AAC | 336 |
| Arg | Glu | Val | Lys | Arg | Thr | Met | Ala | Thr | Tyr | Tyr | Leu | Ala | Ile | Gln | Asn | |
| | | | 100 | | | | | 105 | | | | | 110 | | | |
| CCA | GAG | TCC | GCT | ACT | GAC | GTC | AGA | GCT | TTG | GAG | CCA | CAC | TCC | CAC | GAG | 384 |
| Pro | Glu | Ser | Ala | Thr | Asp | Val | Arg | Ala | Leu | Glu | Pro | His | Ser | His | Glu | |
| | | 115 | | | | | 120 | | | | | 125 | | | | |
| TTG | CCA | TCC | AGA | TTG | TAC | TAC | ACT | AAC | AAC | ATC | GAG | AAC | AAC | TCC | AAC | 432 |
| Leu | Pro | Ser | Arg | Leu | Tyr | Tyr | Thr | Asn | Asn | Ile | Glu | Asn | Asn | Ser | Asn | |
| | 130 | | | | | 135 | | | | | 140 | | | | | |
| ATC | TTG | ATC | TCC | AAC | AAG | GAG | CAG | ATT | TAC | TTG | ACT | TTG | CCA | TCC | TTG | 480 |
| Ile | Leu | Ile | Ser | Asn | Lys | Glu | Gln | Ile | Tyr | Leu | Thr | Leu | Pro | Ser | Leu | |
| 145 | | | | | 150 | | | | | 155 | | | | | 160 | |
| CCA | GAG | AAC | GAG | CAG | TAC | CCA | AAG | ACT | CCA | GTC | TTG | TCC | GGT | ATC | GAC | 528 |
| Pro | Glu | Asn | Glu | Gln | Tyr | Pro | Lys | Thr | Pro | Val | Leu | Ser | Gly | Ile | Asp | |
| | | | | 165 | | | | | 170 | | | | | 175 | | |
| GAC | ATC | GGT | CCA | AAC | CAG | TCC | GAG | AAG | TCC | ATC | ATC | GGT | TCC | ACT | TGG | 576 |
| Asp | Ile | Gly | Pro | Asn | Gln | Ser | Glu | Lys | Ser | Ile | Ile | Gly | Ser | Thr | Trp | |
| | | | 180 | | | | | 185 | | | | | 190 | | | |
| ATC | CCA | TGT | ATC | ATG | GTC | TCC | GAC | TTC | ATC | TCC | TTG | GGT | GAG | AGA | ATG | 624 |
| Ile | Pro | Cys | Ile | Met | Val | Ser | Asp | Phe | Ile | Ser | Leu | Gly | Glu | Arg | Met | |
| | | 195 | | | | | 200 | | | | | 205 | | | | |
| AAG | ACT | ACT | CCA | TAC | TAC | TAC | GTC | AAG | CAC | ACT | CAG | TAC | TGG | CAG | TCC | 672 |
| Lys | Thr | Thr | Pro | Tyr | Tyr | Tyr | Val | Lys | His | Thr | Gln | Tyr | Trp | Gln | Ser | |
| | 210 | | | | | 215 | | | | | 220 | | | | | |
| ATG | TGG | TCC | GCT | TTG | TTC | CCA | CCA | GGT | TCC | AAG | GAG | ACT | AAG | ACT | GAG | 720 |
| Met | Trp | Ser | Ala | Leu | Phe | Pro | Pro | Gly | Ser | Lys | Glu | Thr | Lys | Thr | Glu | |
| 225 | | | | | 230 | | | | | 235 | | | | | 240 | |
| AAG | TCC | GGT | ATC | ACT | GAC | ACT | TCC | CAG | ATT | TCC | ATG | ACT | GAC | GGT | ATC | 768 |
| Lys | Ser | Gly | Ile | Thr | Asp | Thr | Ser | Gln | Ile | Ser | Met | Thr | Asp | Gly | Ile | |
| | | | | 245 | | | | | 250 | | | | | 255 | | |
| AAC | GTC | TCC | ATC | GGT | GCT | GAC | TTC | GGT | TTG | AGA | TTC | GGT | AAC | AAG | ACT | 816 |
| Asn | Val | Ser | Ile | Gly | Ala | Asp | Phe | Gly | Leu | Arg | Phe | Gly | Asn | Lys | Thr | |
| | | | 260 | | | | | 265 | | | | | 270 | | | |
| TTC | GGT | ATC | AAG | GGT | GGT | TTC | ACT | TAC | GAC | ACT | AAG | ACT | CAG | ATC | ACT | 864 |
| Phe | Gly | Ile | Lys | Gly | Gly | Phe | Thr | Tyr | Asp | Thr | Lys | Thr | Gln | Ile | Thr | |
| | | 275 | | | | | 280 | | | | | 285 | | | | |
| AAC | ACT | TCC | CAG | TTG | TTG | ATC | GAG | ACT | ACT | TAC | ACC | CGG | GAG | TAC | ACT | 912 |
| Asn | Thr | Ser | Gln | Leu | Leu | Ile | Glu | Thr | Thr | Tyr | Thr | Arg | Glu | Tyr | Thr | |
| | 290 | | | | | 295 | | | | | 300 | | | | | |
| AAC | ACT | GAG | AAC | TTC | CCA | GTC | AGA | TAC | ACT | GGT | TAC | GTC | TTG | GCT | TCC | 960 |
| Asn | Thr | Glu | Asn | Phe | Pro | Val | Arg | Tyr | Thr | Gly | Tyr | Val | Leu | Ala | Ser | |
| 305 | | | | | 310 | | | | | 315 | | | | | 320 | |
| GAG | TTC | ACT | TTG | CAC | AGA | TCC | GAC | GGT | ACT | CAG | GTC | AAC | ACT | ATC | CCA | 1008 |
| Glu | Phe | Thr | Leu | His | Arg | Ser | Asp | Gly | Thr | Gln | Val | Asn | Thr | Ile | Pro | |
| | | | | 325 | | | | | 330 | | | | | 335 | | |
| TGG | GTC | GCT | TTG | AAC | GAC | AAC | TAC | ACT | ACT | ATC | GCT | AGA | TAC | CCA | CAC | 1056 |
| Trp | Val | Ala | Leu | Asn | Asp | Asn | Tyr | Thr | Thr | Ile | Ala | Arg | Tyr | Pro | His | |
| | | | 340 | | | | | 345 | | | | | 350 | | | |
| TTC | GCT | TCC | GAG | CCA | TTG | TTG | GGT | AAC | ACT | AAG | ATC | ATC | ACT | GAC | GAC | 1104 |
| Phe | Ala | Ser | Glu | Pro | Leu | Leu | Gly | Asn | Thr | Lys | Ile | Ile | Thr | Asp | Asp | |
| | | 355 | | | | | 360 | | | | | 365 | | | | |
| CAG | AAC | T AA | | | | | | | | | | | | | | 1113 |
| Gln | Asn | | | | | | | | | | | | | | | |
| | 370 | | | | | | | | | | | | | | | |

( 2 ) INFORMATION FOR SEQ ID NO:8:

( i ) SEQUENCE CHARACTERISTICS:
  ( A ) LENGTH: 53 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:8:

GTTCTTCAGA GAGGTCAAGA GAACTATGGC TACTTACTAC TTGGCTATCC AGA  53

( 2 ) INFORMATION FOR SEQ ID NO:9:

( i ) SEQUENCE CHARACTERISTICS:
    ( A ) LENGTH: 41 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:9:

ACCCAGAGTC CGCTACTGAC GTCAGAGCTT TGGAGCCACA C  41

( 2 ) INFORMATION FOR SEQ ID NO:10:

( i ) SEQUENCE CHARACTERISTICS:
    ( A ) LENGTH: 40 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:10:

TCCCACGAGT TGCCATCCAG ATTGTACTAC ACTAACAACA  40

( 2 ) INFORMATION FOR SEQ ID NO:11:

( i ) SEQUENCE CHARACTERISTICS:
    ( A ) LENGTH: 39 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:11:

TCGAGAACAA CTCCAACATC TTGATCTCCA ACAAGGAGC  39

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:12:

AGATTTACTT GACTTTGCCA TCCTTGCCAG AGAACGAGCA  40

( 2 ) INFORMATION FOR SEQ ID NO:13:

( i ) SEQUENCE CHARACTERISTICS:
    ( A ) LENGTH: 40 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:13:

GTACCCAAAG ACTCCAGTCT TGTCCGGTAT CGACGACATC 40

( 2 ) INFORMATION FOR SEQ ID NO:14:

( i ) SEQUENCE CHARACTERISTICS:
        ( A ) LENGTH: 41 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

GGTCCAAACC AGTCCGAGAA GTCCATCATC GGTTCCACTT G 41

( 2 ) INFORMATION FOR SEQ ID NO:15:

( i ) SEQUENCE CHARACTERISTICS:
        ( A ) LENGTH: 54 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

CTGCTGTAGC CAGGTTTGGT CAGGCTCTTC AGGTAGTAGC CAAGGTGAAC CTAG 54

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

TCTTGCTCGT CATGGGTTTC TGAGGTCAGA ACAGGCCATA G 41

( 2 ) INFORMATION FOR SEQ ID NO:17:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

TTGTTCCTCG TCTAAATGAA CTGAAACGGT AGGAACGGTC 40

( 2 ) INFORMATION FOR SEQ ID NO:18:

( i ) SEQUENCE CHARACTERISTICS:
        ( A ) LENGTH: 39 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:18:

TGATTGTTGT AGCTCTTGTT GAGGTTGTAG AACTAGAGG          39

( 2 ) INFORMATION FOR SEQ ID NO:19:

( i ) SEQUENCE CHARACTERISTICS:
        ( A ) LENGTH: 41 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:19:

ACCTCGGTGT GAGGGTGCTC AACGGTAGGT CTAACATGAT G          41

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

CGATAGGTCT TGGGTCTCAG GCGATGACTG CAGTCTCGAA          40

( 2 ) INFORMATION FOR SEQ ID NO:21:

( i ) SEQUENCE CHARACTERISTICS:
        ( A ) LENGTH: 47 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:21:

ACGTCAAGAA GTCTCTCCAG TTCTCTTGAT ACCGATGAAT GATGAAC          47

( 2 ) INFORMATION FOR SEQ ID NO:22:

( i ) SEQUENCE CHARACTERISTICS:
        ( A ) LENGTH: 1366 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 14..1355

( x i ) SEQUENCE DESCRIPTION: SEQ ID NO:22:

```
AAGCTTCGAA ACG ATG TGC GAT TCT AAA GAT AAT TCT GGA GTT TCT GAA          49
            Met Cys Asp Ser Lys Asp Asn Ser Gly Val Ser Glu
            1               5                   10

AAA TGC GGA AAA AAG TTC ACC AAC TAC CCA TTG AAC ACC ACC CCA ACC          97
Lys Cys Gly Lys Lys Phe Thr Asn Tyr Pro Leu Asn Thr Thr Pro Thr
        15                  20                  25

TCC TTG AAC TAC AAC TTG CCA GAG ATC TCC AAG AAG TTC TAC AAC TTG          145
Ser Leu Asn Tyr Asn Leu Pro Glu Ile Ser Lys Lys Phe Tyr Asn Leu
    30                  35                  40

AAG AAC AAG TAC TCC AGA AAC GGT TAC GGT TTG TCC AAG ACC GAG TTC          193
Lys Asn Lys Tyr Ser Arg Asn Gly Tyr Gly Leu Ser Lys Thr Glu Phe
45                  50                  55                  60
```

| | | | | | | | | | | | | | | | | |
|---|---|---|---|---|---|---|---|---|---|---|---|---|---|---|---|---|
| CCA | TCC | TCC | ATC | GAG | AAC | TGT | CCA | TCC | AAC | GAG | TAC | TCC | ATC | ATG | TAC | 241 |
| Pro | Ser | Ser | Ile | Glu | Asn | Cys | Pro | Ser | Asn | Glu | Tyr | Ser | Ile | Met | Tyr | |
| | | | | 65 | | | | 70 | | | | | | 75 | | |
| GAC | AAC | AAG | GAC | CCA | AGA | TTC | TTG | ATC | AGA | TTC | TTG | TTG | GAC | GAC | GGT | 289 |
| Asp | Asn | Lys | Asp | Pro | Arg | Phe | Leu | Ile | Arg | Phe | Leu | Leu | Asp | Asp | Gly | |
| | | | 80 | | | | | 85 | | | | | | 90 | | |
| AGA | TAC | ATC | ATC | GCC | GAC | AGA | GAC | GAC | GGT | GAG | GTC | TTC | GAC | GAG | GCC | 337 |
| Arg | Tyr | Ile | Ile | Ala | Asp | Arg | Asp | Asp | Gly | Glu | Val | Phe | Asp | Glu | Ala | |
| | | | 95 | | | | | 100 | | | | | 105 | | | |
| CCA | ACC | TAC | TTG | GAC | AAC | AAC | AAC | CAC | CCA | ATC | ATC | TCC | AGA | CAC | TAC | 385 |
| Pro | Thr | Tyr | Leu | Asp | Asn | Asn | Asn | His | Pro | Ile | Ile | Ser | Arg | His | Tyr | |
| | 110 | | | | | | 115 | | | | | | 120 | | | |
| ACC | GGT | GAG | GAG | AGA | CAG | AAG | TTC | GAG | CAG | GTC | GGT | TCC | GGT | GAC | TAC | 433 |
| Thr | Gly | Glu | Glu | Arg | Gln | Lys | Phe | Glu | Gln | Val | Gly | Ser | Gly | Asp | Tyr | |
| | 125 | | | | | 130 | | | | | 135 | | | | 140 | |
| ATC | ACC | GGT | GAG | CAG | TTC | TTC | CAG | TTC | TAC | ACC | CAG | AAC | AAG | ACC | AGA | 481 |
| Ile | Thr | Gly | Glu | Gln | Phe | Phe | Gln | Phe | Tyr | Thr | Gln | Asn | Lys | Thr | Arg | |
| | | | | 145 | | | | | 150 | | | | | 155 | | |
| GTC | TTG | TCC | AAC | TGT | AGA | GCC | TTG | GAC | TCC | AGA | ACC | ATC | TTG | TTG | TCC | 529 |
| Val | Leu | Ser | Asn | Cys | Arg | Ala | Leu | Asp | Ser | Arg | Thr | Ile | Leu | Leu | Ser | |
| | | | 160 | | | | | 165 | | | | | 170 | | | |
| ACC | GCC | AAG | ATC | TTC | CCA | ATC | TAC | CCA | CCA | GCC | TCC | GAG | ACC | CAG | TTG | 577 |
| Thr | Ala | Lys | Ile | Phe | Pro | Ile | Tyr | Pro | Pro | Ala | Ser | Glu | Thr | Gln | Leu | |
| | | 175 | | | | | 180 | | | | | 185 | | | | |
| ACC | GCC | TTC | GTC | AAC | TCC | TCC | TTC | TAC | GCC | GCC | GCC | ATC | CCA | CAG | TTG | 625 |
| Thr | Ala | Phe | Val | Asn | Ser | Ser | Phe | Tyr | Ala | Ala | Ala | Ile | Pro | Gln | Leu | |
| | | 190 | | | | | 195 | | | | | 200 | | | | |
| CCA | CAG | ACC | TCC | TTG | TTG | GAG | AAC | ATC | CCA | GAG | CCA | ACC | TCC | TTG | GAC | 673 |
| Pro | Gln | Thr | Ser | Leu | Leu | Glu | Asn | Ile | Pro | Glu | Pro | Thr | Ser | Leu | Asp | |
| 205 | | | | | 210 | | | | | 215 | | | | | 220 | |
| GAC | TCC | GGT | GTC | TTG | CCA | AAG | GAC | GCC | GTC | AGA | GCC | GTC | AAG | GGA | TCC | 721 |
| Asp | Ser | Gly | Val | Leu | Pro | Lys | Asp | Ala | Val | Arg | Ala | Val | Lys | Gly | Ser | |
| | | | | 225 | | | | | 230 | | | | | 235 | | |
| GCC | TTG | TTG | CCA | TGT | ATC | ATC | GTC | CAC | GAC | CCA | AAC | TTG | AAC | AAC | TCC | 769 |
| Ala | Leu | Leu | Pro | Cys | Ile | Ile | Val | His | Asp | Pro | Asn | Leu | Asn | Asn | Ser | |
| | | | 240 | | | | | 245 | | | | | 250 | | | |
| GAC | AAG | ATG | AAG | TTC | AAC | ACC | TAC | TAC | TTG | TTG | GAG | TAC | AAG | GAG | TAC | 817 |
| Asp | Lys | Met | Lys | Phe | Asn | Thr | Tyr | Tyr | Leu | Leu | Glu | Tyr | Lys | Glu | Tyr | |
| | | 255 | | | | | 260 | | | | | 265 | | | | |
| TGG | CAC | CAG | TTG | TGG | TCC | CAG | ATC | ATC | CCA | GCC | CAC | CAG | ACC | GTC | AAG | 865 |
| Trp | His | Gln | Leu | Trp | Ser | Gln | Ile | Ile | Pro | Ala | His | Gln | Thr | Val | Lys | |
| | 270 | | | | | 275 | | | | | 280 | | | | | |
| ATC | CAG | GAG | AGA | ACC | GGT | ATC | TCC | GAG | GTC | GTC | CAG | AAC | TCC | ATG | ATC | 913 |
| Ile | Gln | Glu | Arg | Thr | Gly | Ile | Ser | Glu | Val | Val | Gln | Asn | Ser | Met | Ile | |
| 285 | | | | | 290 | | | | | 295 | | | | | 300 | |
| GAG | GAC | TTG | AAC | ATG | TAC | ATC | GGT | GCC | GAC | TTC | GGT | ATG | TTG | TTC | TAC | 961 |
| Glu | Asp | Leu | Asn | Met | Tyr | Ile | Gly | Ala | Asp | Phe | Gly | Met | Leu | Phe | Tyr | |
| | | | | 305 | | | | | 310 | | | | | 315 | | |
| TTC | AGA | TCC | TCC | GGT | TTC | AAG | GAG | CAG | ATC | ACC | AGA | GGT | TTG | AAC | AGA | 1009 |
| Phe | Arg | Ser | Ser | Gly | Phe | Lys | Glu | Gln | Ile | Thr | Arg | Gly | Leu | Asn | Arg | |
| | | | 320 | | | | | 325 | | | | | 330 | | | |
| CCA | TTG | TCC | CAG | ACC | ACC | ACC | CAG | TTG | GGT | GAG | AGA | GTC | GAG | GAG | ATG | 1057 |
| Pro | Leu | Ser | Gln | Thr | Thr | Thr | Gln | Leu | Gly | Glu | Arg | Val | Glu | Glu | Met | |
| | | 335 | | | | | 340 | | | | | 345 | | | | |
| GAG | TAC | TAC | AAC | TCC | AAC | GAC | TTG | GAC | GTC | AGA | TAC | GTC | AAG | TAC | GCC | 1105 |
| Glu | Tyr | Tyr | Asn | Ser | Asn | Asp | Leu | Asp | Val | Arg | Tyr | Val | Lys | Tyr | Ala | |
| | 350 | | | | | 355 | | | | | 360 | | | | | |
| TTG | GCC | AGA | GAG | TTC | ACC | TTG | AAG | AGA | GTC | AAC | GGT | GAG | ATC | GTC | AAG | 1153 |
| Leu | Ala | Arg | Glu | Phe | Thr | Leu | Lys | Arg | Val | Asn | Gly | Glu | Ile | Val | Lys | |
| 365 | | | | 370 | | | | | 375 | | | | | 380 | | |

-continued

| | | | | | | | | | | | | | | | | |
|---|---|---|---|---|---|---|---|---|---|---|---|---|---|---|---|---|
| AAC | TGG | GTC | GCC | GTC | GAC | TAC | AGA | TTG | GCC | GGT | ATC | CAG | TCC | TAC | CCA | 1201 |
| Asn | Trp | Val | Ala | Val | Asp | Tyr | Arg | Leu | Ala | Gly | Ile | Gln | Ser | Tyr | Pro | |
| | | | 385 | | | | | 390 | | | | | | 395 | | |
| AAC | GCC | CCA | ATC | ACC | AAC | CCA | TTG | ACC | TTG | ACC | AAG | CAC | ACC | ATC | ATC | 1249 |
| Asn | Ala | Pro | Ile | Thr | Asn | Pro | Leu | Thr | Leu | Thr | Lys | His | Thr | Ile | Ile | |
| | | | 400 | | | | | 405 | | | | | 410 | | | |
| AGA | TGT | GAG | AAC | TCC | TAC | GAC | GGT | CAC | ATC | TTC | AAG | ACC | CCA | TTG | ATC | 1297 |
| Arg | Cys | Glu | Asn | Ser | Tyr | Asp | Gly | His | Ile | Phe | Lys | Thr | Pro | Leu | Ile | |
| | | 415 | | | | | 420 | | | | 425 | | | | | |
| TTC | AAG | AAC | GGT | GAG | GTC | ATC | GTC | AAG | ACC | AAC | GAG | GAG | TTG | ATC | CCA | 1345 |
| Phe | Lys | Asn | Gly | Glu | Val | Ile | Val | Lys | Thr | Asn | Glu | Glu | Leu | Ile | Pro | |
| | 430 | | | | | 435 | | | | | 440 | | | | | |
| AAG | ATC | AAC | CAG | TGA | GAA | TTC | | | | | | | | | | 1366 |
| Lys | Ile | Asn | Gln | | | | | | | | | | | | | |
| 445 | | | | | | | | | | | | | | | | |

( 2 ) INFORMATION FOR SEQ ID NO:23:

( i ) SEQUENCE CHARACTERISTICS:
        ( A ) LENGTH: 448 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Met | Cys | Asp | Ser | Lys | Asp | Asn | Ser | Gly | Val | Ser | Glu | Lys | Cys | Gly | Lys |
| 1 | | | | 5 | | | | | 10 | | | | | 15 |
| Lys | Phe | Thr | Asn | Tyr | Pro | Leu | Asn | Thr | Thr | Pro | Thr | Ser | Leu | Asn | Tyr |
| | | | | 20 | | | | | 25 | | | | | 30 | |
| Asn | Leu | Pro | Glu | Ile | Ser | Lys | Lys | Phe | Tyr | Asn | Leu | Lys | Asn | Lys | Tyr |
| | | | 35 | | | | | 40 | | | | | 45 | | |
| Ser | Arg | Asn | Gly | Tyr | Gly | Leu | Ser | Lys | Thr | Glu | Phe | Pro | Ser | Ser | Ile |
| | | 50 | | | | | 55 | | | | | 60 | | | |
| Glu | Asn | Cys | Pro | Ser | Asn | Glu | Tyr | Ser | Ile | Met | Tyr | Asp | Asn | Lys | Asp |
| 65 | | | | | 70 | | | | | 75 | | | | | 80 |
| Pro | Arg | Phe | Leu | Ile | Arg | Phe | Leu | Leu | Asp | Asp | Gly | Arg | Tyr | Ile | Ile |
| | | | | 85 | | | | | 90 | | | | | 95 | |
| Ala | Asp | Arg | Asp | Asp | Gly | Glu | Val | Phe | Asp | Glu | Ala | Pro | Thr | Tyr | Leu |
| | | | 100 | | | | | 105 | | | | | 110 | | |
| Asp | Asn | Asn | Asn | His | Pro | Ile | Ile | Ser | Arg | His | Tyr | Thr | Gly | Glu | Glu |
| | | | 115 | | | | | 120 | | | | | 125 | | |
| Arg | Gln | Lys | Phe | Glu | Gln | Val | Gly | Ser | Gly | Asp | Tyr | Ile | Thr | Gly | Glu |
| | | 130 | | | | | 135 | | | | | 140 | | | |
| Gln | Phe | Phe | Gln | Phe | Tyr | Thr | Gln | Asn | Lys | Thr | Arg | Val | Leu | Ser | Asn |
| 145 | | | | | 150 | | | | | 155 | | | | | 160 |
| Cys | Arg | Ala | Leu | Asp | Ser | Arg | Thr | Ile | Leu | Leu | Ser | Thr | Ala | Lys | Ile |
| | | | | 165 | | | | | 170 | | | | | 175 | |
| Phe | Pro | Ile | Tyr | Pro | Pro | Ala | Ser | Glu | Thr | Gln | Leu | Thr | Ala | Phe | Val |
| | | | 180 | | | | | 185 | | | | | 190 | | |
| Asn | Ser | Ser | Phe | Tyr | Ala | Ala | Ala | Ile | Pro | Gln | Leu | Pro | Gln | Thr | Ser |
| | | | 195 | | | | | 200 | | | | | 205 | | |
| Leu | Leu | Glu | Asn | Ile | Pro | Glu | Pro | Thr | Ser | Leu | Asp | Asp | Ser | Gly | Val |
| | | | 210 | | | | | 215 | | | | | 220 | | |
| Leu | Pro | Lys | Asp | Ala | Val | Arg | Ala | Val | Lys | Gly | Ser | Ala | Leu | Leu | Pro |
| 225 | | | | | 230 | | | | | 235 | | | | | 240 |
| Cys | Ile | Ile | Val | His | Asp | Pro | Asn | Leu | Asn | Asn | Ser | Asp | Lys | Met | Lys |
| | | | | 245 | | | | | 250 | | | | | 255 | |

| Phe | Asn | Thr | Tyr<br>260 | Tyr | Leu | Leu | Glu | Tyr<br>265 | Lys | Glu | Tyr | Trp | His<br>270 | Gln | Leu |
|---|---|---|---|---|---|---|---|---|---|---|---|---|---|---|---|
| Trp | Ser | Gln<br>275 | Ile | Ile | Pro | Ala | His<br>280 | Gln | Thr | Val | Lys | Ile<br>285 | Gln | Glu | Arg |
| Thr | Gly<br>290 | Ile | Ser | Glu | Val | Val<br>295 | Gln | Asn | Ser | Met | Ile<br>300 | Glu | Asp | Leu | Asn |
| Met<br>305 | Tyr | Ile | Gly | Ala | Asp<br>310 | Phe | Gly | Met | Leu | Phe<br>315 | Tyr | Phe | Arg | Ser | Ser<br>320 |
| Gly | Phe | Lys | Glu | Gln<br>325 | Ile | Thr | Arg | Gly | Leu<br>330 | Asn | Arg | Pro | Leu | Ser<br>335 | Gln |
| Thr | Thr | Thr | Gln<br>340 | Leu | Gly | Glu | Arg | Val<br>345 | Glu | Glu | Met | Glu | Tyr<br>350 | Tyr | Asn |
| Ser | Asn | Asp<br>355 | Leu | Asp | Val | Arg | Tyr<br>360 | Val | Lys | Tyr | Ala | Leu<br>365 | Ala | Arg | Glu |
| Phe | Thr<br>370 | Leu | Lys | Arg | Val | Asn<br>375 | Gly | Glu | Ile | Val | Lys<br>380 | Asn | Trp | Val | Ala |
| Val<br>385 | Asp | Tyr | Arg | Leu | Ala<br>390 | Gly | Ile | Gln | Ser | Tyr<br>395 | Pro | Asn | Ala | Pro | Ile<br>400 |
| Thr | Asn | Pro | Leu | Thr<br>405 | Leu | Thr | Lys | His | Thr<br>410 | Ile | Ile | Arg | Cys | Glu<br>415 | Asn |
| Ser | Tyr | Asp | Gly<br>420 | His | Ile | Phe | Lys | Thr<br>425 | Pro | Leu | Ile | Phe | Lys<br>430 | Asn | Gly |
| Glu | Val | Ile<br>435 | Val | Lys | Thr | Asn | Glu<br>440 | Glu | Leu | Ile | Pro | Lys<br>445 | Ile | Asn | Gln |

( 2 ) INFORMATION FOR SEQ ID NO:24:

( i ) SEQUENCE CHARACTERISTICS:
        ( A ) LENGTH: 729 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:24:

| | | | | | |
|---|---|---|---|---|---|
| AAGCTTCGAA | ACGATGTGCG | ATTCTAAAGA | TAATTCTGGA | GTTTCTGAAA | AATGCGGAAA | 60 |
| AAAGTTCACC | AACTACCCAT | TGAACACCAC | CCCAACCTCC | TTGAACTACA | ACTTGCCAGA | 120 |
| GATCTCCAAG | AAGTTCTACA | ACTTGAAGAA | CAAGTACTCC | AGAAACGGTT | ACGGTTTGTC | 180 |
| CAAGACCGAG | TTCCCATCCT | CCATCGAGAA | CTGTCCATCC | AACGAGTACT | CCATCATGTA | 240 |
| CGACAACAAG | GACCCAAGAT | TCTTGATCAG | ATTCTTGTTG | GACGACGGTA | GATACATCAT | 300 |
| CGCCGACAGA | GACGACGGTG | AGGTCTTCGA | CGAGGCCCCA | ACCTACTTGG | ACAACAACAA | 360 |
| CCACCCAATC | ATCTCCAGAC | ACTACACCGG | TGAGGAGAGA | CAGAAGTTCG | AGCAGGTCGG | 420 |
| TTCCGGTGAC | TACATCACCG | GTGAGCAGTT | CTTCCAGTTC | TACACCCAGA | ACAAGACCAG | 480 |
| AGTCTTGTCC | AACTGTAGAG | CCTTGGACTC | CAGAACCATC | TTGTTGTCCA | CCGCCAAGAT | 540 |
| CTTCCCAATC | TACCCACCAG | CCTCCGAGAC | CCAGTTGACC | GCCTTCGTCA | ACTCCTCCTT | 600 |
| CTACGCCGCC | GCCATCCCAC | AGTTGCCACA | GACCTCCTTG | TTGGAGAACA | TCCCAGAGCC | 660 |
| AACCTCCTTG | GACGACTCCG | GTGTCTTGCC | AAAGGACGCC | GTCAGAGCCG | TCAAGGGATC | 720 |
| CTTGAATTC | | | | | | 729 |

( 2 ) INFORMATION FOR SEQ ID NO:25:

( i ) SEQUENCE CHARACTERISTICS:
        ( A ) LENGTH: 729 base pairs ( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:25:

| | | | | | | |
|---|---|---|---|---|---|---|
| GAATTCAAGG | ATCCCTTGAC | GGCTCTGACG | GCGTCCTTTG | GCAAGACACC | GGAGTCGTCC | 60 |
| AAGGAGGTTG | GCTCTGGGAT | GTTCTCCAAC | AAGGAGGTCT | GTGGCAACTG | TGGGATGGCG | 120 |
| GCGGCGTAGA | AGGAGGAGTT | GACGAAGGCG | GTCAACTGGG | TCTCGGAGGC | TGGTGGGTAG | 180 |
| ATTGGGAAGA | TCTTGGCGGT | GGACAACAAG | ATGGTTCTGG | AGTCCAAGGC | TCTACAGTTG | 240 |
| GACAAGACTC | TGGTCTTGTT | CTGGGTGTAG | AACTGGAAGA | ACTGCTCACC | GGTGATGTAG | 300 |
| TCACCGGAAC | CGACCTGCTC | GAACTTCTGT | CTCTCCTCAC | CGGTGTAGTG | TCTGGAGATG | 360 |
| ATTGGGTGGT | TGTTGTTGTC | CAAGTAGGTT | GGGGCCTCGT | CGAAGACCTC | ACCGTCGTCT | 420 |
| CTGTCGGCGA | TGATGTATCT | ACCGTCGTCC | AACAAGAATC | TGATCAAGAA | TCTTGGGTCC | 480 |
| TTGTTGTCGT | ACATGATGGA | GTACTCGTTG | GATGGACAGT | TCTCGATGGA | GGATGGGAAC | 540 |
| TCGGTCTTGG | ACAAACCGTA | ACCGTTTCTG | GAGTACTTGT | TCTTCAAGTT | GTAGAACTTC | 600 |
| TTGGAGATCT | CTGGCAAGTT | GTAGTTCAAG | GAGGTTGGGG | TGGTGTTCAA | TGGGTAGTTG | 660 |
| GTGAACTTTT | TTCCGCATTT | TTCAGAAACT | CCAGAATTAT | CTTTAGAATC | GCACATCGTT | 720 |
| TCGAAGCTT | | | | | | 729 |

( 2 ) INFORMATION FOR SEQ ID NO:26:

( i ) SEQUENCE CHARACTERISTICS:
( A ) LENGTH: 659 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:26:

| | | | | | | |
|---|---|---|---|---|---|---|
| AAGCTTTTGG | ATCCGCCTTG | TTGCCATGTA | TCATCGTCCA | CGACCCAAAC | TTGAACAACT | 60 |
| CCGACAAGAT | GAAGTTCAAC | ACCTACTACT | TGTTGGAGTA | CAAGGAGTAC | TGGCACCAGT | 120 |
| TGTGGTCCCA | GATCATCCCA | GCCCACCAGA | CCGTCAAGAT | CCAGGAGAGA | ACCGGTATCT | 180 |
| CCGAGGTCGT | CCAGAACTCC | ATGATCGAGG | ACTTGAACAT | GTACATCGGT | GCCGACTTCG | 240 |
| GTATGTTGTT | CTACTTCAGA | TCCTCCGGTT | TCAAGGAGCA | GATCACCAGA | GGTTTGAACA | 300 |
| GACCATTGTC | CCAGACCACC | ACCCAGTTGG | GTGAGAGAGT | CGAGGAGATG | GAGTACTACA | 360 |
| ACTCCAACGA | CTTGGACGTC | AGATACGTCA | AGTACGCCTT | GGCCAGAGAG | TTCACCTTGA | 420 |
| AGAGAGTCAA | CGGTGAGATC | GTCAAGAACT | GGGTCGCCGT | CGACTACAGA | TTGGCCGGTA | 480 |
| TCCAGTCCTA | CCCAAACGCC | CCAATCACCA | ACCCATTGAC | CTTGACCAAG | CACACCATCA | 540 |
| TCAGATGTGA | GAACTCCTAC | GACGGTCACA | TCTTCAAGAC | CCCATTGATC | TTCAAGAACG | 600 |
| GTGAGGTCAT | CGTCAAGACC | AACGAGGAGT | TGATCCCAAA | GATCAACCAG | TGAGAATTC | 659 |

( 2 ) INFORMATION FOR SEQ ID NO:27:

( i ) SEQUENCE CHARACTERISTICS:
( A ) LENGTH: 659 base pairs
( B ) TYPE: nucleic acid
( C ) STRANDEDNESS: unknown
( D ) TOPOLOGY: unknown ( i i ) MOLECULE TYPE: DNA (genomic)

-continued ( x i ) SEQUENCE DESCRIPTION: SEQ ID NO:27:

```
GAATTCTCAC  TGGTTGATCT  TTGGGATCAA  CTCCTCGTTG  GTCTTGACGA  TGACCTCACC     60
GTTCTTGAAG  ATCAATGGGG  TCTTGAAGAT  GTGACCGTCG  TAGGAGTTCT  CACATCTGAT    120
GATGGTGTGC  TTGGTCAAGG  TCAATGGGTT  GGTGATTGGG  GCGTTTGGGT  AGGACTGGAT    180
ACCGGCCAAT  CTGTAGTCGA  CGGCGACCCA  GTTCTTGACG  ATCTCACCGT  TGACTCTCTT    240
CAAGGTGAAC  TCTCTGGCCA  AGGCGTACTT  GACGTATCTG  ACGTCCAAGT  CGTTGGAGTT    300
GTAGTACTCC  ATCTCCTCGA  CTCTCTCACC  CAACTGGGTG  GTGGTCTGGG  ACAATGGCTT    360
GTTCAAACCT  CTGGTGATCT  GCTCCTTGAA  ACCGGAGGAT  CTGAAGTAGA  ACAACATACC    420
GAAGTCGGCA  CCGATGTACA  TGTTCAAGTC  CTCGATCATG  GAGTTCTGGA  CGACCTCGGA    480
GATACCGGTT  CTCTCCTGGA  TCTTGACGGT  CTGGTGGGCT  GGGATGATCT  GGGACCACAA    540
CTGGTGCCAG  TACTCCTTGT  ACTCCAACAA  GTAGTAGGTG  TTGAACTTCA  TCTTGTCGGA    600
GTTGTTCAAG  TTTGGGTCGT  GGACGATGAT  ACATGGCAAC  AAGGCGGATC  CAAAAGCTT     659
```

PRODUCTION OF BACILLUS ENTOMOTOXINS IN METHYLOTROPHIC YEAST

This is a continuation of application Ser. No. 926,448 filed on Aug. 7, 1992 now abandoned.

TECHNICAL FIELD

The present invention relates generally to a novel microbiological process for producing insecticidal toxins using recombinant DNA technology and more particularly to the production in methylotrophic yeast cells, especially those of the species *Pichia pastoris*, of larvicidal toxin polypeptides which are indigenous to entomocidal Bacillus species and strains.

BACKGROUND OF THE INVENTION

Chemical pesticides have long been used to control spread of infectious diseases by insects harboring pathogens. Disadvantageously, many such pesticides have potential or recognized environmental and health hazards. Researchers are turning to biological agents as an alternative. Among the biological agents which have effective insecticidal activity are narrow spectrum chemicals, pheromones and entomopathogens including viruses, bacteria and fungi. Biological agents having insecticidal activity are preferred because they tend to be targetable to one or a few species of pests with little or no toxicity to non-target plants and animals.

Several species of Bacillus are known to produce toxins which are lethal to insect larvae. D. P. Stahly, et al., "The Genus Bacillus—Insect Pathogens," Volume II, *The Prokaryotes (Second Edition), A Handbook of the Biology of Bacteria: Ecophysiology, Isolation, Identification and Applications*, pp. 1697–1745 (Springer-Verlag, New York, N.Y. 1991). *Bacillus sphaericus, B. thuringiensis*, spp., *B. popillae* and *B. lentimorbus* all have long been recognized to be etiological agents capable, upon being ingested, of killing the larvae of certain insects. Bacillus toxin polypeptides are known to exert their toxic effect in the gut of susceptible insect larvae.

Entomotoxic strains of *Bacillus sphaericus* are known which are lethal to insect larvae of Culex and Anopheles species. A. A. Yousten, J. Invertebr. Pathol. 43, 124–125 (1984); A. A. Yousten, Adv. Biothechnol. Processes 3, 315–343 (1984); E. W. Davidson, Mosquito News 44, 147–152 (1984); Mulla, et al., Mosquito News 44, 336–342 (1984). The toxic activity observed in *B. sphaericus* is associated with two polypeptides which respectively have a molecular weight of 41.9 kd (which toxin is also referred to herein as "BSP1") and 51.4 kd (which toxin is also referred to herein as "BSP2"). The toxin polypeptides are produced at the onset of sporulation and are expressed as parasporal crystals. Alone, each of the two polypeptides (i.e., BSP1 and BSP2) have no significant insecticidal activity, but in combination they constitute a potent larvacide. See, Baumann et al., J. Bacteriol. 170, 2045–2050 (1987).

Subspecies and strains of *Bacillus thuringiensis* also are known to produce insecticidal polypeptides, known as "delta endotoxins." *Bacillus thuringiensis* spp. *kurstaki* produces toxin which kills the larvae of several species of Lepidoptera, a major agricultural pest. *Bacillus thuringiensis* spp. *israelensis* produces toxin which is lethal to the larvae of mosquitoes and black flies, Dipteran species which are vectors for malaria and other human diseases. Thorne et al., J. Bacteriol. 166, 801–811 (1986) discusses structural similarities between the gene which encodes the toxin of *B. thuringiensis* spp. *israelensis* and the gene which encodes the toxin of *B. thuringiensis* spp. *kurstaki*. The delta endotoxins are expressed at the onset of sporulation in the form of parasporal crystalline inclusions.

It would be very desirable to produce large quantities of Bacillus insecticidal toxins in a form which, when released in insect infested areas, would facilitate ingestion of lethal amounts of the toxin by susceptible larvae. Growing large amount of Bacillus cells in culture for production of toxin is not commercially attractive. The production of toxin by Bacillus cell cultures is discontinuous, with toxin expression occurring only at the onset of sporulation. Moreover, Bacillus cells, being relatively fastidious, require complex culture media and stringent control of environmental factors to ensure healthy cultures. This makes producing larvicidal toxins commercially from cultures of Bacillus cells economically undesirable.

The relative inefficiency in producing Bacillus toxin by growing the natural host strain might be avoided by employing genetic engineering techniques to engineer a microorganisms to make one or more toxin polypeptides where the genetically engineered host cell is able to express large quantities of the toxins.

The expression of a heterologous protein has been described for many microorganisms. With respect to one type of Bacillus toxin, U.S. Pat. No. 4,918,006 describes expression of a 27 kd *B. thuringiensis* delta endotoxin in *E. coli*. There are several disadvantages to expressing Bacillus toxin in *E. coli*, however. First, *E. coli* are not as palatable to insect larvae as yeast. Yeast are feed attractants for insects. Second, since the bacterial cell wall is not as thick as the cell wall of yeast the expressed toxin may not be as stable in bacterial cells as in yeast cells. Third, because *E. coli* expression typically involves autonomous plasmids, the plasmids may undesirably be transferred to native bacterial strains. Fourth, transformed *E. coli* cells may express the toxin in an inactive and/or insoluble form, as heterologous proteins expressed in *E. coli* have to be reisolated and refolded so that the protein is present in its active conformation. Further, there are disadvantages to expression of insecticidal toxin in *S. cerevisiae* in that expression may be relatively low with integrative plasmids, and using $2\mu$ plasmid based autonomous plasmids undesirably may lead to transfer of plasmid to other cells, even though the transformed cells are first heat killed, since the plasmid DNA can survive heat treatment.

It would be very desirable to be able to produce large amounts of recombinant Bacillus entomotoxin peptides economically and continuously and in a form that is readily ingested by the targeted insect larvae and with substantially no risk of releasing the heterologous gene into the environment.

SUMMARY OF THE INVENTION

The present invention provides a novel and unexpectedly efficient method of producing large quantities of biologically active Bacillus entomotoxin compositions, by culturing cells of a species of methylotrophic yeast which harbor a heterologous gene for expressing a Bacillus entomotoxin polypeptide under conditions such that the heterologous gene is transcribed in the cells. The methylotrophic yeast cells are an attractive food and are readily ingested by susceptible insect larvae, such that the entomotoxin polypeptide may be efficiently delivered to the gut of the target insect where it takes effect.

In accordance with the present invention, high levels of Bacillus toxin are produced in cells of a methylotrophic yeast, preferably *P. pastoris* cells, as a protein which is primarily cell-associated and which is active in whole live, or killed, cells which may be ingested by the target insect larvae. Whole live or killed *P. pastoris* cells of the present invention are superior carriers of the entomotoxin in part because insect larvae readily feed on these yeast cells. Optionally, biologically active entomotoxic polypeptides may be purified from Bacillus-toxin-producing methylotrophic yeast cells by standard protein purification techniques and used in admixture with other ingredients to produce larvicidal compositions comprising Bacillus toxin.

Entomocidal Bacillus toxins are made by transformed *P. pastoris* having a single or multi-copy of a DNA (preferably integrated into the genome) encoding one or more Bacillus toxin polypeptides under the control of the promoter of the AOX1 gene of *P. pastoris* at levels of about 10% up to about 30% or more by weight of the total protein produced by such a *P. pastoris* cell culture. These levels of expression are greater than levels attainable using other cells such as *Escherichia coli* or *Saccharomyces cerevisiae* engineered to make a Bacillus toxin polypeptide.

The present invention also entails DNAs for transforming methylotrophic yeast cells, especially *P. pastoris* cells, to express at least one Bacillus entomotoxin, wherein the polypeptide coding region of such DNAs has a G+C content of between about 40% and about 55%, more preferably between about 45% and 50%. In particularly preferred embodiments of the DNAs of the invention, the polypeptide toxin coding region comprises at least about 80% methylotrophic yeast preferred codons, that is, codons which are most (or second-most) preferred by methylotrophic yeast cells, especially Pichia cells. The present invention also includes cultures of methylotrophic yeast cells which have been transformed with DNAs which encode an entomotoxin polypeptide and entomotoxin-expressing subcultures of such cultures, and the entomotoxin(s) produced by such cultures and subcultures.

The present invention, in preferred embodiments, entails a cellular combination comprising *P. pastoris* cells which express the 41.9 kd toxin and *P. pastoris* cells which express the 51.4 kd toxin polypeptide, in a ratio such that the combination of the *P. pastoris* cells contains approximately equimolar amounts of the respective toxin polypeptides. In other preferred embodiments, the invention entails a *P. pastoris* cell which can express the 41.9 kd and the 51.4 kd toxin polypeptides, most preferably in essentially equal molar amounts, as well as transforming DNAs which encode both polypeptide toxins for co-expression in a methylotrophic yeast cell.

BRIEF DESCRIPTION OF THE DRAWINGS

FIG. 1 shows a codon usage table which lists the individual codons and their relative preferences for encoding representative highly expressed genes of *Pichia pastoris*;

FIGS. 2A–2C show the amino acid sequence of the 41.9 kd entomotoxin polypeptide of *Bacillus sphaericus*, the nucleotide sequence of the native polypeptide coding region, and the nucleotide sequence of the synthetic polypeptide coding region encoded by *P. pastoris* preferred codons;

FIG. 2D shows the fourteen oligonucleotides constructed for the synthesis of the second of four fragments used in the construction of synthetic 41.9 kd toxin gene in Example I, Part B;

FIGS. 3A–3D show a nucleotide sequence comprising *P. pastoris* preferred codons which encodes the 51.4 kd entomotoxin polypeptide of *Bacillus sphaericus*;

FIGS. 4A and 4B show the nucleotide sequences of fragments A and B, respectively, which were ligated to form the DNA represented in FIG. 3, as well as oligonucleotides which comprise the respective fragments;

DETAILED DESCRIPTION OF THE INVENTION

Figure 5:
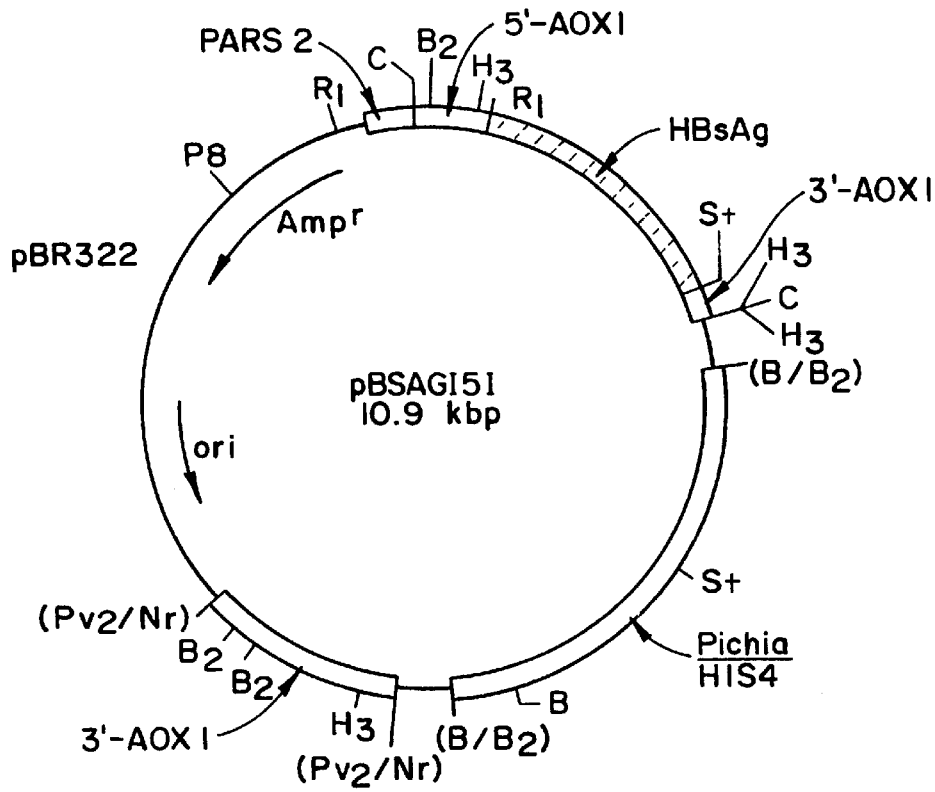
FIG. 5 is a restriction map of plasmid pBSAGI5I.

In one aspect, the present invention is a method of producing a Bacillus entomotoxin polypeptide comprising culturing cells of a species of methylotrophic yeast which have at least one gene which is capable of expressing a Bacillus entomotoxin polypeptide. Surprisingly, it has been found that an entomotoxin-encoding DNA segment which has a G+C content of between about 40% G+C and about 55% G+C, is capable of being expressed at high levels in methylotrophic yeast cells.

The invention further entails a DNA which comprises (1) a promoter segment of a first methylotrophic yeast gene, said segment comprising the promoter and transcription initiation site of said first gene, (2) a terminator segment of a second methylotrophic yeast gene, said terminator segment comprising the polyadenylation signal-encoding and polyadenylation site-encoding segments and the transcription termination signal of said second gene, said first and second methylotrophic yeast genes being from the same or different species and said first or second genes being the same or different and (3) a DNA segment encoding a Bacillus entomotoxin polypeptide and having between about 40% G+C content and about 55% G+C content and oriented and positioned operatively for transcription, between said promoter segment and said terminator segment. The terminator segment is oriented, with respect to direction of transcription from the promoter segment operatively for termination of transcription at said transcription terminator. In especially preferred embodiments, the DNA segment encoding the Bacillus toxin polypeptide comprises at least about 80% methylotrophic yeast preferred codons, i.e., codons which occur most frequently in endogenous genes of said yeast and has a G+C content of between about 45% and 50%. In a particularly preferred embodiment, the present invention involves a DNA of the present invention which is capable of expressing both the *B. sphaericus* 41.9 kd toxin and the *B. sphaericus* 51.4 kd toxin. *P. pastoris* cells of the invention transformed with said transforming DNAs of the invention are capable of co-expressing the 41.9 kd toxin and the 51.4 kd toxin in approximately equal molar amounts.

In yet another aspect, the invention entails a DNA which is capable of transforming cells of a species of methylotrophic yeast to express at least one Bacillus entomotoxin polypeptide, which DNA has the attributes of a DNA of the present invention described in the preceding paragraph and which also comprises a gene to provide a selectable marker to cells which harbor the DNA.

In still another aspect, the invention concerns a culture of methylotrophic yeast, transformed with at least one DNA according to the present invention, or a Bacillus toxin expressing subculture of said culture.

In a further aspect, the invention entails a DNA comprising a nucleic acid sequence which encodes a Bacillus toxin polypeptide, said toxin encoding sequence comprising at least about 80% methylotrophic yeast preferred codons and having a G+C content of between about 40% and 55%, more preferably between about 45% and 50%, and wherein said DNA is capable of being expressed in a methylotrophic yeast when oriented and positioned operatively for transcription between a transcription promoter segment and a transcription terminator segment function in said methylotrophic yeast.

The term "culture" means a propagation of cells in a medium supportive of their growth, and all subcultures thereof. A "subculture" as used herein means a culture of the cells grown from cells of a source culture or any subculture of the source culture.

The term "Bacillus entomotoxin polypeptide" or "Bacillus entomotoxin" or "Bacillus larvicidal toxin" or simply "Bacillus toxin" means a polypeptide, whether produced from a native or synthetic gene, having an amino acid sequence which is the same as or equivalent to a Bacillus-produced protein, or biologically active segment thereof, which is toxic to insect larvae of a species susceptible to the toxin.

A "methylotrophic yeast" as used herein means a species of yeast which is capable of using methanol as a carbon source for growth. Preferred among such species are *P. pastoris* and *Hansenula polymorpha*. Most preferred is *P. pastoris*. While the detailed description herein is largely limited to *P. pastoris*, it will be readily apparent to the skilled how another species of methylotrophic yeast such as *Hansenula polymorpha* can be employed in place of *P. pastoris* in carrying out the invention.

By the phrase "substantially comprising *P. pastoris* preferred codons" is meant that at least about 80%, preferably at least about 90%, more preferably about 95% or more of the codons encoding the Bacillus entomotoxin polypeptide are codons which are most preferred or second-most preferred (i.e., as determined by the frequency of occurrence in one or more native *P. pastoris* genes) by *P. pastoris*.

As used herein, the "G+C content" of a DNA segment encoding a toxin refers to the percentage of guanine and cytosine residues in the segment of the toxin polypeptide encoding segment.

Methods for transforming a methylotrophic yeast such as *P. pastoris* with DNAs comprising genes for expression of heterologous proteins are known in the art. It is known to culture such yeast cells which have a gene encoding a heterologous protein so as to express the heterologous protein from such a gene. These methods can be used to make cultures of said methylotrophic yeast cells according to the invention capable of expressing a Bacillus toxin containing composition which is lethal to susceptible insect larvae. Various methods employing the *P. pastoris* cell cultures are described in the Examples which follow.

With respect to *P. pastoris*, a DNA according to the invention may advantageously comprise a selectable marker gene. A selectable marker gene may be employed which is functional in *P. pastoris* cells to allow cells transformed with the DNA of the invention to be distinguished from untransformed cells. Preferably a dominant selectable marker or a marker which complements an auxotrophic mutation in the cells to be transformed may be used. The well known neomycin resistance gene from bacterial transposon Tn5 which provides resistance to the antibiotic G418 is one example of a gene that can provide a dominant selectable marker in *P. pastoris* cells. Another example is the kanamycin resistance gene from transposon Tn 903 which confers kanamycin, neomycin and G-148 resistance in *P. pastoris* cells. Yet another example is the invertase gene SUC2 which can function as a dominant marker. Use of the invertase gene as a transformation marker is described in U.S. Pat. No. 4,857,467. Among the genes providing complementation for auxotrophic mutations are the *P. pastoris* HIS4 gene (for transformation of HIS4 strains of *P. pastoris*), the *S. cerevisiae* HIS4 gene (for transformation HIS4 strains of *P. pastoris*), the *P. pastoris* ARG4 (arginosuccinatelyase) gene (for transformation ARG4 strains of *P. pastoris*), and the *S. cerevisiae* ARG4 gene (for transformation of ARG4 strains of *P. pastoris*).

With further reference to *P. pastoris*, in the promoter segment of a DNA of the invention for transforming *P. pastoris* to express one or more Bacillus entomotoxin polypeptides, the promoter of any *P. pastoris* gene can be employed for transcription of the Bacillus toxin encoding DNA segment of the DNA of the invention. Preferably, the promoter will be the promoter of a *P. pastoris* gene, the transcription of which is highly regulated by compositions easily manipulated in *P. pastoris* cultures, for example, the carbon source for culture growth. A preferred *P. pastoris* gene is the major alcohol oxidase gene (AOX1 gene), the promoter of which is normally substantially inactive in the absence of methanol in the culture medium (unless the cells experience carbon starvation), but which is highly active in the presence of methanol. In the promoter segment of the DNA of the invention, the transcription initiation signal and the segment between the promoter and the transcription initiation signal will preferably be from the same *P. pastoris* gene as the promoter.

The "terminator segment" of a DNA of the invention has a subsegment which encodes a polyadenylation signal and polyadenylation site in the transcript and a subsegment which provides a transcription termination signal for the transcription from said promoter. With reference to *P. pastoris*, the entire terminator segment of a transforming DNA of the invention will preferably be taken from one *P. pastoris* protein-encoding gene, which may be the same as or different from the *P. pastoris* gene from which the promoter of the DNA of the invention is taken. It is preferred that both the terminator segment and the promoter segment controlling transcription of the Bacillus toxin encoding segment be from the *P. pastoris* AOX1 gene.

In a DNA according to the invention, the DNA segment encoding a Bacillus entomotoxin can be any open reading frame that includes a translation-start triplet and a translation-stop triplet and that includes, starting with the translation-start triplet and ending with the triplet adjacent to the translation-stop triplet, a complete Bacillus toxin encoding segment having between about 40% G+C content and 55% G+C content, more preferably between about 45% and 50%, and being capable of expression in a methylotrophic yeast cell. Preferably, the polypeptide encoding segment comprises at least about 80% *P. pastoris* preferred codons. Examples of such DNA segments are the *P. pastoris* vectors, pBSP1, pBSP2 and pBSP1+2, and transformation of *P. pastoris* cells with such plasmids for the expression of *Bacillus sphaericus* toxin polypeptides are described in the Examples below.

Engineering *P. pastoris* cells by inserting a native Bacillus entomotoxin-encoding gene (~35% G+C content) has been found by the inventors to produce very small amounts, if any, (0 to <0.01% of total protein) of recombinant entomotoxin polypeptide. Surprisingly, the inventors have found that synthetic Bacillus entomotoxin encoding segments comprising *P. pastoris* preferred codons and having a G+C content of from about 40% G+C to about 55% G+C, more preferably from about 45% to 50% G+C, are expressed at extremely high levels (10%–30% of total protein) in methylotrophic yeasts. The levels of expression attained with transformed *P. pastoris* yeast cells of the invention are several hundred to several thousand times higher than levels which are attainable by expression of the native bacterial gene in *P. pastoris* and comparable to, or higher than, levels of expression of the toxin in the native Bacillus species.

A DNA of the invention which comprises a segment encoding a Bacillus toxin may be any DNA which has a Bacillus toxin-encoding segment of the above-defined G+C content and which is capable upon transfection into a methylotrophic yeast of being expressed to make the insecticidal toxin. In a DNA according to the invention which has a promoter segment and a terminator segment bracketing a Bacillus toxin-encoding segment, the Bacillus toxin-encoding segment is positioned and oriented with respect to the promoter and the terminator segments operatively for transcription of the Bacillus toxin-encoding segment under control of the promoter in the promoter segment so as to produce a transcript which is capable of providing expression of the Bacillus toxin protein. It is well within the skill of the art to position and orient such a DNA segment which is transcribed under the control of said promoter segment, operatively for transcription in a methylotrophic yeast such as *P. pastoris*. A toxin encoding DNA segment bracketed by a promoter segment and a terminator segment, operatively for transcription of said toxin encoding segment is sometimes referred to herein as an expression cassette. With respect to an expression cassette, as understood in the art, the Bacillus toxin-encoding segment including the translation-start and translation-stop triplets must be downstream from the transcription initiation site and upstream from the polyadenylation signal- and polyadenylation site-encoding segment of the terminator segment which in turn must be upstream from the transcription termination site of the terminator segment. The segment encoding the Bacillus toxin protein must be oriented with the translation-start triplet upstream from the translation-stop triplet. Preferably, in a DNA according to the invention, for each expression cassette, there will be only a single, long open reading frame which has the sequence encoding a Bacillus toxin polypeptide between the promoter which drives transcription of the Bacillus toxin encoding segment and the transcription terminator segment, and preferably the transcription terminator segment will have a single polyadenylation signal and site. By the terms "downstream" and "upstream" in a DNA of the invention is meant downstream and upstream respectively with respect to the direction of transcription from the promoter driving transcription of the Bacillus toxin-encoding segment.

A transforming DNA according to the invention preferably includes elements necessary for its selection and replication in bacteria, especially *E. coli*. This facilitates production of large quantities of the DNA by replication in bacteria. In this regard, a preferred DNA of the invention is a plasmid which includes a segment comprising the origin of replication and ampicillin-resistance or tetracycline-resistance gene of the plasmid pBR322.

A DNA of the invention which includes an origin of replication or autonomous replication sequence (ARS) which is functional in *P. pastoris* can be maintained as an episomal DNA (e.g., closed circular plasmid) after transformation into *P. pastoris*. A number of DNA segments comprising origins of replication and autonomous replication sequences functional in *P. pastoris* are known in the art.

Integration of a DNA of the invention may occur via homologous recombination into the *P. pastoris* genome in a certain proportion of the cells. Integration can be either additive or by gene disruption, as described below. Additive integration can be accomplished by transformation of *P. pastoris* cells with linear DNA fragments, including linearized plasmids, or circularized plasmids, which fragments or plasmids comprise one or more DNA segments, at least about 200 bp in length, which are homologous in sequence to segments which occur in the *P. pastoris* genome. Integration by gene disruption can be accomplished by transformation of *P. pastoris* cells with linear fragments which have "targeting segments" at their ends. A "targeting segment" is at least about 200 bp in length and has a sequence homologous to that of a part of the gene to be disrupted by the integration. The targeting segment at one end of the linear fragment to be integrated differs from that at the other end, but the two segments are oriented with respect to each other in the fragment to be integrated in the same way that the corresponding segments of homologous sequence are oriented in the gene to be disrupted such that the DNA of the invention will be incorporated into the cellular genome.

Methods for causing integration of heterologous DNA into yeast genomes, including those of *P. pastoris*, and other methylotrophic yeasts, are well known in the art and may be applied with the DNAs of the present invention. See, e.g., European Patent Application Publication No. 0 226 752. Targeting the sites of disruptive integration to preferred sites in the *P. pastoris* genome is accomplished by incorporating in the transforming DNA "targeting segments" which are segments at the two ends of a linearized DNA according to the invention which segments have sequences homologous to the desired sites of integration into the genome. If the transforming DNA is a plasmid, it can be linearized conveniently by cutting with one or more restriction enzymes that cut at suitable site or sites to yield a linear transforming DNA of the invention with targeting segments at its ends. Suitable targeting segments will be at least about 200 bp in length. Examples of treating transforming plasmid DNAs of the invention in this way are provided in the Examples (e.g., BglII-digesting a pAO804-derivative having a synthetic Bacillus toxin-encoding segment that remains uncut in the BglII digestion).

Particularly in the case of methylotrophic yeasts such as *P. pastoris*, which have a "major" alcohol oxidase gene which has properties similar to that of the AOXI gene of *P. pastoris* and a "minor" alcohol oxidase gene which has properties similar to that of the AOXII gene of *P. pastoris*, it is advantageous to employ, as targeting segments at the termini of the linear DNA according to the invention, segments from the 5'-end and the 3'-end of the "major" alcohol oxidase gene locus and to employ, as the promoter segment of the expression cassette of such a linear DNA of the invention, a segment comprising the promoter of the "major" alcohol oxidase gene, whereby said promoter will drive transcription. Then the DNA according to the invention will be targeted to insert itself at the "major" alcohol oxidase gene locus of a transformed cell, disrupting the "major" alcohol oxidase gene whereby the cell will exhibit slower growth on methanol than cells in which such insertion, and disruption of the "major" alcohol oxidase gene, did not occur. Such cells are referred to herein as Mut$^{+/-}$ cells. Further, the properties of the "major" alcohol oxidase gene promoter (i.e. high transcriptional activity with methanol as carbon source or under carbon starvation) can be utilized to advantageously control transcription of a Bacillus toxin-encoding segment and thus expression of the corresponding Bacillus toxin polypeptide. In a culture grown from a cell transformed to have such a DNA of the invention integrated at the "major" alcohol oxidase gene locus, culture medium containing glycerol as carbon source may be used to increase the cell population to a desirably high level and then the carbon source can be shifted to methanol to induce transcription of the Bacillus toxin-encoding DNA, and expression and production of Bacillus toxin protein at a high rate. Alternatively, the cells can be grown on methanol plus sorbitol, or methanol plus alanine so as to obtain simultaneous growth and induction of the toxin-encoding DNA, since sorbitol and alanine are utilizable carbon sources which do not repress induction by methanol.

*P. pastoris* cells also may be transformed by addition-type integration of a transforming DNA at a site in the host's genome. Addition-type integration does not disrupt the expression of the "major" alcohol oxidase gene. Such transformants result in a Mut$^+$ phenotype. With respect to Mut$^+$ cells transformed with a DNA according to the invention, the transforming DNA of the invention preferably will be incorporated in the host's AOX1 gene locus at a point upstream from the host's "major" alcohol oxidase promoter (e.g., by SacI-digestion of a pAO804-derivative having a Bacillus toxin encoding segment that remains uncut in the SacI digestion). It is also possible to cause said transforming DNA to be incorporated in a portion of transformed cells at the HIS4 gene locus by using a SalI-digestion of said pAO804-derivative which cuts said derivative at the HIS4 locus or by transforming with an intact, circular pAO804-derivative. Furthermore, transformation with an intact pAO804 derivative may result in integration of the vector in a portion of the cells at a site in the AOX1 or HIS4 locus.

Moreover, it is very beneficial to employ a culture of *P. pastoris* cells which harbor multiple copies of a transforming DNA of the invention, each of which DNAs contain one or more expression cassettes. By "multiple copies" or "multi-copy", it is meant that at least 2 up to about 20 or more copies of the expression cassette are present in a transformed cell of the present invention. Where said transforming DNAs are incorporated by addition-type integration to yield Mut$^+$ transformant cells, a proportion of the transformants will be multi-copy integrants.

In a DNA of the present invention, the nucleotide sequence of a synthetic Bacillus toxin encoding region may be derived from the nucleotide sequence or amino acid sequence corresponding to the native Bacillus toxin gene or polypeptide using backtranslation or otherwise selecting codons which will provide an open reading frame encoding a Bacillus toxin and having a G+C content of about 40%–55%.

Native toxin encoding genes from Bacillus species and strains which produce entomotoxin polypeptides may be cloned and their genes sequenced using standard methods. Many entomotoxic strains of Bacillus are well known and publicly available, such as *Bacillus sphaericus, Bacillus thuringiensis, Bacillus popillia* and *Bacillus lentimorbus* strains which can be obtained from the American Type Culture Collection, Rockville, Md. or from the National Regional Research Laboratory in Peoria, Ill. The present invention is exemplified with *Bacillus sphaericus* strain 1593 (ATCC deposit number 33203). Entomotoxic Bacillus species and strains may also be obtained from their natural habitat, as by isolation from dead insect larvae or the surrounding soil.

Entomotoxin genes are generally contained on one or more plasmids in Bacillus cells. This may be readily ascertained, for example, by curing entomotoxic cells of their plasmids by acridine orange treatment and assaying to confirm loss of toxicity. Plasmid DNA isolated from a culture of Bacillus cells (e.g., by CsCl density gradient centrifugation) may be cleaved into suitably sized fragments by partial digestion with a suitable restriction endonuclease (e.g., Sau 3A, etc.) as known in the art. Restricted DNA fragments of appropriate size so as to include an intact entomotoxin gene (e.g., 1–5 Kb) for a polypeptide having a molecular weight of about 150 kd or less) may be cloned into an expression vector, used to transform a suitable bacterial host and screened in a biological assay for expression of active entomotoxin (Example VIII describes such a bioassay for toxin activity). The cloned Bacillus entomotoxin gene may then be sequenced by standard techniques and the open reading frame located.

Entomotoxin polypeptides which may be expressed in accordance with the present invention include, but are not limited to, the 41.9 kd toxin of *B. sphaericus* and the 51.4 kd toxin of *B. sphaericus* (Arapinis et al., Nucl. Acids Res. 16, 7731 (1988), the 27 kd insecticidal toxin of *B. thuringiensis israelensis* (e.g., U.S. Pat. No. 4,918,006), the 130 kd insecticidal toxin of *B. thuringiensis kurstaki* (Widner et al., J. Bacteriol. 171, 965–974 (1989)), the 66 kd insecticidal toxin of *B. thuringiensis kurstaki* HD263 (Donovan et al., Mol. Gen. Genet. 214, 365–372 (1988)) and the like.

The nucleic acid and amino acid sequences of many Bacillus entomotoxins and cloning strategies employed have been published: Sen et al., Agric. Biol. Chem. 52, 873–878 (1988); McPherson et al., Biotechnol. 6, 61–66 (1988); Donovan et al., J. Bacteriol. 170, 4732–4738 (1988); Chungjatupornchai et al., Eur. J. Biochem. 173, 9–16 (1988); Brizzard and Whiteley, Nucl. Acids Res. 16, pp. 2723–2724 (1988); Ward and Ellar, Nucl. Acids Res. 15, pp. 7195 (1987); Sekar, et al., P.N.A.S. (USA) 84, pp. 7036–7040 (1987); Oeda, et al., Gene 53, pp. 113–119 (1987); Hofte, et al., Nucl. Acids Res. 15, 7183 (1987); Galjart, et al., Curr. Microbiol. 16, pp. 171–177 (1987); Thorne, et al., J. Bacteriol. 166, pp. 801–811 (1986); Hofte, et al., Eur. J. Biochem. 161, pp. 273–280 (1986); Geiser, et al., Gene 48, pp. 109–118 (1986); Waalwijk, et al., Nucl. Acids Res. 13, pp. 8207–8217 (1985); Shibano, et al., Gene 34, pp. 243–251 (1985); and Adang, et al., Gene 36, pp. 289–300 (1985).

From the primary amino acid sequence or the native nucleotide sequence of the selected toxin, a sequence for a toxin-encoding DNA of the invention may be readily generated, either by back-translation from the amino acid sequence or by codon substitution in the open reading frame so as to provide a DNA segment having an G+C content in the range of 40% to 55%, more preferably 45% to 50% G+C. Computer programs are commercially available which, in accordance with predetermined parameters (e.g., codon selection preferences, restriction site analysis, etc.), can back-translate a desired nucleotide sequence from a predetermined amino acid sequence (e.g., PC Gene, Inteligenetics Co., Mountain View, Calif. 94040; The University of Wisconsin Genetics Computer Group Programs (UWGCG) Madison, Wis.).

With respect to codon selection, a wide variety of codons, including those employed by various eukaryatic organisms including mammals, may be used in designing a Bacillus toxin encoding segment of a DNA of the invention having a coding segment with a G+C content of about 40%–55%. Preferably, a Bacillus toxin encoding segment of a DNA of the present invention will comprise methylotrophic yeast preferred codons, especially *P. pastoris* preferred codons. The most preferred codons are those which are frequently found in highly expressed *P. pastoris* genes, including the major alcohol oxidase gene (AOX1), the minor alcohol oxidase gene (AOX2), and the major dihydroxyacetone synthase gene (DAS1), the secondary dihydroxyacetone gene (DAS2), the GAP gene and the like. A codon usage table, constructed by analyzing the codons used to encode the AOXI, AOX2, DAS1, DAS2 and GAP genes of *P. pastoris* showing the *P. pastoris* codon preferences and the average percentage of times that each codon appears in the coding sequence for the five gene products of above-mentioned highly expressed genes is set forth in FIG. 1.

With respect to Pichia preferred codon selection, a single amino acid is encoded frequently by two or more codons which differ the base at the third position. Due to the relatively low G+C content in *Bacillus entomotoxin* native genes (~35 G+C content), it may be desirable, in instances where the second-most preferred has a G or C at the third position, while the most preferred codon has an A or T at the third position (see FIG. 1), to select the second-most preferred codon so as to increase the G+C content of the toxin encoding segment, if necessary.

Figure 15:
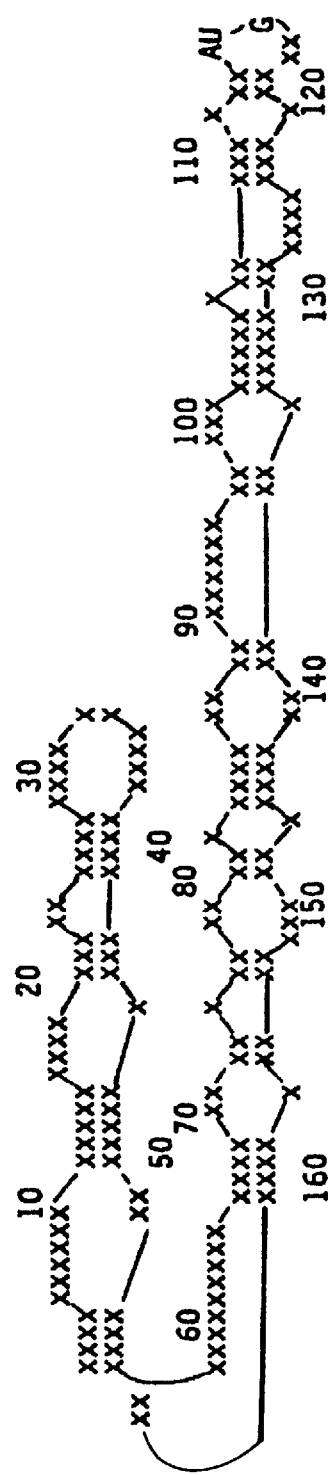
FIG. 15 represents the predicted secondary structure of the mRNA corresponding to the synthetic 51.4 Kd toxin gene, wherein a total of 164 nucleotides comprising the mRNA leader (114 nucleotides) and the initial 50 nucleotides (including AUG, shown to be free of secondary structure) of the translated region are used for analysis.

It may also be desirable with respect to selection of the nucleic sequence of the synthetic gene to design the initial 50 to 75 nucleotides, including the translation initiation codon (AUG) such that the predicted mRNA secondary structure (e.g., using the method of Zuker and Steigler, Nucleic Acid, Res. 9, 133–148 (1981)) at the initiation codon AUG is free of secondary structure. See FIG. 15.

Another important factor in codon selection is providing a DNA segment which is devoid of restriction endonuclease sites identical to those used for linearizing a transforming DNA of the present invention. With respect to the *P. pastoris* vectors exemplified herein, transformation may preferably be carried out by linearizing the transforming DNA at BglII, SacI, NotI, StuI or SalI sites. Therefore, a DNA according to the invention should comprise a Bacillus toxin encoding segment which is devoid of such restriction sites. One or more second-most preferred codons may be used to satisfy this criterion.

Further with respect to codon selection, it will often be desirable to synthesize a toxin encoding DNA of the invention in fragments which are subsequently ligated to complete the entire coding segment. In this instance, a nucleotide sequence comprising, for example, Pichia preferred codons may be analyzed to locate unique restriction sites separated by about 200 to 1000 bases. These unique restriction sites may be used to define the ends of discrete DNA fragments which may be individually synthesized and ligated to each other in a predetermined orientation to yield an entire toxin encoding DNA segment of the invention (See Example I). It may be desirable to use one or more second-most preferred codons if this permits introduction of a strategically located restriction site. Computer programs for searching and identifying restriction sites contained within a nucleotide sequence are well known in the art, such as PC Gene, by Inteligenetics Co., Mountain View, Calif. 94040 or The University of Wisconsin Genetics Computer Group Progrsm (UWGCG) Madison, Wis.

Each of the DNA fragments comprising a toxin coding segment of the invention may be assembled from oligonucleotides of suitable length. Standard methods for oligonucleotide synthesis, such as automated synthesis on an Applied Biosystems 380B DNA synthesizer or the like may be employed to synthesize a series of oligonucleotides which may be hybridized and ligated to produce the respective DNA fragments which may be assembled (i.e., ligated) into a toxin encoding DNA segment of the invention. For example, the oligonucleotides used to synthesize the coding sequence for the synthetic BSP2 gene are identified in the FIGS. 4A and 4B.

The synthesis of synthetic *Bacillus sphaericus* toxin encoding DNAs comprising Pichia preferred codons is described in detail in the Examples which follow. Also described in the Examples is the construction of a transforming DNA according to the invention having one or more expression cassette(s) inserted in a derivative vector of the *P. pastoris* expression vector pAO804, wherein the transforming DNA comprises a segment which encodes (1) the 41.9 kd toxin of *Bacillus sphaericus* (BSP1), (2) the 51.4 kd toxin of *Bacillus sphaericus* or (3) both the 41.9 kd and the 51.4 kd toxins (BSP1+2). For each of these constructs, the DNA segment encoding the BSP1 toxin (i.e., the 41.9 kd polypeptide) or BSP2 toxin (i.e., the 51.4 kd polypeptide) were individually ligated into a unique site in pHIL-D5, a derivative of pAO804, and the respective resulting plasmids with the BSP1 fragment or BSP2 fragment (or both) inserted in the correct orientation in respective insertion site(s) (i.e., operative for expression of BSP1 and/or BSP2) were selected. Such a resulting plasmid or fragment thereof which is capable of transforming *P. pastoris* to express, respectively, the BSP1 toxin or BSP2 toxin or both the BSP1 toxin and the BSP2 toxin are transforming DNAs according to the invention.

Unexpectedly, Bacillus toxin polypeptides encoded by Pichia preferred codons are expressed in transformed *P. pastoris* cells at high levels in biologically active form. The surprising and advantageous result that Bacillus toxin protein is not cleaved by the host cell into inactive fragments is established by electrophoretic analysis which indicates the absence of such degradation products.

A further surprising result is that the 41.9 kd and the 51.4 kd toxin polypeptides are co-expressible in Pichia and assembled into the active toxin complex. This is believed to be the first time that two heterologous interacting proteins have been co-expressed in methylotrophic yeast to yield a biologically active complex. Moreover, where the 41.9 kd and the 51.4 kd polypeptides are co-expressed they are expressed in nearly equimolar amounts, whereas when they are expressed individually the 51.4 kd polypeptide was shown to be expressed at higher levels. Co-expression at near equimolar amounts results in optimal biological activity. An excess concentration of the 51.4 kd polypeptide (4× or more) relative to the 41.9 kd polypeptide would result in relatively reduced or no toxin activity. Thus, *P. pastoris* cells which are transformed with a DNA of the invention such that high level of the 41.9 kd and the 51.4 kd toxin polypeptides are produced in approximately the same molar concentration are especially preferred. The highest levels of co-expression have been obtained with multi-copy integrants. The presence of multiple copies of expression cassette encoding the 51.4 kd polypeptide also gives higher levels of expression than single copy transformants. Interestingly, this multi-copy effect is not observed in cells transformed with DNAs having only expression cassettes encoding the 41.9 kd toxin. Single copy and multi-copy integrants encoding only the 41.9 kd polypeptide exhibit similar levels of expression. The simultaneous expression of the 51.4 kd and 41.9 kd polypeptides, however, synergistically allows the 41.9 kd polypeptide to be expressed at higher levels.

The Bacillus toxin made according to the method of the invention by *P. pastoris* cultures and subcultures of the invention can be purified if desired from the cells by techniques well known in the protein purification art. It is however preferred that intact, whole toxin containing yeast cells be used to provide an insecticidal composition. More preferably, killed recombinant yeast cells are employed. Killing such Bacillus toxin expressing yeast cells may conveniently be accomplished by maintaining them at a temperature of about 55° C. to about 75° C., preferably about 65° C. for between about 10 and about 60 minutes. This effectively kills about 99.9% of the cells without significantly reducing activity of the expressed toxin polypeptide.

Bacillus toxins provided by the present invention, whether isolated or as part of inactivated whole cells or a membrane fraction thereof can be used as narrow spectrum insecticides. Such insecticides are administered using methods which are well known in the art, such as by spraying it in a powder form or in an aqueous suspension. It is well within the skill of the art to determine application rates based on potency of the killed whole cells in vitro insecticidal assays. (M. S. Mulla, et al, J. American Mosquito Control Association, 1 (3) 310–315 (1985), C. A. Sandoski, et al., J. American Mosquito Control Association, 2 (4) 461–468 (1986)

The invention provides very concentrated insecticide compositions because of the ability of methylotrophic yeast including *P. pastoris* to express Bacillus toxin to levels which are significantly higher than those levels attainable using other host cells and which are equal to or higher than levels produced by native entomotoxic Bacillus cells.

All of the patents and publications referred to in this application are hereby expressly incorporated by reference into this application.

The following non-limiting Examples describe and illustrate the present invention in greater detail.

EXAMPLE I

Bacillus Sphaericus 41.9 kd Toxin Gene Isolation/Synthesis

A. Isolation of Native Bst Gene

*B. sphaericus* strain 1593, obtained from the American Type Culture Collection (accession no. 33203), was used for isolation of the gene encoding the 41.9 kd larvicidal toxin. *B. sphaericus* strain 1593 was grown at 30° C. in Luria-Bertani medium supplemented with 10 mM $MgCl_2$ and 1 mM NaCl [Hindley, J. and Berry, C. (1987). Molecular Microbiology, 1:187]. Genomic DNA was isolated as described [Souza, A., Rajan, V., Jayaraman, K. (1988). Biotechnology, 7:81], and digested with EcoRI and HindIII to liberate a fragment of approximately 1.9 Kb. The complete toxin gene should be contained on this fragment. An aliquot of the digest was separated on an agarose gel, transferred to nitrocellulose, and probed with an oligonucleotide homologous to the *B. sphaericus* toxin gene: 5' GAT AAG AGT ACT TCC TAT TAT TGA TTT CAC 3' (SEQ. ID NO: 1). The Southern blot indicated that a fragment of the expected size hybridized to the oligonucleotide.

The area of the gel containing DNA fragments of approximately 1900 bp was excised and the isolated DNA sequences were inserted into pBR322 which has been previously digested with EcoRI and HindIII and capped. The resulting plasmids were used to transform *E. coli* strain HB101.

The $Amp^R$ *E. coli* transformants were screened with the same oligonucleotide homologous to the *B. sphaericus* toxin gene as used before. Several positive colonies were rescreened and one was found by DNA sequencing to contain an insert encoding the toxin gene. This clone was named pBR322-BSP1.

B. Construction of Synthetic 41.9 kd toxin Gene

1. Generation of the synthetic gene sequence

In order to formulate a Pichia-optimized nucleotide sequence for a synthetic *B. sphaericus* toxin gene, the codon usage and G+C content of several highly expressed *P. pastoris* genes (AOX1, AOX2, DAS1, DAS2 and GAP) were examined, and a Pichia codon usage table (FIG. 1) was prepared from the sequences of the five Pichia genes. It was discovered that the average G+C content of the analyzed Pichia genes is approximately 47%, whereas the G+C content of the *B. sphaericus* toxin gene is approximately 35%.

With the aid of a computer program, the codon usage table was used to generate the composition of the synthetic *B. sphaericus* toxin gene by back-translating of the toxin amino acid sequence. In general, the most frequently used Pichia codon was chosen for each amino acid. However, in cases in which the most used codon contained an A or T in the third, or wobble, position and the second most frequently used codon contained a G or C in this position, the second codon was chosen. The use of Pichia-preferred codons resulted in a creation of a synthetic toxin gene sequence with a G+C content of approximately 49%.

Analysis of the new sequence for restriction sites revealed that it contained three BglII sites, which were eliminated by changing an appropriate base at each of these sites in the gene sequence while preserving the amino acid sequence. Elimination of these sites facilitated subsequent cloning steps.

To facilitate synthesis of the complete new *B. sphaericus* toxin gene from ligation of smaller fragments of the gene, a computer program was used to locate sequences of the gene at which a single base change would result in the creation of a restriction site while conserving the amino acid sequence. Restriction sites separated by approximately 300 bp were created in this manner so that the gene could be divided into four fragments of approximately 200–300 bp. The native sequence and the computer-generated sequence with the restriction site modifications are shown in FIG. 2.

2. Synthesis of the new *B. sphaericus* gene (BSP1)

The complete optimized *B. sphaericus* toxin gene was constructed by ligation of four smaller fragments. Each fragment was synthesized from a series of 8–14 overlapping oligonucleotides. The four fragments, when combined, comprised the complete optimized toxin gene and were assembled by ligation of conveniently placed restricted sites located at the ends of each fragment.

| Fragment 1 | HindIII(EcoRI)-PstI | ~300 bp |
| Fragment 2 | PstI-BamHI | ~290 bp |
| Fragment 3 | BamHI-SmaI | ~330 bp |
| Fragment 4 | SamI-EcoRI | ~220 bp | a. Fragment 2

FIG. 2A outlines the series of 14 oligonucleotides constructed for the synthesis of the second of the four fragments. To initiate the synthesis of fragment #2, 12 of the 14 constituent oligonucleotides (100 pmoles of each) were kinased in a pool with unlabeled ATP. Only the two oligonucleotides with free 5' ends were left unkinased. Following the kinase reaction, the remaining two oligonucleotides (100 pmoles of each) were added to the pool, which was extracted with phenol and precipitated with ethanol. The pelleted oligonucleotides were dissolved in 1× HindIII buffer (made following manufacturer's instructions), heated in a boiling-water bath for five minutes, and allowed to slow cool and anneal overnight at 15° C. The following morning, ligase buffer (60 mM Tris.HCl; pH 7.6, 5 mM MgCl$_2$, 5 mM DTT, 1 mM ATP) and T4 DNA ligase were added to the annealed oligonucleotides, and the mixture was left at 15° C. for approximately 24 hours. The ligation mix was separated on a 2% agarose gel and the area of the gel containing the desired-full length fragments (~300 bp) was excised and the DNA was isolated.

The isolated fragments were inserted into M13mp8 which had been digested with BamHI and PstI and left uncapped, and the resulting vectors were introduced into *E. coli*. Single-stranded DNA obtained from ten white plaques was screened by solution hybridization with one of the oligonucleotides used for construction of the fragment, followed by agarose gel electrophoresis. Five of the ten white plaques hybridized to the screening oligonucleotide and were sequenced. One of the five clones, called pBS-2, contained the correct, full-length fragment 2 sequence on a PstI-BamHI fragment, whereas the other four contained either shorter fragments or full-length fragments with two or three errors.

b. Construction of fragments 1 and 3

Fragments 1 (HindIII-PstI) and 3 (BamHI-SmaI) were synthesized using appropriate sized oligos, cloned, and sequenced essentially as described for fragment 2, above.

With respect to fragment 1, solution hybridizations of the 29 white plaques which resulted from cloning the fragment into M13 identified 15 plaques containing DNA sequences corresponding to the screening oligonucleotide. Sequencing of inserts contained in 12 of these plaques revealed that three plaques harbored the correct, full-length fragment 1 DNA sequence. Double-stranded plasmid DNA was prepared from one of the correct clones (pBS-1). Digestion of this DNA with HindIII and PstI released a fragment of the correct size (300 bp).

With respect to fragment 3, essentially the same procedure was followed. Double-stranded plasmid DNA was prepared from one clone (pBS-3) and the 330 bp BamHI-SmaI fragment was isolated. The 300 bp fragment and the 330 bp fragment were isolated and assembled in M13 with the other two synthesized fragments (see Section B.3 of this Example).

c. Ligation of fragment 2 to fragment 3

The BamHI-SmaI fragment (pBS-3) was then cloned into pBS-2, which had been digested with BamHI and SmaI. Mini-prep plasmid DNA from 18 resulting clones was digested with EcoRI and HindIII (to cleave corresponding restriction sites in the polylinker of M13mp8). One clone, pBS-23, contained a fragment of the correct size (~620 bp) while the others had only a 330 bp fragment. The insert of pBS-23, consisting of fragment 2 fused to fragment 3, was confirmed as correct by sequence analysis.

d. Construction of fragment 4 and ligation to fragments 2 and 3

Fragment 4 (identified in FIG. 2) was also synthesized using appropriate oligonucleotides, cloned and sequenced as described for fragment 2, above. A fragment of the expected size (220 bp) for fragment 4 was isolated, ligated in to M13, and the ligation mixture was used to transform JM103. Single-stranded DNA from eighteen white plaques was used in two separate solution hybridization analyses. Two different oligonucleotides were used as probes in the two solution hybridizations, one from each end of the fragment 4. Six of the 18 clones hybridized to only one oligonucleotide indicating incomplete fragment assembly. Large template preps were grown of the remaining clones, which were then sequenced. One of the 12 clones (clone #2) had three errors located within an eight base region that could readily be mutagenized to the correct sequence with a single mutagenesis oligonucleotide. The incorrect sequence, and the oligos used to correct the errors by mutagenesis were as follows:

incorrect sequence:
5'-GGATCtATACCCGGGAGTACACTAACACTGA-GAAtTTttCAGTCAGATACACTGGTTACGTCTT-GGC-3' (SEQ. ID NO: 2)

Mutagenesis oligo
5'-CACTAACACTGAGAACTTCCCAGTCAGATAC-ACTG-3' (SEQ. ID NO: 3)

Screening oligo
5'-TGAGAACTTCCCAGTCAG-3' (SEQ. ID NO: 4)

The in in vitro mutagenesis was performed and two isolates were sequenced; both contained the correct sequence. One of these (pBS4) was grown as a large-scale plasmid prep, then digested with HindIII and SmaI in preparation for the cloning of the other two fragments (#1 and #2+3).

3. Fragment ligation

A large plasmid prep of fragment 1 (pBS1) was digested with HindIII and PstI and the 300 bp fragment was isolated. A large-scale plasmid prep of pBS23 was digested with PstI and SmaI and the 620 bp fragment was isolated. The HindIII/PstI fragment of pBS1 and the PstI/SmaI fragment from pBS23 were ligated in a three-way ligation to the pBS4 vector which had been cut with HindIII and SmaI. The ligation was transformed into JM103 and mini-RF preps were grown from 24 transformants analyzed (pSBS100#4 and #17) had an insert of the correct size (1140 bp). Large-scale template and plasmid preps were grown of these two clones and the entire insert of each was sequenced and shown to be correct.

EXAMPLE II

Construction of Pichia Pastoris Expression Vectors

Figure 6:
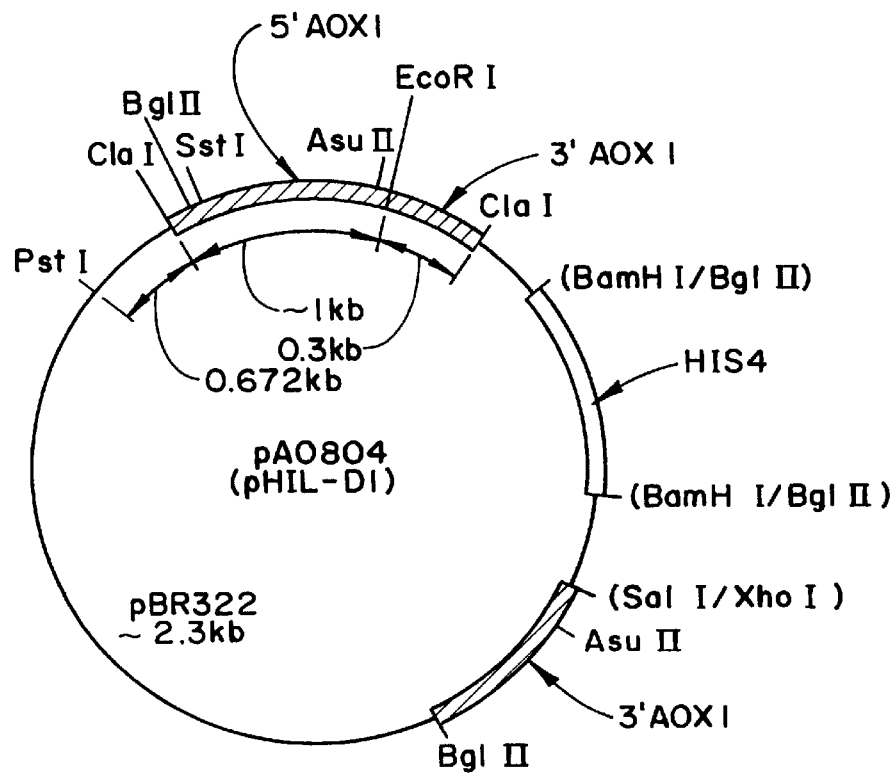
FIG. 6 is a restriction map of plasmid pAO804.
Figure 7:
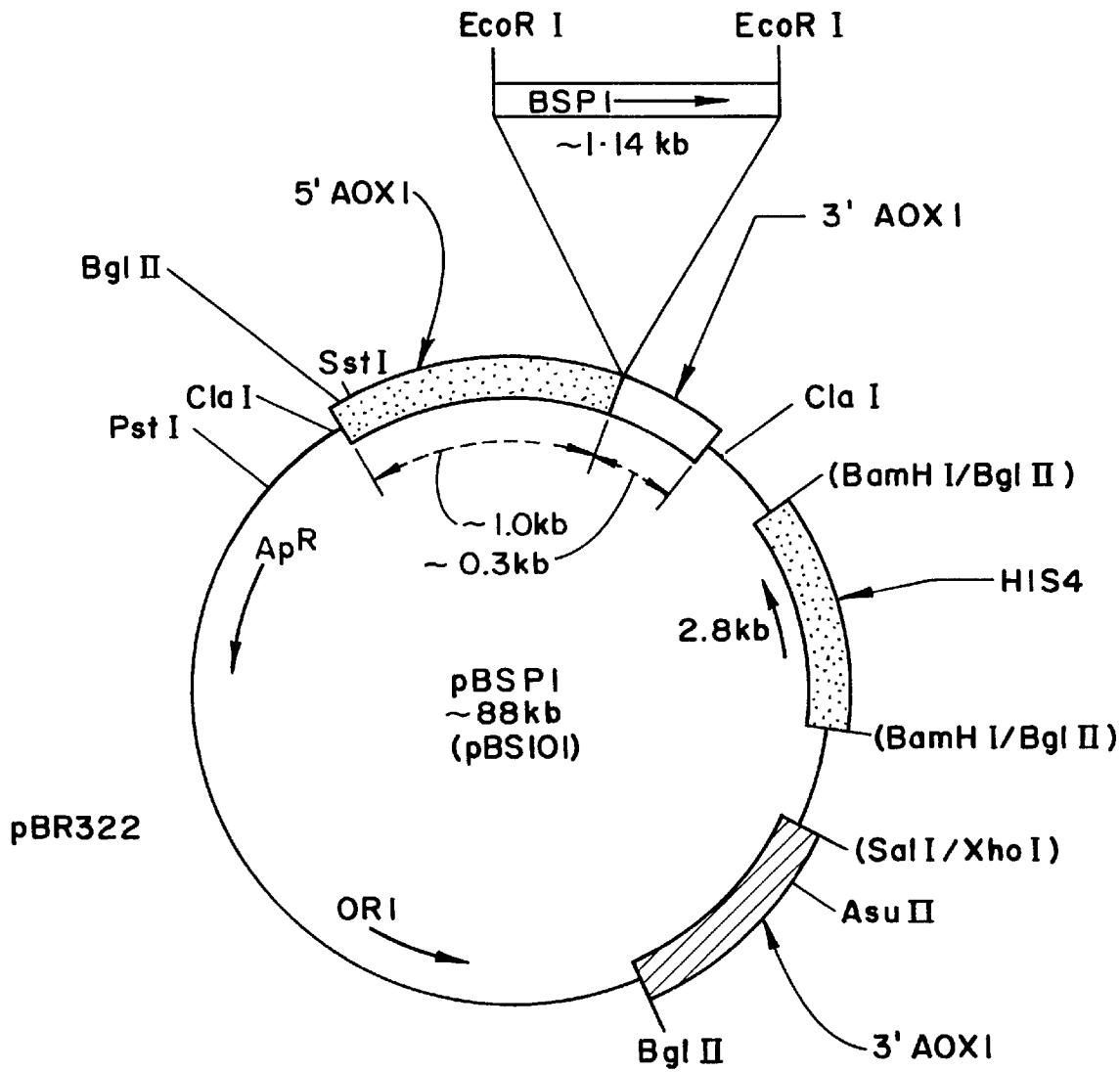
FIG. 7 is a restriction map of plasmid pBSP1 (also referred to herein as pBS101)

Plasmid pAO804 (also referred to herein as pHIL-D1; see FIG. 6) was prepared from plasmids pBSAGI5I (shown in FIG. 5, and available in an *E. coli* host from the Northern Regional Research Center of the United States Department of Agriculture, Peoria, Ill., with the accession number NRRL B-18021), pYJ8 (available in an *E. coli* host from the Northern Regional Research Center of the United States Department of Agriculture, Peoria, Ill., with the accession number NRRL B-15889) and pBR322, as described in U.S. Pat. No. 5,002,876. The BSP1 gene was inserted into pAO804 in either orientation. The orientation of BSP1 gene with respect to the AOX1 promoter was determined by NcoI digestion. Thus, in plasmid pBSP1 (FIG. 7) the gene is in the correct orientation to read off the AOX1 promoter.

EXAMPLE III

Construction of Expression Vectors Containing a 41.9 kd Bacillus Toxin Gene

A. The Native *B. sphaericus* 41.9 kd toxin Gene The 1900 bp EcoRI-HindIII fragment isolated from pBR322-BSP1, containing the toxin gene from *B. sphaericus* strain 1593, was cloned into M13mp10 (BS102-1). In two separate reactions, the template was mutagenized with oligonucleotides that added EcoRI sites at the 5' and 3' ends. After primer extension of the mutagenic oligonucleotides on the single-stranded templates, the heteroduplex DNAs were transformed into JM103. Recombinant phage were identified by transferring plaques onto nitrocellulose and screening them with $^{32}$P-labeled oligonucleotides that hybridized to the respective mutagenized 5' or 3' region. Positive clones were isolated, rescreened and sequenced. Four recombinants having the correct 5' modification were identified and one recombinant having the correct 3' modification was identified.

One recombinant having a correct 5' mutation (BS201-1) and the recombinant having a correct 3' mutation (BS202-4) were used to construct an entire gene flanked by EcoRI sites. In a three-way ligation, a ~600 bp SacI-EcoRI fragment from BS201-1 and a ~1000 bp SacI-HindIII fragment from BS202-4 were cloned into the EcoRI-HindIII polylinker sites in pUC19. After transformation into MC1061, several colonies were isolated and identified as being the correct recombinant (BS301) by restriction digest analysis. A ~1140 bp EcoRI fragment from BS301 was then cloned into the EcoRI site of pAO804 in order to generate the Pichia expression vector. (Plasmid pAO804 is described in U.S. Pat. No. 5,002,876 and in PCT International Publication WO 89/04320.) After transformation into MC1061, several colonies were screened and identified as being the desired construct, pXBS101.

B. Construction of a Pichia expression vector for the expression of the synthetic *B. sphaericus* 41.9 kd toxin gene The large plasmid prep of pSBS100#4 was digested with EcoRI and the 1140 bp fragment was isolated. This fragment was ligated into pAO804 which had been digested with EcoRI, and MC1061 cells were transformed with the ligation mix. RF DNA was prepared from 12 colonies and digested with PstI to check the orientation of the EcoRI insert. Seven of the 12 inserts were in the correct 5'-to-3' orientation. Two of these (pSBS101#1 and #6, also called pBSP1, FIG. 7) were grown up as large-scale plasmid preps and the entire EcoRI cassette and flanking regions of each plasmid were sequenced and found to be entirely correct.

EXAMPLE IV

Synthesis and Construction of a Synthetic *B. Sphaericus* 51.4 kd Toxin (BSP-2) Gene The nucleic acid and deduced amino acid sequences of the 51.4 kd toxin of *B. sphaericus* described by Arapinis, et al., Nucl. Acids Res. 16, 7731 (1988) were subject to computer analysis and a nucleic acid sequence employing Pichia preferred codons encoding the exact amino acid sequence was obtained essentially as described in Example II. Using the sequence generated (FIG. 3), direct transfer was made to disc storage and the two copies validated as being identical. Two fragments were designed (See FIG. 4A and 4B), each with a unique EcoRI site at one end and a HindIII site at the other, to facilitate cloning into pUC18.

The sequences were divided into overlapping oligonucleotide fragments following computer analysis to provide unique and optimal complementarity in overlapping regions used in the gene assembly strategy, as previously described in Example II. FIG. 4A depicts the 36 oligonucleotides used to assemble the first half (fragment A) of the synthetic gene and FIG. 4B depicts the 32 oligonucleotides used to assemble the second half (Fragment B) of the synthetic BSP-2 gene.

The oligonucleotides were synthesized on an Applied Biosystems 380B DNA synthesizer using standard cyanoethyl phosphoramidite chemistry. The oligonucleotides were gel purified and assembled into fragments A and B, respectively. The assembled fragments were cloned via their unique Hind III/EcoRI ends into the polylinker region of the pUC18 plasmid.

Transformants were obtained by selection on agar containing cerbenicillin. Single colonies were used to provide small scale plasmid DNA preparations for restriction digests to confirm the presence of insert in each case.

Transformants containing the correct sized inserts were then used to provide DNA for full sequencing using the di-deoxy method for plasmid DNA. The strategy embodied sequencing bi-directionally using universal and reverse primers for pUC18 together with the appropriate primers for the top and bottom strands of the insert.

The complete gene construct was assembled into pUC18 as a EcoRI-BamHI insert as follows. pUC18 containing fragment A was restricted with EcoRI/BamHI to produce the vector including fragment A; pUC18 contain fragment B was cut with the same enzymes to produce the insert (i.e., EcoRI/BamHI-cut fragment B). The two DNAs (i.e., pUC18 including fragment A and EcoRI/BamHI-cut fragment B) were then purified and ligated together. After transformation, a clone containing the complete sequence was identified. This was used to provide cesium chloride purified DNA for final sequencing.

The correct clone was named pUC18-BSP2.

EXAMPLE V

Construction of Expression Vector Containing a Synthetic 51.4 kd Bacillus Toxin Gene A. Construction of pHIL D2

Plasmid pHIL-D2 (FIG. 8) was constructed starting from pAO804, pBR322 and bacteriophage f1 DNA as follows.

Step 1. Preparation of f1-ori DNA f1 bacteriophage DNA (50 $\mu$g) was digested with 50 units of RsaI and DraI at 37° C. for 4 hours in 200 $\mu$l of MS buffer (50 mM NaCl, 10 mM Tris-Hcl (pH 7.5), 10 mM MgCl$_2$, 100 $\mu$g/ml bovine serum albumin) to release the ~458 bp DNA fragment containing the f1 origin of replication (ori). The digestion mixture was extracted with an equal volume of phenol:chloroform (V/V) followed by extracting the aqueous layer with an equal volume of chloroform. Finally, the DNA in the aqueous phase was precipitated by adjusting the NaCl concentration to 0.2M and adding 2.5 volumes of absolute ethanol. The mixture was allowed to stand on ice (4° C.) for 10 minutes and the DNA precipitate was collected by centrifugation for 30 minutes at 10,000×g in a microfuge at 4° C. The DNA pellet was washed 2 times with 70% aqueous ethanol. The washed pellet was vacuum dried and dissolved in 25 $\mu$l of TE buffer. This DNA was electrophoresed on 1.5% agarose gel and the gel portion containing the ~458 bp fl-ori fragment was excised out and the DNA in the gel was electroeluted into 500 $\mu$l of 5 mM EDTA pH 8.0). The DNA solution was phenol:chloroform extracted as detailed above and the DNA precipitate was dissolved in 25 $\mu$l of TE buffer (f1-ori fragment).

Step 2. Cloning of f1-ori into DraI Sites of pBR322 pBR322 (2 $\mu$g) was partially digested with 2 units DraI in 20 $\mu$l of MS buffer at 37° C. for 10 minutes. The reaction was terminated by phenol:chloroform extraction followed by precipitation of DNA as detailed in Step 1 above. The DNA pellet was dissolved in 20 $\mu$l of TE buffer. About 100 ng of this DNA was ligated with 100 ng of f1-ori fragment (Step 1) in 20 μl of ligation buffer by incubating at 14° C. overnight with 1 unit of T4 DNA ligase. The ligation was terminated by heating at 70° C. for 10 minutes and then used to transform E. coli strain YMC9 (Sambrook et al., Molecular Cloning: A Laboratory Manual (Cold Spring Harbor Laboratory Press, 1989) to obtain pBRf1-ori which contains f1-ori cloned into the DraI sites (nucleotide positions 3232 and 3251) of pBR322.

Step 3. Creation of pA0807 pBRfl-ori (10 μg) was digested for 4 hours at 37° C. with 10 units each of PstI and NdeI. The digested DNA was phenol:chloroform extracted, precipitated and dissolved in 25 μl of TE buffer as detailed in Step 1 above. This material was electrophoresed on a 1.2% agarose gel and the NdeI-PstI fragment (approximately 0.8 kb) containing the fl-ori was isolated and dissolved in 20 μl of TE buffer as detailed in Step 1 above. About 100 ng of this DNA was mixed with 100 ng of pA0804 that had been digested with PstI and NdeI and phosphatase treated. This mixture was ligated in 20 μl of ligation buffer by incubating for overnight at 14° C. with 1 unit of T4 DNA ligase. The ligation reaction was terminated by heating at 70° C. for 10 minutes. This DNA was used to transform E. coli strain YMC9 to obtain pA0807.

Figure 8:
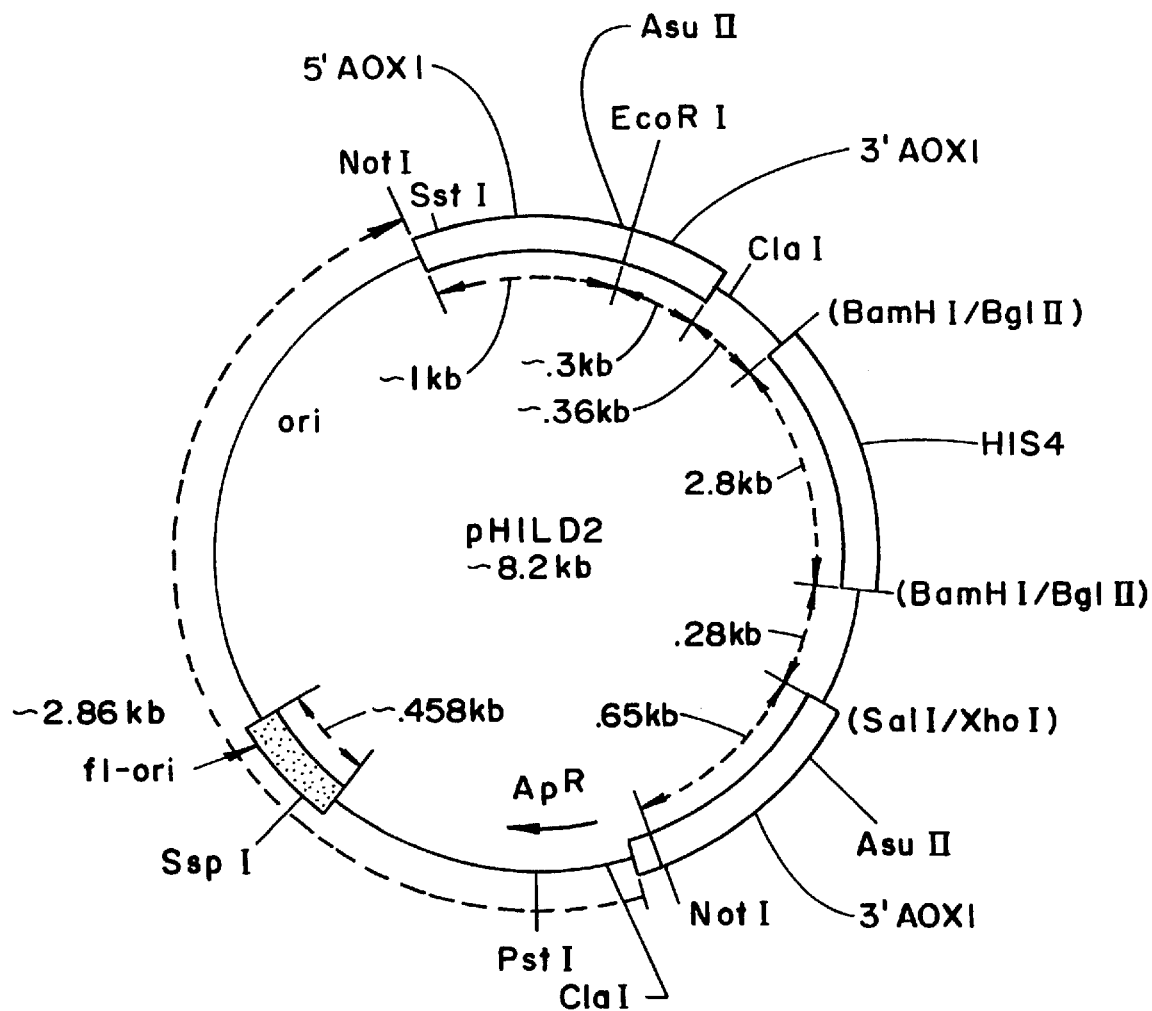
FIG. 8 is a restriction map of plasmid pHIL D2.

Step 4. Conversion of the Two BglII Sites in pA0807 to NotI Sites to Create pHIL D2 pA0807 (10 μg) was digested with 10 units of BglII for 4 hours at 37° C. in 50 μl of HS buffer (150 mM NaCl, 10 mM Tris-HCl (pH 7.5), 10 mM MgCl$_2$, 100 μg/ml bovine serum albumin). The BglII cohesive ends were filled in by incubating the BglII cleaved DNA (10 μg) in 50 ul of NT buffer (50 mM Tris-HCl (pH 7.2), 1 mM MgCl$_2$, 1 mM ZnCl$_2$, 1 mM spermidine) with 5 units of the Klenow fragment of DNA polymerase at room temperature for 30 minutes. This mixture was phenol:chloroform extracted and the DNA was recovered as described in Step 1 above. The DNA pellet was dissolved in 25 μl of TE buffer. This DNA was mixed with 50 ng (1 μl) of phosphorylated NotI linker (pGCGGCCGC) obtained from New England Biolabs, 40 μl of 5× ligation buffer, 129 μl water and 5 units of T4 DNA ligase. This mixture was incubated overnight at 14° C. Ligation was terminated by heating to 70° C. for 10 minutes. Following this the ligation mixture was digested with 10 units of NotI after adjusting the solution to HS buffer condition. The DNA was precipitated after phenol:chloroform extraction as detailed in Step 1 above. The precipitate was dissolved in 50 μl of TE buffer and electrophoresed on a 0.9% agarose gel. The DNA fragments (lower band corresponded to the migration position of the fragment containing pBR322 portion with the f1-ori and the upper band corresponded to the remaining portion of pA0807 (i.e., 5'AOX1, 3'AOX1 and HIS4) were isolated from the gel by using the protocol described in Step 1 above. The gel purified DNA fragments were dissolved in 10 μl of TE buffer. The DNA fragment representing the linear site specific integrative vector was phosphatased by incubating for 30 minutes with 2 units of CIAP at 37° C. in 200 μl of phosphatase buffer (50 mM Tris-HCl (pH 7.0), 1 mM MgCl$_2$, 1 mM MgCl$_2$). The phosphatased DNA was phenol:chloroform extracted and precipitated as described in Step 1. This DNA was mixed with the upper band DNA representing the rest of the pA0807 plasmid (see above) and ligated overnight at 4° C. with 5 units of T4 DNA ligase in 30 μl of ligation buffer. The ligation mixture was heated for 10 minutes at 70° C., cooled on ice and a 10 μl aliquot was used to transform E. coli YMC9 to obtain pHIL D2. The structure of PHIL D2 is shown in FIG. 8.

Figure 9:
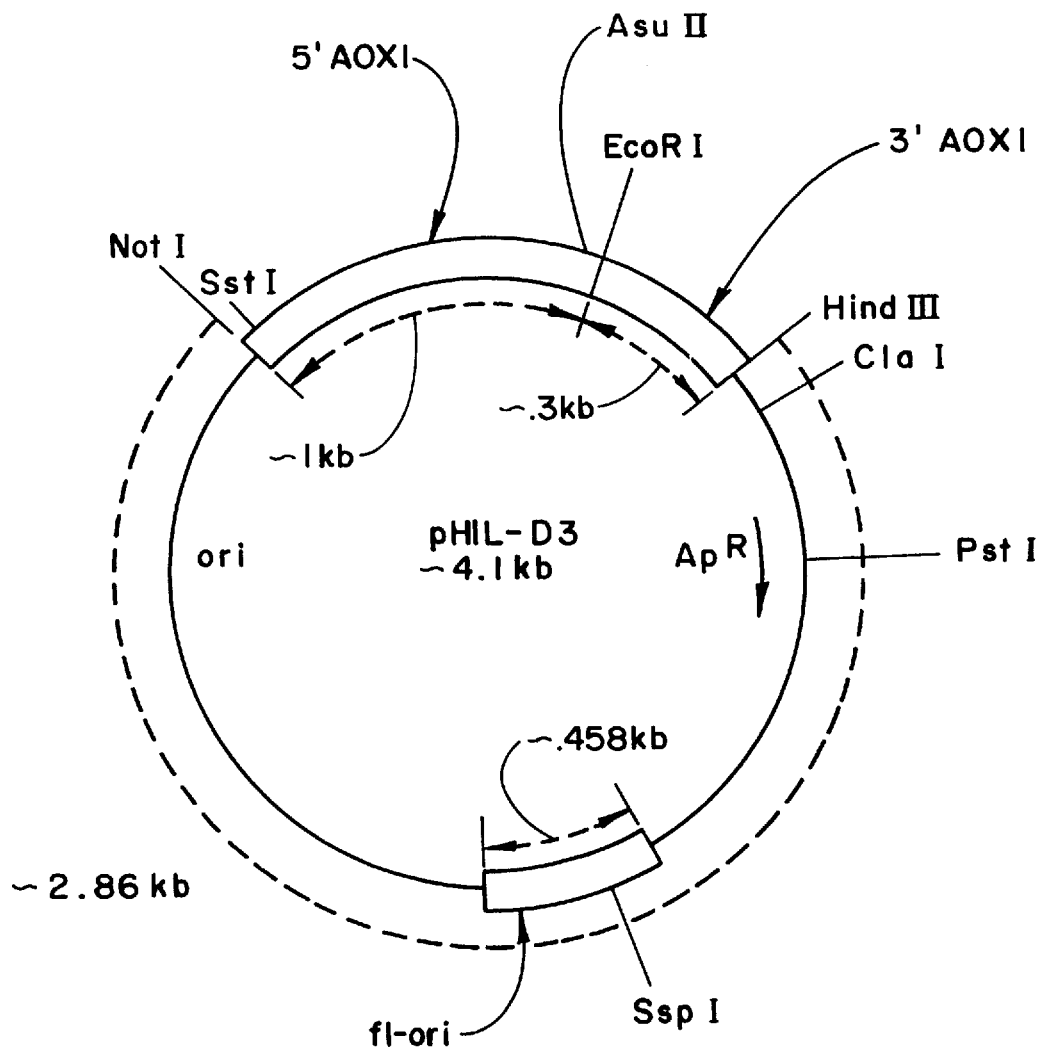
FIG. 9 is a restriction map of plasmid pHIL D3.

B. Construction of pHIL-D3 pHIL-D2 (1 μg) was digested with Cla I which results in two fragments of nearly the same size. The 4.1 Kb fragment containing bulk of the bacterial sequences, alcohol oxidase promoter and terminator sequences was self ligated to get pHIL-D3 vector (see FIG. 9). The other 4.1 Kb Cla I fragment containing HIS4 and the 3'AOX1 stretch was isolated and saved for later use by digesting pHIL-D2 with ClaI and SstI (which gives 3 fragments: 4.1 kb, 2.8 kb and 1.3 kb) and isolating the 4.1 Kb fragment.

C. Construction of pBSP2

Step 1.

The pUC18-BSP2 plasmid (described in Example IV) was synthesized by British Biotechnology, Ltd., Abington, Oxon, Great Britain. The BSP2 gene is present as Asu II-EcoRI fragment within the Hind III-Eco RI sites of pUC18. To adopt BSP2 into P. pastoris expression vector, BSP2 was excised out as Asu II-Eco RI fragment and cloned into the Asu II-Eco RI sites of pHIL-D3 to obtain pBSP2-Cla.

Figure 10:
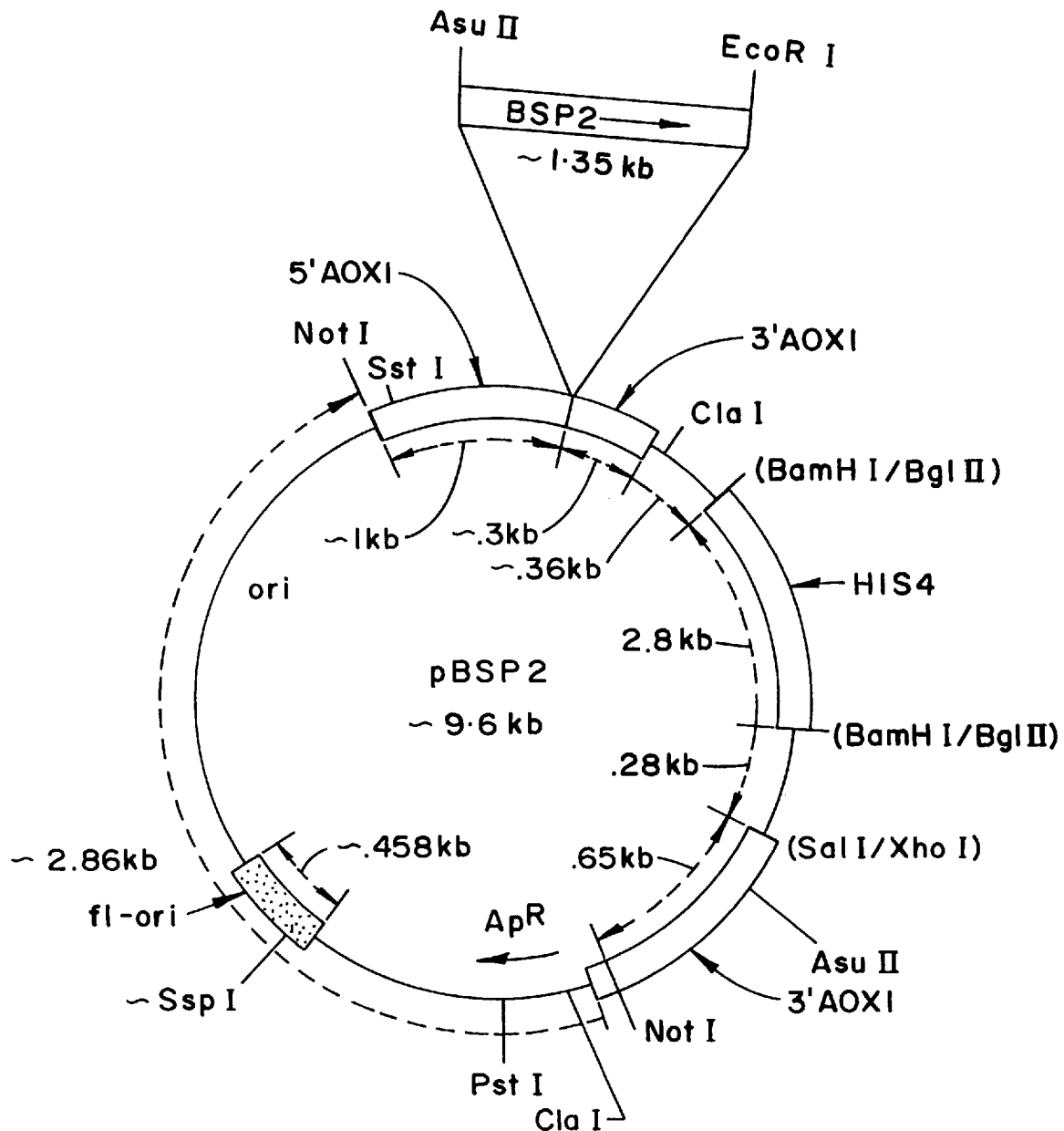
FIG. 10 is a restriction map of plasmid pBSP2.

Step 2.

pBSP2-Cla was digested with Cla I and ligated with the Cla I fragment of pHIL-D2 (containing HIS4 and 3'-AOX1 stretch) previously isolated (see, section B. of this Example). The resulting fragment with correct orientation of the Cla I fragment (confirmed by the size of the fragments obtained by Asu II digestion) is the plasmid pBSP2 (FIG. 10).

EXAMPLE VI

Figure 11:
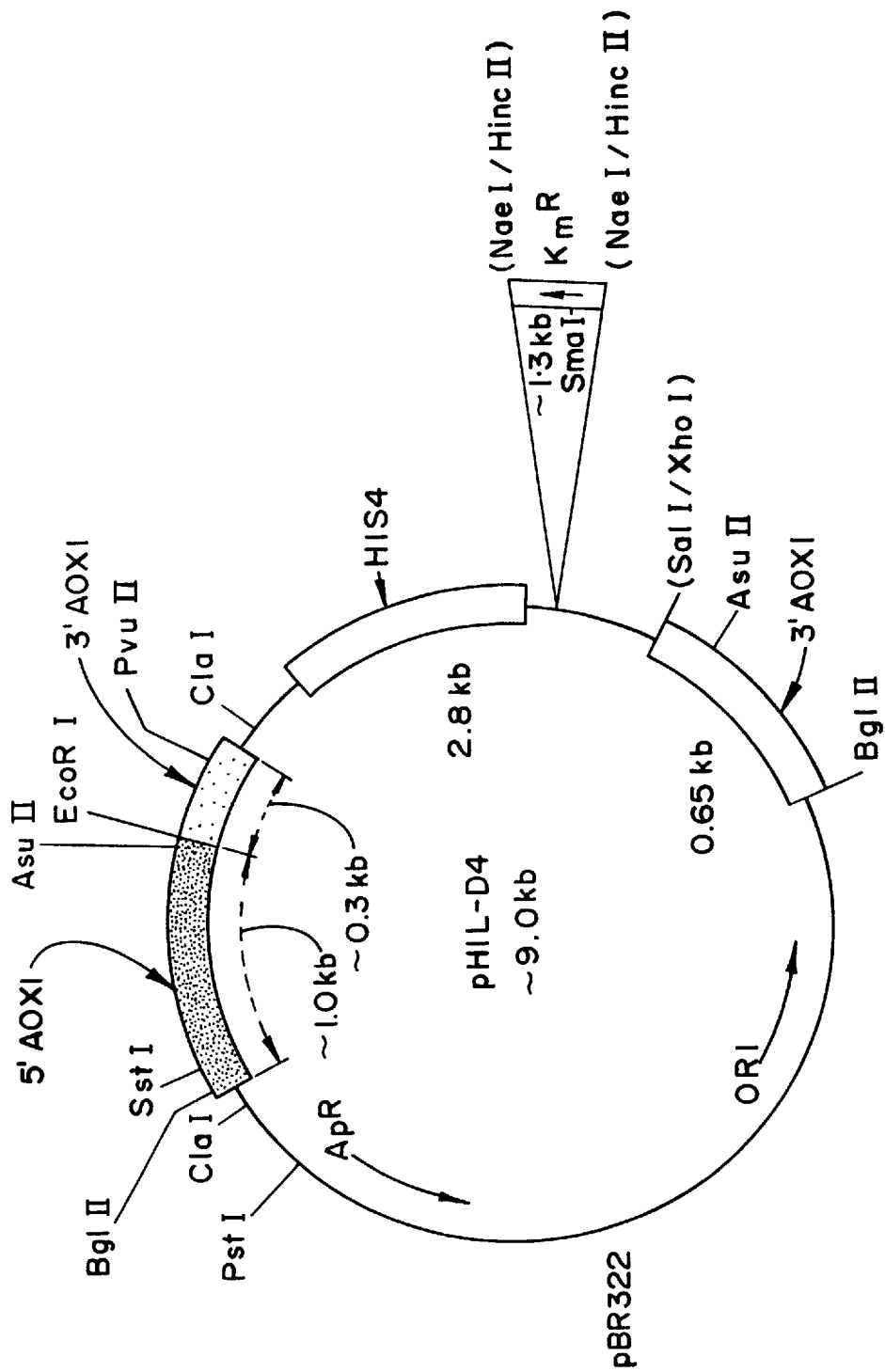
FIG. 11 is a restriction map of plasmid pHIL D4.

Construction of Expression Vector Containing a Synthetic 41.9 kd B. Sphaericus Toxin Gene and a 51.4 kd B. Sphaericus Toxin Gene A. Construction of pHIL-D4 pHIL-D1 (i.e., pAO804) was digested with Nae I (there is a unique Nae I site in the sequence derived from pBR322 which is used to link HIS 4 and 3'AOXI in pHIL-D1) and ligated with bacterial kanamycin resistance gene containing Hinc II fragment obtained from pUC-4K vector (commercially available from PL-Biochemicals, Piscataway, N.J.). The resulting plasmid with the kanamycin resistance gene was screened based on simultaneous Ap and Km resistance phenotypes of E. coli transformed with the recombinant plasmid. The direction of orientation of the Km-resistance gene was also determined by analysis of restriction digests. The correct plasmid was named pHIL D4 (FIG. 11).

B. Construction of pHIL-D5

Step 1.

pHIL-D2 (1 μg) was digested with Asu II and alkaline phosphatase treated. Asu II cuts at two places. The larger fragment that contains most of the bacterial sequences, 5'-AOX1, and portions of 3'-AOX1 was recovered.

Step 2.

pHIL-D4 (1 μg) was digested with Bgl II (cuts at two sites) and phosphatase treated. Then it was further digested with Asu II.

Step 3.

Figure 12:
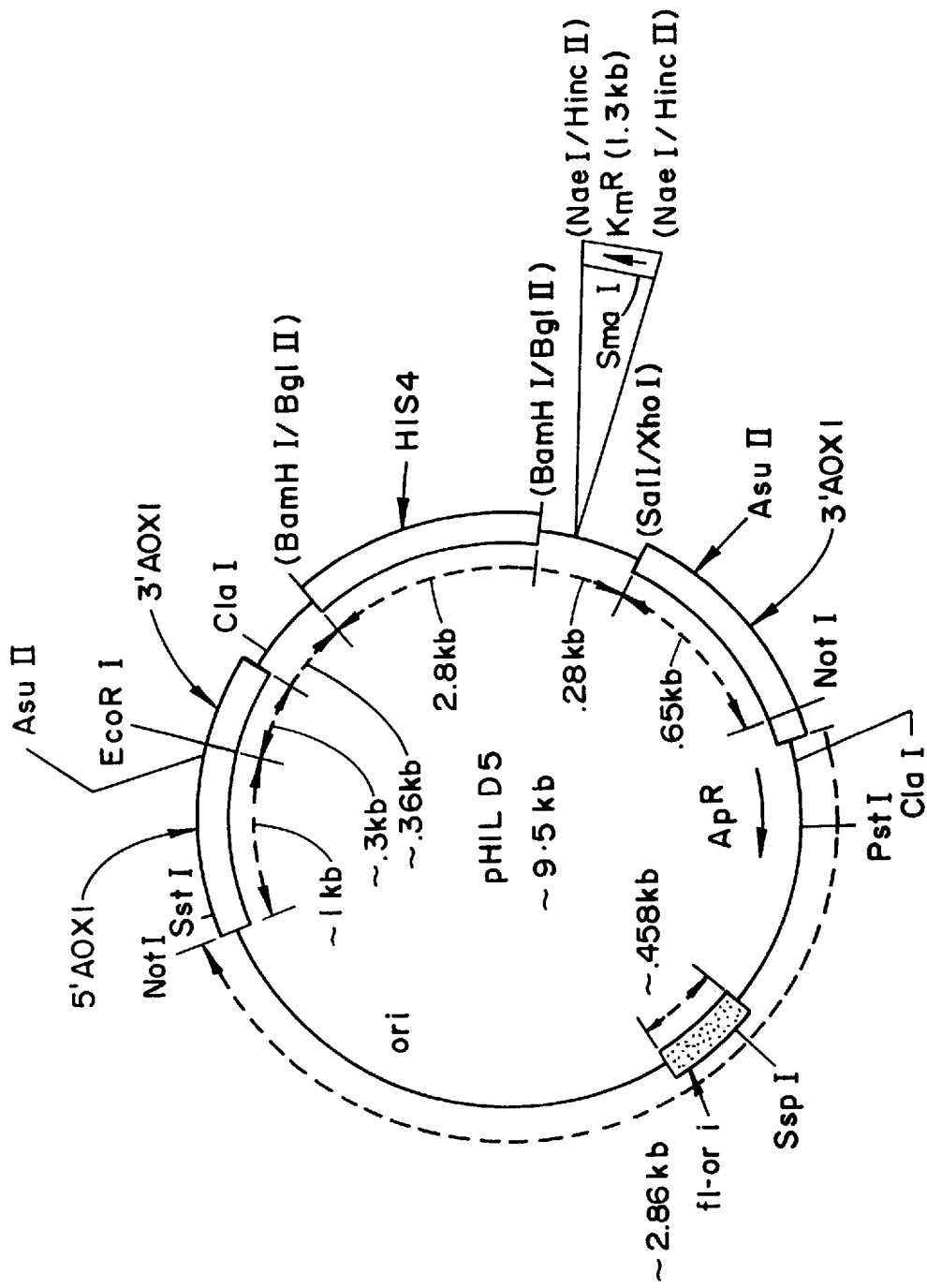
FIG. 12 is a restriction map of plasmid pHIL D5.

The larger AsuII fragment obtained in Step 1 was ligated with fragments in Step 2. The ligated DNA was used to transform E. coli strain DG75' to $Ap^R K_m^R$. Plasmid DNA isolated from several such transformants was screened for the correct orientation of the Asu II fragment containing the $K_m$ resistance gene and HIS4 with respect to the rest of the vector, by digestion with EcoRI and SstI. In the correct orientation, EcoRI-SstI digestion will yield two fragments: ~1 kb and ~8.5 kb in size. In the wrong orientation the fragments will be about 4.7 kb and 4.8 kb. The vector with the desired correct orientation is designated as pHIL-D5 (FIG. 12).

C. Construction of pBSP2-$K_m$ pHIL-D5 was digested with EcoRI and Sst I. Two fragments are obtained. The larger fragment (vector backbone) was isolated after gel electrophoresis on 0.9% agarose.

Figure 13:
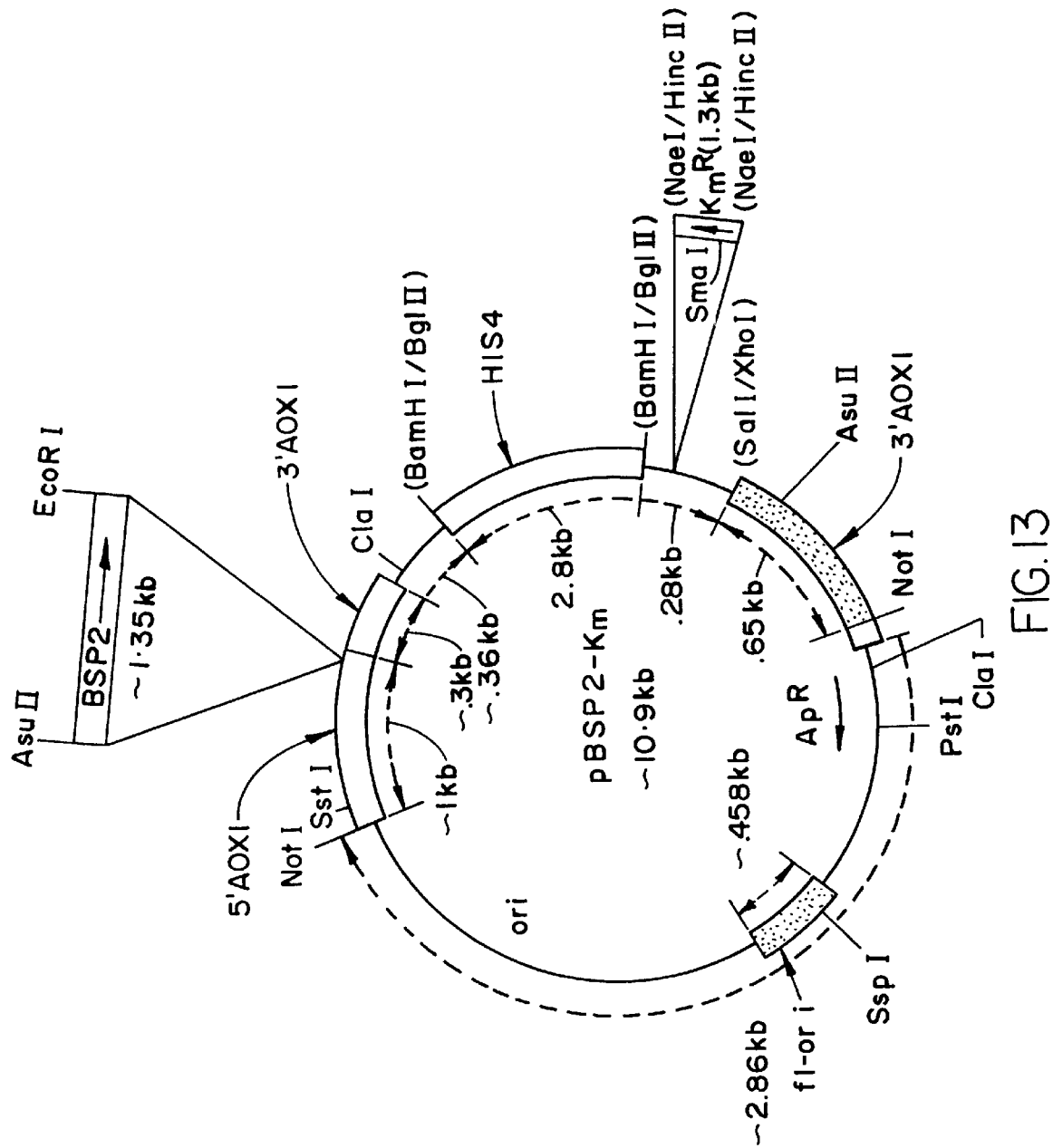
FIG. 13 is a restriction map of plasmid pBSP2-Km.

Plasmid pBSP2 was digested with EcoRI and SSt I to produce two fragments (~2.2 Kb and ~7.4 Kb) were produced. The smaller fragment (~2.2 kb) was isolated and ligated into the vector backbone of pHIL-D5 obtained in Step 1. The ligated DNA was used to transform E. coli strain DG75' to $Ap^R Km^R$. E. coli transformants were screened to confirm the presence of pBSP2-Km (shown in FIG. 13) by restriction digestion analysis with BamHI which gave the expected 10.9 kb fragment.

D. Construction of pBSP1+2

Step 1.

pBSP2-Km was digested with Sma I, which cuts in the $K_m^R$ gene, and alkaline phosphatase treated.

Figure 14:
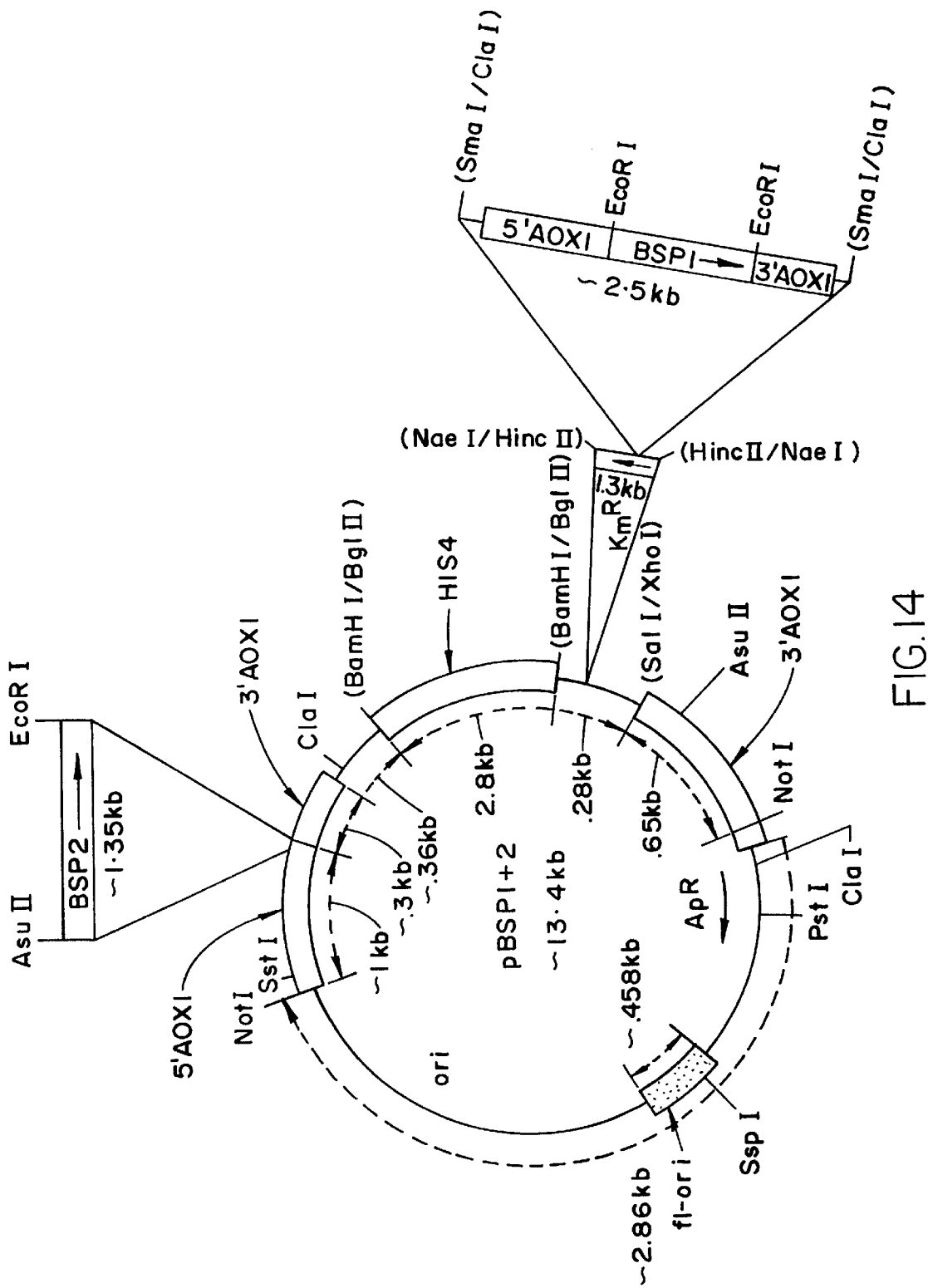
FIG. 14 is a restriction map of plasmid pBSP1+2.

Step 2.

pSBS101 (also referred to herein as pBSP1; described in Example I) was cut with Cla I and the ~2.5 kb fragment containing the BSP1 gene with 5' AOX1 and AOX1 terminator sequences was isolated and blunt ended by treatment with Klenow fragment of E. coli DNA polymerase. This fragment was ligated with the Sma I-cut pBSP2-Km from in Step 1. Ligated DNA was used to transform E. coli to $AP^R Km^R$. Several transformants were screened for correct size (13.4 kb) to arrive at pBSP1+2 (FIG. 14). The orientation of the BSP1 containing fragment was determined by the size of the EcoRI fragments obtained on digestion.

EXAMPLE VII

Transformation of P. Pastoris Cells with pXBS101, pSBS101, pBSP2-Km or pBSP1+2

Transformation of P. pastoris cells was carried out by digesting (1) plasmid pXBS101 with restriction endonuclease SalI (His4 integration) or BglII (AOX1 integration), (2) plasmid pSBS101 with the restriction endonuclease StuI (His4 integration) or with SacI (AOX1 integration), (3) plasmid pBSP2-Km with NotI (AOX1 integration and (4) plasmid pBSP1+2 with NotI (AOX1 integration) and using the resulting linearized transforming DNA to transform the cells using the spheroplast yeast transformation system.

P. pastoris strain GS115 (NRRL Y-15851), a histidine-requiring auxotroph (His$^-$) of P. pastoris was used as the host for transformation with plasmid pXBS101 or pSBS101. P. pastoris GS115 grows efficiently on methanol in a defined minimal medium supplemented with histidine and is a desirable host system for purposes of heterologous protein production.

Digestion of pSBS101 (synthetic 41.9 kd toxin gene) or pXBS101 (native 41.9 kd Bacillus gene) with BglII releases a DNA fragment with ends homologous to regions 5' and 3' to the P. pastoris AOX1 gene locus. With respect to pBSP2-Km (synthetic 51.4 kd toxin gene) and pBSP1+2 (both synthetic 41.9 kd and 51.4 kd toxin genes) the BglII sites were converted to NotI sites. Digestion of pBSP2-Km or pBSP1+2 with NotI also releases a DNA fragment with ends which are homologous to regions 5' and 3' to the AOX1 gene locus. When such a fragment is transformed into a His$^-$ P. pastoris strain and maintained there under selective conditions (histidine-free medium), a replacement type integration at the AOX1 locus of the expression cassette-containing fragment (containing the HIS4 gene) is effected in some cells. This integration results in cells having a Mut$^{+/-}$ (also referred to as Mut$^-$) phenotype due to the loss of the AOX1 gene product, but retention of the minor alcohol oxidase gene product (AOX2) which allows slow growth on methanol. This 1-step gene replacement technique, resulting in integration of the heterologous gene into a P. pastoris chromosome avoids difficulties related to plasmid instability, distribution and copy number. The technique also results in the incorporation of a minimum amount of heterologous DNA into the P. pastoris genome. Cells which are transformed by integration at the AOX1 gene will be His$^+$ and can be distinguished by a slower growth rate on methanol as compared to cells in which integration occurred at sites other than the AOX1 locus. In cells in which integration has occurred at a site other than the AOX1 locus or in which integration has not occurred, the AOX1 gene remains functional and such cells have a faster growth rate on methanol.

With respect to addition-type integration, digestion of pSBS101 with SacI releases a DNA fragment with ends homologous to the 5'-end region, but not the 3'-end region, of the P. pastoris AOX1 gene locus. Such a DNA fragment can integrate by addition at the AOX1 structural gene, and results in cells having a Mut$^+$ phenotype since the AOXI gene is not disrupted. Digestion of pXBS101 with SalI analogously releases a DNA which can integrate by addition into the his4 locus of P. pastoris. Cells which are so transformed, with addition-type integration occuring at either the AOXI locus or the his4 locus will be His$^+$/Mut$^+$, such that they may be identified by their ability for fast growth on methanol.

The spheroplast transformation method (see, e.g., U.S. Pat. No. 4,879,231) is preferred because it provides a large number of transformants.

A colony of P. pastoris GS115 is inoculated into about 10 ml of YPD medium (10 g yeast extract, 20 g peptone and 10 g dextrose in 1,000 ml distilled water) and incubated at as a shake culture at 30° C. for 12 to 20 hours. The cells are then diluted to an $OD_{600}$ of about 0.01–0.1 and maintained in log growth phase in YPD medium for about 6–8 hours. Then about 100 ml of YPD medium is inoculated with 0.5 ml of the seed culture at an $OD_{600}$ of about 0.1 (or equivalent amount). The culture is incubated at 30° C. for about 12–20 hours on a shaker. The culture is harvested when $OD_{600}$ is about 0.2–0.3 (after approximately 16–20 hours) by centrifugation at 1500×g for 5 minutes.

The harvested cells are used to prepare spheroplasts. All centrifugations for preparing washed cells (as opposed to spheroplasts) are at 1500×g for 5 minutes. The cells are washed once in 10 ml of sterile water, once in 10 ml of freshly prepared SED (1M sorbitol, 25 mM EDTA, 50 mM dithiothrietol, adjusted to pH 8) and then twice in 10 ml of sterile 1M sorbitol. The washed cells are then resuspended in 10 ml of SCE buffer (1M sorbitol, 10 mM sodium citrate, 1 mM EDTA, adjusted to pH 5.8 with HCl). To the SCE buffer are added 5–10 µl of a 3 mg per ml zymolyase 100,000 (Miles Laboratories, Elkhart, Ind.), and the cells are incubated at 30° C. for about 5–10 minutes to yield spheroplasts. The preparation of spheroplasts is a critical step in the transformation procedure. Spheroplast formation was monitored during incubation by adding 100 µl aliquots of cells to 900 µl of 5% SDS or 900 µl of 1M sorbitol before and at various times after the addition of zymolyase 100,000 to check for cell lysis. Incubation was stopped at the point where cells lysed in SDS but not in sorbitol. The spheroplasts were washed twice in 10 ml of sterile 1M sorbitol by centrifugation at 1,000×g for 5–10 minutes, and once in 10 ml of sterile CaS buffer (1M sorbitol, 10 mM Tris-HCl (pH 7.5), 10 mM $CaCl_2$). The time and speed for centrifugation may vary; centrifuge enough to pellet spheroplasts but not so much that they rupture from the force. The spheroplasts were resuspended in a volume of 0.6 ml CaS buffer.

Vector DNA for transforming the spheroplasts was prepared (after isolation on a CsCl gradient) by digesting vector pXBS101 with BglII (AOXI integration) or SalI (HIS4 integration) and digesting vector pSBS101 (also referred to herein as pBSP1) with SacI (SacI and SstI are isoschizomers) or StuI. Complete digestion was verified on an agarose gel. The BglII digested pXBS101 vector and the SacI digested pSBS101 vector contain a *Bacillus sphaericus* 41.9 Kd toxin-encoding (native and synthetic sequences, respectively) cassette (including the AOX1 promoter and terminator segments), the *P. pastoris* HIS4 gene for a selection, and an additional 3'-AOX1 fragment to direct, along with the 5'-AOX1 fragment with the promoter, integration of the linearized fragment into the AOX1 locus of *P. pastoris*. Integration of the linearized fragment at the AOX1 locus disrupts the AOX1 gene and results in stable integration of the toxin expression unit into the genome of the *P. pastoris* host. The transformed cell becomes methanol-utilization defective ($Mut^{+/-}$) as a result of the AOX1 disruption. The AOX2 gene, which is not disrupted, allows slow growth on methanol.

Transformation of the spheroplast with SalI digested pXBS101 or StuI digested pSBS101 results in integration of the entire plasmid into the HIS4 locus. The transformed cells are methanol-utilization competent ($Mut^+$) because the AOX1 gene is not disrupted, and are able to grow on methanol with a higher growth rate than $Mut^{+/-}$.

Restriction endonuclease-digested pXBS101 and pSBS101 (from 1 $\mu$l up to 20 $\mu$l volume at 1 mg/ml) was added to 12×75 mm sterile polypropylene tubes. The DNA should be in water or TE buffer (10 mM Tris-HCl, 1 mm EDTA, pH 8). For maximum transformation efficiencies with small amounts of DNA about 1 $\mu$l of 5 mg/ml sonicated *E. coli* DNA may be added to each sample. 100 $\mu$l of spheroplasts were added to each DNA sample and incubated at room temperature for about 20 minutes. Then 1 ml of PEG solution (20% PEG 3350, 10 mM Tris-HCl (pH7.5), 10 mM $CaCl_2$) was added to each sample and the samples were incubated at room temperature for about 15 minutes. The samples were centrifuged at 1000×g for 5–10 minutes and the PEG solution decanted. The samples were resuspended in 150 $\mu$l of SOS (1M sorbitol, 0.3× YPD medium, 10 mM $CaCl_2$) and incubated for 30 minutes at room temperature. 850 $\mu$l of sterile 1M sorbitol was added and aliquots of samples were plated as described below.

Regeneration of spheroplasts was carried out in Regeneration Agar Medium, which was prepared as follows: 30 ml of 10× glucose solution (20 g dextrose, 100 ml $H_2O$) and 30 ml of 10× SC (6.75 g YNB (bactoyeast nitrogen base without amino acids and ammonium sulfate, Difco Laboratories, Detroit, Mich.) 100 ml $H_2O$) were autoclaved; both 10× solutions were added to 300 ml of melted Agar-KCl solution (9 g Bacto-agar, 13.4 g KCl, 240 ml $H_2O$, autoclaved). 0.6 ml of 0.2 mg/ml biotin was added. In addition, only for the control plates, histidine was added to a concentration of 20 $\mu$g/ml. The melted Regeneration Agar was held at 55°–60° C. A bottom Agar layer of 10 ml Regeneration Agar per plate was poured at least 30 minutes before transformation samples were ready. 10 ml aliquots of Regeneration Agar were distributed to tubes in a 45°–50° C. bath during the period of transformation samples were in SOS. A quantity of each sample was added to 10 ml aliquots of melted Regeneration Agar (held at 45°–50° C.) and poured onto plates containing a solid 10 ml bottom Agar layer of Regeneration Agar.

The quality of the spheroplasts preparation was determined by removing 10 $\mu$l of one sample and adding it to 990 $\mu$l of 1M sorbitol (i.e. 100-fold dilution). 10 $\mu$l of the 100-fold dilution was removed and diluted to an additional 100 times by addition of a second 990 $\mu$l aliquot of 1M sorbitol. A spread plate of both dilutions was made (100 $\mu$l aliquots each) on YPD Agar medium to determine the concentration of unspheroplasted whole cells remaining in the preparation. 100 $\mu$l of each dilution was added to 10 ml of regeneration Agar supplemented with 40 $\mu$g/ml histidine to determine total regeneratable spheroplasts. Good values for a transformation experiment were $1–3\times10^7$ total regeneratable spheroplasts/ml at about $1\times10^3$ whole cells/ml.

The plates were incubated for 3 to 5 days at 30° C. and were selected for $His^+$ ($Mut^+$ or $Mut^{+/-}$) colonies. The $HIS^+$ colonies were pooled, sonicated and replated to obtain single colonies. The observed transformation efficiency with pXBS101 and pSBS101 range between $10^3$ and $10^4$ transformations per $\mu$g plasmid DNA.

A. Native 41.9 Kd toxin gene

The host strain GS115 (NRRL Y-15851) was transformed with SalI-digested pXBS101 to direct integration into the HIS4 locus or BglII-digested pXBS101 to direct gene replacement of the AOX1 locus. Twelve transformants from each reaction were colony purified.

Each of the 24 transformants was analyzed by Southern hybridization to determine the site of integration and copy number. The results of these analyses showed that the twelve transformants isolated after transformation with the BglII-cut vector, seven had integrated the vector at the AOX1 locus. Of these, five were single integration events while the remaining two are thought to be multiple integration events. Four transformants had a hybridization pattern indistinguishable from the parental untransformed strain, these are presumed to be the result of a gene conversion event at the HIS4 locus. One transformant could not be analyzed in this experiment due to a technical difficulty. Of the twelve transformants isolated after transformation with the SalI-cut vector, nine had integrated the vector at the HIS4 locus. Two of these were the result of a multiple copy integration event, while the other seven were single copy integration events. The remaining three transformants had a hybridization pattern identical to the untransformed parental strain and are presumed to be the result of a gene conversion event at the HIS4 locus.

One strain was selected for analysis in a fermentor:

| STRAIN NAME | SITE OF INTEGRATION | GROWTH PHENOTYPE | COPY NUMBER |
|---|---|---|---|
| G + NBS101C3 | HIS4 | $Mut^+$ | single |

B. Synthetic 41.9 Kd toxin Gene

*Pichia pastoris* strain GS115 (NRRL Y-15851) was host for transformation with plasmid pSBS101. The plasmid was either digested with SacI, to direct integration into the AOX1 locus, or with StuI, to direct integration into the HIS4 locus. GS115 cells were separately transformed with either 2 $\mu$g, 5 $\mu$g, or 10 $\mu$g of either digested DNA. The transformants were sonicated and replated onto YNB glycerol plates. Eight patches from each type of transformation were used to inoculate YPD for mini DNA preps.

Each of the 16 transformants was analyzed by Southern hybridization to determine the site of integration and copy number. The results of these analyses showed that eight transformants had integrated the vector at the HIS4 locus, four had integrated the vector at AOX1, one was wild-type, and three transformants had an aberrant integration pattern. Five transformants were analyzed in shake flask studies:

| STRAIN NAME | SITE OF INTEGRATION | COPY NUMBER |
|---|---|---|
| G + SBS101C4 | AOX1 | one |
| G + SBS101C5 | AOX1 | one |
| G + SBS101C10 | HIS4 | multi-copy* |
| G + SBS101C11 | HIS4 | one |
| G + SBS101C12 | HIS4 | multi-copy* |

*copy number not determined

One of the AOX1 integrants (#5) and one of the HIS4 integrants (#10) were selected for further studies in one-liter fermentors.

C. Synthetic 51.4 Kd toxin Gene

*Pichia pastoris* strain GS115 (NRRL Y-15851) was host for transformation with plasmid pBSP2-Km. The plasmid was digested with NotI to direct integration into the AOX1 locus. GS115 cells were transformed with 10 μg of the Not-I digested pBSP2-Km plasmid. The transformants were sonicated, diluted and plated onto YNB glucose plates. One hundred methanol slow transformants were identified by replica plating onto YNB methanol plates. The methanol slow transformants were plated onto YPD-G418 plates and twelve transformants resistant to greater than 1 mg/ml G418 (antibiotic, Sigma) were identified. (Single copy integrants are resistant to not more than about 200 μg/ml G418, whereas multi-copy integrants are resistant to greater than 1 mg/ml G418. Dot-blot analyses also indicated the presence of multiple copies.) These strains were used for expression of the 51.4 Kd toxin in shake flasks.

One of the AOX1 integrants G/BSP2 (#9) was selected for further studies.

| STRAIN NAME | SITE OF INTEGRATION | COPY NUMBER |
|---|---|---|
| G/BSP2(#9) | AOX1 | multi-copy* |

*copy number not determined

D. Synthetic 41.9 Kd toxin together with 51.4 Kd toxin Gene

*Pichia pastoris* strain GS115 (NRRL Y-15851) was host for transformation with plasmid pBSP1+2. The plasmid was digested with NotI to direct integration into the AOX1 locus. GS115 cells were separately transformed with 10 μg of the Not⁻I digested pBSP1+2. One hundred methanol slow transformants were identified by replica plating onto YNB methanol plates. The methanol slow transformants were plated onto YPD-G418 plates and twelve transformants resistant to greater than 1 mg/ml G418 (antibiotic, Sigma) were identified as multi-copy integrants. These strains were used for expression of the 51.4 Kd toxin in shake flasks.

One of the AOX1 integrants G/BSP1+2 (#9) was selected for further studies.

| STRAIN NAME | SITE OF INTEGRATION | COPY NUMBER |
|---|---|---|
| G/BSP1 + 2 | AOX1 | multi-copy* |

*copy number not determined

EXAMPLE VIII

Insecticidal Activity of Transformed *P. pastoris* Expressing Bacillus Entomotoxin Polypeptides This example describes the production and detection of *Bacillus sphaericus* toxin activity expressed by transformed *P. pastoris* cells of the invention. Expression of both the 41.9 kd and the 51.4 kd toxin polypeptides is necessary to achieve significant toxin activity, as shown by the Table 3 below.

The *Pichia pastoris* strains which are defined in Table 1 were used in the bioassays for determining larvicidal activity.

GENOTYPE OF PICHIA STRAINS
USED IN BIOASSAY FOR LARVICIDAL ACTIVITY

| Strain | Expression cassette | Site of integration (Mut⁺ or Mut⁻) | Copy# |
|---|---|---|---|
| Pichia G/BSP1(#1) | Synthetic BSP1 | AOX1 (Mut⁻) | One |
| Pichia G + SBS101C5 | Synthetic BSP1 | AOX1 (Mut⁺) | One |
| Pichia G + NBS101C3 | Native BSP1 | HIS4 (Mut⁺) | One |
| Pichia G/BSP2(#9) | Synthetic BSP2 | AOX1 (Mut⁻) | multi-copy* |
| Pichia G/BSP1 + BSP2(#9) | Synthetic BSP1 + 2 | AOX1 (Mut⁻) | multi-copy* |
| Pichia G/pHIL-D1 | Vector control | AOX1 (Mut⁻) | One |

*copy number not determined

For expression of larvicidal activity in transformed *P. pastoris* cells, cells of each of the *P. pastoris* strains were inoculated into 20 ml of MGY medium in 50 ml shake tubes. The composition of MGY medium (carbon source is glycerol) is: 100 ml of 10× YNB (13.4 grams of yeast nitrogen base (YNB- Difco) without amino acids in 100 ml of water) 2 ml of biotin (200 μg/ml), 100 ml of 10% v/v glycerol, q.s. 1 liter (deionized water). The tubes were incubated in a shaker (250 revolutions/minute) at 30° C. for two days. At the end of this period, the optical density at 600 nm of the cultures was approximately 10. The cultures were centrifuged (2000×g for 5 minutes) and the cell pellets were resuspended in 20 ml methanol-containing medium [100 ml of 10× YNB (13.4 grams of yeast nitrogen base (YNB, Difco) without amino acids in 100 ml of water) 2 ml of biotin (200 μg/ml), 100 ml of 5% methanol V/V, q.s. 1 liter] and were returned to the 30° C. shaker and shook at 250 revolutions per minute for 4 days (final $OD_{600}$ ~10–15). The cells were centrifuged (2000×g for 5 minutes) and the cell pellets resuspended in deionized water, serially diluted and used for whole cell mosquitocidal toxicity assays as described below.

The following *B. sphaericus* strains were used in the assays as positive controls, as well as to provide a source of either the native 41.9 kd toxin or the native 51.4 kd toxin, each in the absence of the other:

*B. sphaericus* 1593M (contains both the 41.9 kd and the 51.4 kd toxin polypeptides (wild type)

*B. sphaericus* 718/pUE1-3a (makes only the 41.9 kd toxin polypeptide)

*B. sphaericus* 718/pUE381 (makes only the 51.4 kd toxin polypeptide)

*B. sphaericus* 718 (does not make 41.9 kd or 51.4 kd toxin polypeptide)

The *B. sphaericus* strains were grown in medium having the following composition, based on Kalfon et.al., J. Gen. Microbiol. 130:893–900 (1984): 0.1M Tris-HCl(pH 7.5), 225 mg $K_2HPO_4$, 260 mg $CaCl_2 \cdot 2H_2O$, 300 mg $MgSO_4 \cdot 7H_2O$, 2.0 g $ZnSO_4 \cdot 7H_2O$, and 1.4 g $FeCl_3 \cdot 6H_2O$, 2 g yeast extract (Difco Labs, Detroit, Mich.) 10 grams of tryptone (Difco), q.s. 1 liter (deionized water).

*B. sphaericus* cultures were incubated at 30° C. The cultures were maintained in exponential phase by several (3–4) serial transfers in the same medium. After the final transfer, samples of the cultures were periodically removed and $O.D._{620}$ was measured. While the $O.D._{620}$ of the cultures was about 4–8 when the Bacillus cultures were in the spore-forming stage, to determine more accurately when the cultures should be harvested for the bioassay (i.e., when spore concentration is elevated), the appearance of mature spores was monitored by withdrawing duplicate aliquots from each culture, plating one aliquot from each culture directly onto solid medium and heating the other aliquot to 80° C. for 12 minutes before plating on solid medium. [Solid medium was prepared by adding 20 grams of agar (Difco) to the above liquid medium.] The plates were read one day after plating; Bacillus cultures were used in the toxicity assay when they showed more than 50% surviving cells in the heat treated sample, as compared to the non-heat treated sample. When the cultures were determined to have a sufficient concentration of mature spores, they were centrifuged (2000×g for 5 minutes) and the cell pellets were used for whole cell mosquitocidal toxicity assays.

The protein concentration of the toxin expressing Pichia (and Bacillus) cells were measured to determine total protein used per assay. With respect to the transformed Pichia cells, the pelleted cells from about a 20 ml volume of the respective cultures was resuspended in 5 ml water. 0.5 ml of the resuspended cells was removed, pelleted (2000×g for 5 minutes), and the cell pellets were washed once and resuspended in breaking buffer (50 mM sodium phosphate, pH 7.4, 1 mM, PMSF, 1 mM EDTA and 5% glycerol) at an $A_{600}$ of 50–100. The Pichia cells were broken by vortexing for a total of 4 minutes in increments of 30 seconds, followed by 30 seconds on ice (total time is 8 minutes) with an equal volume of acid-washed glass beads (size 0.5 mm). Each sample was centrifuged in a microfuge for 10 minutes (larger samples were centrifuged at 10,000 rpm for 10 minutes in a Sorvall SM24 or SA600 rotor). The clear supernatant solution was transferred to a fresh tube and mixed with an equal volume of SDS-PAGE loading buffer (0.1 M Tris, 2% SDS, pH 6.8) and boiled for 5 minutes. After the clear supernatant was removed, a 100 μl aliqot of SDS-PAGE loading buffer was added to each pellet (i.e., insoluble fraction remaining after the cells were lysed and centrifuged) and boiled for 5 minutes. The soluble (i.e., supernatant) and insoluble fractions were subjected to polyacrylamide gel electrophoresis. The gels were then stained for protein, and quantified using scanning densitometry and the amount of protein corresponding to the 41.9 kd polypeptide and/or the 51.4 kd polypeptide was determined, as compared to known amounts of BSA used as a standard. The quantity of the respective polypeptides from the soluble and insoluble fractions are reported in Table 2.

TABLE 2

MOSQUITOCIDAL TOXIN LEVEL
IN PICHIA STRAINS DESCRIBED IN TABLE 1

| Strain | mg toxin polypeptide/g total protein | |
|---|---|---|
| | 41.9 kd | 51.4 kd |
| Pichia G/BSP1(#1) | 40 | 0 |
| Pichia G + SBS101C5 | 33 | 0 |
| Pichia G + NBS101C3 | 0 | 0 |
| Pichia G/BSP2(#9) | 150 | 0 |
| Pichia G/BSP1 + BSP2(#9) | 50 | 60 |
| Pichia G/pHIL-D1 | 0 | 0 |

G = GS115

With respect to the Bacillus cultures, the total protein was determined by solubilizing the Bacillus cells in breaking buffer supplemented with 1% SDS, and adjusted to pH 10. The cells were broken using either a french press or by sonication, heated to 100° C. for 5 minutes and then subjected to polyacrylamide gel electrophoresis and total protein was quantitated. Under these conditions essentially all protein is solubilized.

A bioassay based on the ability of the toxin expressing cells to kill susceptible insect larvae was then performed. Insect eggs were purchased from Carolina Biological Supply Co. (Burlington, N.C.) and were placed in deionized water supplemented with 2 mg/ml dried yeast extract to allow the eggs to hatch. Larvae at the second to third instar stage of development were selected for use in the bioassay.

Aliquots of whole cells (Pichia and Bacillus) of each of the respective strains were serially diluted, based on total protein, starting with a 1:10 dilution of the stock cell suspension and continuing with serial 1:10 dilutions until a concentration of less than one nanogram total protein per ml was reached (e.g., about $10^{-8}$ dilution). One or more aliquots (10–100 μl) of each dilution of each cell suspension were added to individual 15 ml cups containing 6 insect larvae of *Culex pipiens* (P. Myers, et al., Can. J. Microbiol. 25, 1227–1231 (1979) in 5 ml of 200 μg/ml dried yeast extract (Difco). Each concentration of toxin was tested at least in duplicate. The bioassay for larvicidal activity was carried out at 25° C. for two days with a photo period of 14 hours of light and 10 hours of dark. After correction for mortality of the controls (less than 7%), the line of best fit was determined for the relation between Probit mortality (F. Matsumura 1975, Toxicology of Insects, pp. 20–22, Plenum Publishing Corp., New York) and the logarithm of toxin concentration by means of linear regression analysis. The dose at which 50% of the larvae were killed within two days, $LC_{50}$ value, is shown in Table 3. In the assays in which Pichia cells and Bacillus cells were combined (i.e., the Bacillus strain was used to provide either the 41.9 kd or the 51.4 kd toxin polypeptide), the quantity of Bacillus cells used was such that the native Bacillus toxin polypeptide was present in 4 to 5-fold molar excess (i.e., a non-limiting concentration) and the $LC_{50}$ concentration given in Table 3 corresponds exclusively to the Pichia produced toxin.

TABLE 3

MOSQUITO-LARVICIDAL ACTIVITY (LC50) OF
NATIVE BACILLUS, TRANSFORMED BACILLUS AND
TRANSFORMED *P. PASTORIS* CELLS WHICH
EXPRESS BACILLUS TOXIN POLYPEPTIDES

| Test Material | $LC_{50}$* |
|---|---|
| *B. sphaericus* 718/pUE381 (makes only BSP2) | Inactive |
| *B. sphaericus* 718/1–3a (makes only BSP1) | Inactive |
| *B. sphaericus* 718 (makes neither BSP1 nor BSP2) | Inactive |
| *B. sphaericus* 1593M | 5 ng/ml |
| *B. sphaericus* 2362 | 6 ng/ml |
| Pichia G/BSP1 (#1) | Inactive |
| Pichia G/BSP2 (#9) | Inactive |
| Pichia G/BSP1 (#1) + *B. sphaericus* 718/pUE381 | 1 ng/ml |
| Pichia G/BSP1 (#1) + Pichia G/BSP2 (#9) | 1 ng/ml |
| Pichia G + SBS101C5 (synthetic BSP1 gene) | Inactive |
| Pichia G + SBS101C5 + *B. sphaericus* 718/pUE381 | 3 ng/ml |
| Pichia G + SBS101C5 + Pichia G/BSP2 (#9) | 1 ng/ml |
| Pichia G + NBS101C3 (native BSP1 gene) | Inactive (NA) |
| Pichia G + NBS101C3 + *B. sphaericus* 718/pUE381 | Inactive (NA) |
| Pichia G + NBS101C3 + Pichia G/BSP2 (#9) | Inactive |
| Pichia G/BSP2(#9) + *B. sphaericus* 718/1–3a | 0.5 ng/ml |
| Pichia G/pHIL-D1(#1) | Inactive |
| Pichia G/pHIL-D1(#1) + *B. sphaericus* 718/pUE381 | Inactive |
| Pichia G/pHIL-D1(#1) + *B. sphaericus* 718/1–3a | Inactive |

*Expressed as ng/ml of the estimated total protein
G = GS115

Cell extracts of the transformed *P. pastoris* cultures were also found to have comparable activity to the whole cells.

Cell extracts of *P. pastoris* culture expressing the 41.9 kd polypeptide (BSP1) alone, the 51.4 kd polypeptide (BSP2) alone, and both the 41.9 kd and 51.4 kd toxin polypeptides together as the biologically active complex were further analyzed to show similarity between the expressed heterologous gene product and authentic *B. sphaericus* toxin polypeptides. In activity titration experiments it was found that excess BSP2 relative to BSP1 (i.e., greater than 4-fold excess) inhibits larvicidal activity. The preferred ratio is 1:1, which result correlates well with reults obtained with the native 41.9 kd and 51.4 kd toxin polypeptide produced by *B. sphaericus*. Furthermore, antibody preparations raised against the 41.9 kd and the 51.4 kd polypeptides produced by *B. sphaericus* 2362 are cross-reactive with the 41.9 kd and 51.4 kd polypeptides, respectively, produced by transformed *P. pastoris* cells. Moreover, both the native *B. sphaericus* 41.9 kd polypeptide and the Pichia-expressed 41.9 kd polypeptide give the same 39 kd species upon trypsinization. Finally, the relative potency of the larvicidal toxin complex comprising the 41.9 kd and the 51.4 kd polypeptides expressed in *P. pastoris* cells is equally or more potent than the native *B. sphaericus* toxin complex.

While the various aspects of the present invention have been described herein with some particularity, those skilled in the art will recognize modifications and variations that remain within the spirit of the invention. These modifications and variations are within the scope of the invention as described and claimed herein.

What is claimed is:

1. A DNA which comprises at least one expression cassette, said expression cassette comprising:
   (1) a promoter segment of a first methylotrophic yeast gene, said segment comprising the promoter and transcription initiation site of said first gene;
   (2) a terminator segment of a second methylotrophic yeast gene, said terminator segment comprising the polyadenylation signal-encoding and polyadenylation site-encoding segments and the transcription termination signal of said second gene, said first and second methylotrophic yeast genes being the same or different; and
   (3) a DNA segment which encodes a Bacillus toxin polypeptide, which polypeptide encoding segment has a G+C content of between about 45% and about 55%;
   said polypeptide encoding segment being oriented and positioned operatively for transcription between said promoter segment and said terminator segment, and said terminator segment being oriented, with respect to direction of transcription from said promoter segment, operatively for termination of transcription and
   said Bacillus toxin polypeptide being a biologically active insecticidal toxin.

2. A DNA according to claim 1 wherein said polypeptide encoding region comprises at least about 80% Pichia pastoris preferred codons.

3. A DNA according to claim 1 wherein said first and second species of methylotrophic yeast are the same and are Pichia pastoris and wherein said first and second genes are the same and are the AOX1 gene.

4. A DNA according to claim 3 further comprising at least one selectable marker gene and a bacterial origin of replication.

5. A DNA according to claim 4 wherein said DNA is contained within a circular plasmid.

6. A DNA according to claim 4 wherein the polypeptide encoding region encodes the 41.9 kd toxin of Bacillus sphaericus.

7. A DNA according to claim 4 wherein the polypeptide encoding region encodes the 51.4 kd toxin of Bacillus sphaericus.

8. A DNA according to claim 4 further comprising 3'- and 5'-ends having sufficient homology with a target gene of a yeast host for said DNA fragment to integrate at a site of said target gene.

9. A DNA according to claim 8 which is a BglII-fragment of plasmid pBSP1 capable of integration at the AOX1 gene of Pichia pastoris.

10. A DNA according to claim 8 which is a NotI-fragment of plasmid pBSP2-Km capable of integration at the AOX1 gene of Pichia pastoris.

11. A DNA according to claim 4 which comprises at least two Bacillus toxin polypeptide expression cassettes, wherein the polypeptide encoding segments of the expression cassettes encode the same or different polypeptide.

12. A DNA according to claim 11 comprising a first expression cassette which encodes a first toxin polypeptide and a second expression cassette which encodes a second toxin polypeptide, wherein said first and second toxin polypeptides are different, and wherein said polypeptides are endogenous to the same or different species of the genus Bacillus.

13. A DNA according to claim 12 further comprising 3'- and 5'-ends having sufficient homology with a target gene of a yeast host for said DNA fragment to integrate at a site of said target gene.

14. A DNA according to claim 12 which encodes the 41.9 kd toxin of Bacillus sphaericus and the 51.4 kd toxin of Bacillus sphaericus.

15. A DNA according to claim 14 which is plasmid pBSP1+2.

16. Pichia pastoris transformed with the DNA of claim 12.

17. A methylotrophic yeast cell transformed with a DNA which comprises at least one expression cassette, said expression cassette comprising:
   (1) a promoter segment of a first methylotrophic yeast gene, said segment comprising the promoter and transcription initiation site of said first gene;
   (2) a terminator segment of a second methylotrophic yeast gene, said terminator segment comprising the polyadenylation signal-encoding and polyadenylation site-encoding segments and the transcription termination signal of said second gene, said first and second methylotrophic yeast genes being the same or different; and
   (3) a DNA segment which encodes a Bacillus toxin polypeptide, which polypeptide encoding segment has a G+C content of between about 45% and about 55%;
   said polypeptide encoding segment being oriented and positioned operatively for transcription between said promoter segment and said terminator segment, and said terminator segment being oriented, with respect to direction of transcription from said promoter segment, operatively for termination of transcription and said Bacillus toxin polypeptide being a biologically active insecticidal toxin.

18. A methylotrophic yeast cell according to claim 17 wherein said yeast is *Pichia pastoris*.

19. A methylotrophic yeast cell according to claim 18 wherein said DNA promoter segment is derived from the *Pichia pastoris* AOX1 gene and the terminator segment is derived from the *Pichia pastoris* AOX1 gene.

20. A methylotrophic yeast cell according to claim 19 wherein said DNA further comprises 3'- and 5'-ends having sufficient homology with a target gene of the yeast cell for said DNA to integrate into said target gene.

21. A methylotrophic yeast cell according to claim 20, said cell having one or more copies of the DNA integrated into its genome.

22. A methylotrophic yeast cell according to claim 18, wherein the polypeptide encoding region of the DNA encodes the 41.9 kd toxin of *Bacillus sphaericus*.

23. A methylotrophic yeast cell according to claim 18, wherein the polypeptide encoding region encodes the 51.4 kd toxin of *Bacillus sphaericus*.

24. A methylotrophic yeast cell according to claim 18, wherein the DNA comprises at least two Bacillus toxin polypeptide expression cassettes, wherein the first expression cassette encodes a first toxin polypeptide and the second expression cassette encodes a second toxin polypeptide and wherein the first and second toxin polypeptides are different and are endogenous to the same or different species of the genus Bacillus, and wherein said cell has one or more copies of the DNA integrated into its genome.

25. A methylotrophic yeast cell according to claim 24, wherein the DNA encodes the 41.9 kd toxin of *Bacillus sphaericus* and the 51.4 kd toxin of *Bacillus sphaericus*.

26. A methylotrophic yeast cell according to claim 25, wherein the DNA is plasmid pBSP1+2.

27. A methylotrophic yeast cell according to claims 21, 24, 25, or 26, wherein said cell is a multi-copy integrant.

28. A culture of yeast cells according to claims 17, 18, 19, 20, 22, 23, 21, 16, 24, 25, or 26 which comprises at least about 1% Bacillus toxin polypeptide(s) by weight based on total protein of said yeast cells.

29. An insecticidal composition comprising killed Bacillus toxin-expressing methylotrophic yeast cells, wherein said toxin is expressed from a DNA which comprises at least one expression cassette, said expression cassette comprising:

(1) a promoter segment of a first methylotrophic yeast gene, said segment comprising the promoter and transcription initiation site of said first gene;

(2) a terminator segment of a second methylotrophic yeast gene, said terminator segment comprising the polyadenylation signal-encoding and polyadenylation site-encoding segments and the transcription termination signal of said second gene, said first and second methylotrophic yeast genes being the same or different; and (3) a DNA segment which encodes a Bacillus toxin polypeptide, which polypeptide encoding segment has a G+C content of between about 45% and about 55%;

said polypeptide encoding segment being oriented and positioned operatively for transcription between said promoter segment and said terminator segment, and said terminator segment being oriented, with respect to direction of transcription from said promoter segment, operatively for termination of transcription and said Bacillus toxin polypeptide being a biologically active insecticidal toxin.

30. A method of making at least one Bacillus toxin polypeptide comprising culturing cells of a methylotrophic yeast cell transformed with DNA which is capable of expressing in said yeast cell at least one gene encoding said Bacillus toxin polypeptide under conditions such that said gene is transcribed, wherein said Bacillus toxin polypeptide is expressed at levels of at least about 10 percent relative to the total protein expressed.

31. A method according to claim 30 wherein said methylotrophic yeast is a strain of *Pichia pastoris*.

* * * * *

UNITED STATES PATENT AND TRADEMARK OFFICE
CERTIFICATE OF CORRECTION

PATENT NO. : 5,827,684
DATED : October 27, 1998
INVENTOR(S) : K. Sreekrishna, et al.

It is certified that error appears in the above-identified patent and that said Letters Patent are hereby corrected as shown below:

On The Title Page, [56] References Cited, U.S. PATENT DOCUMENTS:

"Herrnstadtt" should read --Herrnstadt--

Column 14, Line 63: "SamI" should read --SmaI--

Column 20, Line 36: "Hinc II" should read --Hind II--

Column 26, Line 6: Insert --TABLE 1--

Signed and Sealed this

Fifteenth Day of May, 2001

*Attest:*

NICHOLAS P. GODICI

*Attesting Officer*     *Acting Director of the United States Patent and Trademark Office*